US009079960B2

(12) United States Patent
Chu et al.

(10) Patent No.: US 9,079,960 B2
(45) Date of Patent: *Jul. 14, 2015

(54) METHODS AND COMPOSITIONS FOR INHIBITING CD32B EXPRESSING CELLS

(75) Inventors: Seung Yup Chu, Cypress, CA (US); John R. Desjarlais, Pasadena, CA (US); Sher Bahadur Karki, Pomona, CA (US); Gregory Alan Lazar, Arcadia, CA (US); Gregory L. Moore, Monrovia, CA (US); Igor Vostiar, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/594,619

(22) Filed: Aug. 24, 2012

(65) Prior Publication Data

US 2012/0321620 A1    Dec. 20, 2012

Related U.S. Application Data

(63) Continuation of application No. 13/301,464, filed on Nov. 21, 2011, which is a continuation of application No. 12/156,183, filed on May 30, 2008, now Pat. No. 8,063,187.

(60) Provisional application No. 60/940,776, filed on May 30, 2007, provisional application No. 60/953,174, filed on Jul. 31, 2007, provisional application No. 60/970,413, filed on Sep. 6, 2007, provisional application No. 60/976,279, filed on Sep. 28, 2007, provisional application No. 60/990,509, filed on Nov. 27, 2007, provisional application No. 61/012,035, filed on Dec. 6, 2007, provisional application No. 61/013,775, filed on Dec. 14, 2007, provisional application No. 61/019,395, filed on Jan. 7, 2008, provisional application No. 61/032,059, filed on Feb. 27, 2008, provisional application No. 61/043,585, filed on Apr. 9, 2008, provisional application No. 61/046,397, filed on Apr. 18, 2008.

(51) Int. Cl.
| | |
|---|---|
| C07K 16/00 | (2006.01) |
| C12P 21/08 | (2006.01) |
| A61K 39/395 | (2006.01) |
| A61K 39/40 | (2006.01) |
| A61K 39/42 | (2006.01) |
| C07K 16/28 | (2006.01) |
| C07K 1/00 | (2006.01) |

(52) U.S. Cl.
CPC .............. *C07K 16/283* (2013.01); *C07K 16/00* (2013.01); *C07K 16/2803* (2013.01); *C07K 16/2851* (2013.01); *C07K 16/2878* (2013.01); *C07K 2317/24* (2013.01); *C07K 2317/52* (2013.01); *C07K 2317/524* (2013.01); *C07K 2317/53* (2013.01); *C07K 2317/71* (2013.01); *C07K 2317/72* (2013.01); *C07K 2317/73* (2013.01); *C07K 2317/732* (2013.01); *C07K 2317/734* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,485,045 A | 11/1984 | Regen et al. |
| 4,544,545 A | 10/1985 | Ryan et al. |
| 4,975,278 A | 12/1990 | Senter et al. |
| 5,013,556 A | 5/1991 | Woodle et al. |
| 5,208,020 A | 5/1993 | Chari et al. |
| 5,264,586 A | 11/1993 | Nicolaou et al. |
| 5,587,459 A | 12/1996 | Uckun |
| 5,677,165 A | 10/1997 | De Boer et al. |
| 5,686,072 A | 11/1997 | Uhr et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,773,001 A | 6/1998 | Hamann et al. |
| 5,804,396 A | 9/1998 | Plowman et al. |
| 6,403,312 B1 | 6/2002 | Dahiyat et al. |
| 6,602,684 B1 | 8/2003 | Umana et al. |
| 6,737,056 B1 | 5/2004 | Presta et al. |
| 6,797,492 B2 | 9/2004 | Daugherty et al. |
| 6,821,505 B2 | 11/2004 | Ward et al. |
| 7,052,873 B2 | 5/2006 | Tsuchiya et al. |
| 7,083,784 B2 | 8/2006 | Dall'Acqua et al. |
| 7,117,096 B2 | 10/2006 | Luo et al. |
| 7,129,261 B2 | 10/2006 | Ng et al. |
| 7,217,797 B2 | 5/2007 | Hinton et al. |
| 7,217,798 B2 | 5/2007 | Hinton et al. |
| 7,288,251 B2 | 10/2007 | Bedian et al. |
| 7,315,786 B2 | 1/2008 | Dahiyat et al. |
| 7,317,091 B2 | 1/2008 | Lazar et al. |

(Continued)

FOREIGN PATENT DOCUMENTS

| | | |
|---|---|---|
| WO | WO 81/01145 | 4/1981 |
| WO | WO 88/07378 | 10/1988 |

(Continued)

OTHER PUBLICATIONS

Colman et al. Research in Immunology, 1994; 145(1): 33-36.*
SEQ ID No. 2 alignment, Jan. 24, 2013, pp. 1-2.*
SEQ ID No. 4 alignment, Jan. 24, 2013, pp. 1-2.*
SEQ ID No. 7 alignment, Jan. 24, 2013, pp. 1-3.*
Alignment of instant SEQ ID No. 7 and the patented SEQ ID No. 7. Jan. 25, 2013. pp. 1-2.*
Alignment of instant SEQ ID No. 2 and SEQ ID No. 9 in the parent Patent US 8,063,187. Jan. 25, 2013. pp. 1-2.*
Amigorena et al., "Cytoplasmic domain heterogeneity and functions of IgG receptors in B lymphocytes," *Science*, 256:5065 (1992) 1808-1812.

(Continued)

*Primary Examiner* — Chun Dahle
(74) *Attorney, Agent, or Firm* — Polsinelli PC

(57) ABSTRACT

The present invention relates to immunoglobulins that bind FcγRIIb+ cells and coengage the antigen on the cell's surface and an FcγRIIb on the cell's surface, methods for their generation, and methods for using the immunoglobulins.

16 Claims, 54 Drawing Sheets

(56) References Cited

U.S. PATENT DOCUMENTS

Figure 3:
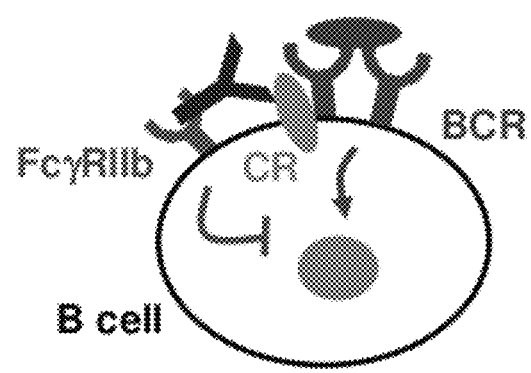

| | | | |
|---|---|---|---|
| 7,335,742 | B2 | 2/2008 | Presta et al. |
| 7,338,660 | B2 | 3/2008 | Bedian et al. |
| 7,361,740 | B2 | 4/2008 | Hinton et al. |
| 7,365,168 | B2 | 4/2008 | Hinton et al. |
| 7,371,826 | B2 | 5/2008 | Presta et al. |
| 7,425,619 | B2 | 9/2008 | Koenig et al. |
| 7,425,620 | B2 | 9/2008 | Koenig et al. |
| 7,445,780 | B2 | 11/2008 | Chu et al. |
| 7,563,442 | B2 | 7/2009 | Bedian et al. |
| 7,618,633 | B2 | 11/2009 | Bedian et al. |
| 7,626,012 | B2 | 12/2009 | Bedian et al. |
| 7,662,925 | B2 | 2/2010 | Lazar et al. |
| 8,063,187 | B2 * | 11/2011 | Chu et al. .................. 530/387.1 |
| 8,362,210 | B2 | 1/2013 | Lazar et al. |
| 8,388,971 | B2 | 3/2013 | Bedian et al. |
| 2002/0048772 | A1 | 4/2002 | Dahiyat et al. |
| 2002/0119492 | A1 | 8/2002 | Chirino et al. |
| 2003/0003097 | A1 | 1/2003 | Reff et al. |
| 2003/0130827 | A1 | 7/2003 | Desjarlais et al. |
| 2003/0157108 | A1 | 8/2003 | Presta et al. |
| 2004/0110226 | A1 | 6/2004 | Lazar et al. |
| 2004/0230380 | A1 | 11/2004 | Chirino et al. |
| 2005/0118174 | A1 | 6/2005 | Presta et al. |
| 2005/0249723 | A1 | 11/2005 | Lazar et al. |
| 2006/0008883 | A1 | 1/2006 | Lazar et al. |
| 2006/0024298 | A1 | 2/2006 | Lazar et al. |
| 2006/0067930 | A1 | 3/2006 | Adams et al. |
| 2006/0121032 | A1 | 6/2006 | Dahiyat et al. |
| 2006/0134105 | A1 | 6/2006 | Lazar et al. |
| 2006/0148009 | A1 | 7/2006 | Barbosa et al. |
| 2006/0173170 | A1 | 8/2006 | Chamberlain et al. |
| 2006/0198840 | A1 | 9/2006 | Dall'Acqua et al. |
| 2006/0233791 | A1 | 10/2006 | Tedder et al. |
| 2007/0135620 | A1 | 6/2007 | Chamberlain et al. |
| 2007/0231329 | A1 | 10/2007 | Lazar et al. |
| 2008/0260731 | A1 | 10/2008 | Bernett et al. |
| 2012/0082664 | A1 | 4/2012 | Bernett et al. |
| 2012/0148578 | A1 | 6/2012 | Chu et al. |
| 2012/0156207 | A1 | 6/2012 | Chu et al. |
| 2012/0263732 | A1 | 10/2012 | Gladue et al. |
| 2013/0024956 | A1 | 1/2013 | Bedian et al. |
| 2014/0010812 | A1 | 1/2014 | Ravetch et al. |

FOREIGN PATENT DOCUMENTS

| | | |
|---|---|---|
| WO | WO 92/11018 | 7/1992 |
| WO | WO 93/21232 | 10/1993 |
| WO | WO 96/30347 | 10/1996 |
| WO | WO 96/33978 | 10/1996 |
| WO | WO 96/33980 | 10/1996 |
| WO | WO 97/34631 | 9/1997 |
| WO | WO 97/38731 | 10/1997 |
| WO | WO 97/38983 | 10/1997 |
| WO | WO 98/43960 | 10/1998 |
| WO | WO 99/06378 | 2/1999 |
| WO | WO 99/06396 | 2/1999 |
| WO | WO 99/09016 | 2/1999 |
| WO | WO 00/61739 | 10/2000 |
| WO | WO 01/29246 | 4/2001 |
| WO | WO 01/59066 | 8/2001 |
| WO | WO 02/30954 | 4/2002 |
| WO | WO 02/31140 | 4/2002 |
| WO | WO 02/060919 | 8/2002 |
| WO | WO 03/014325 | 2/2003 |
| WO | WO 03/074679 | 9/2003 |
| WO | WO 2004/004798 | 1/2004 |
| WO | WO 2004/035752 | 4/2004 |
| WO | WO 2004/091658 | 10/2004 |
| WO | WO 2004/092219 | 10/2004 |
| WO | WO 2005/037867 | 4/2005 |
| WO | WO 2005/047327 | 5/2005 |
| WO | WO 2006/019447 | 2/2006 |
| WO | WO 2006/031370 | 3/2006 |
| WO | WO 2006/047350 | 5/2006 |
| WO | WO 2006/053301 | 5/2006 |
| WO | WO 2006/105338 | 10/2006 |
| WO | WO 2006/133450 | 12/2006 |

OTHER PUBLICATIONS

Ashkenazi et al., "Immunoadhesins as research tools and therapeutic agents," *Curr. Opin. Immunol.*, 9 (1997) 195-200.

Atwell et al., "Stable heterodimers from remodeling the domain interface of a homodimer using a phage display library," *J. Mol. Biol.*, 270 (1997) 26-35.

Barbin et al., "Influence of variable N-Glycosylation on the cytolytic potential of chimeric CD19 antibodies," *J. Immun.*, 29:2 (2006) 122-133.

Beiger-Bompadre et al., "The formyl peptide N-fornyl-methionly-leucyl-phenylalanine downregulates the expression of the FcyRs in interferon-y-activated monocytes/macrophages in vitro and in vivo," *Scand. J. Immunol.*, 57 (2003) 221-228.

Binstadt et al., "IgG Fc receptor polymorphisms in human disease: implications for intravenous immunoglobulin therapy," *J. Allergy and Clinical Immuno.*, 111:4 (2003) 697-703.

Bitoni et al., "Pulmonary delivery of an erythropoietin Fc fusion protein in non-human primates through an immunoglobulin transport pathway," *Proc. Natl. Acad. Sci.*, 101 (2004) 9763-9768.

Blank et al., "Decreased transcription of the human FCGR2B gene mediated by the -343G/C promoter polymorphism and association with systemic lupus erythematosus," *Human Genesis*, 117:2 (2005) 220-227.

Bruggemann et al., "Production of human antibody repertoires in transgenic mice," *Current Opinion in Biotech*, 8 (1997) 455-458.

Campbell et al., "A dominant mutation to ricin resistance in Chinese hamster ovary cells induces UDP-GlcNAc:Glycopeptide beta-4-N-acetylglucosaminyltransferase III activity," *J. Biol. Chem.*, 259:21 (1984) 13370-13378.

Caron et al., "Engineered humanized dimeric forms of IgG are more effective antibodies," *J. Exp. Med.*, 176 (1992) 1191-1195.

Carter et al., "Bispecific human IgC by design," *J. Immunol. Methods*, 248 (2001) 7-15.

Carter et al., "Potent antibody therapeutics by design," *Nature Reviews*, 6 (2006) 343-357.

Cartron et al., "Therapeutic activity of humanized anti-CD20 monoclonal antibody and polymorphism in IgG Fc receptor FcγRIIIa gene," *Blood*, 99:3 (2002) 754-758.

Chamow et al., "Immunoadhesins: principles and applications," *Trends in Biotechnol*, 14:2 (1996) 52-60.

Chan et al., "Regulation of the immune response. VI. Inability of F(ab')2 antibody to terminate established immune responses and its ability to interfere with IgC antibody-mediated immunosuppression," *Immunology*, 24:2 (1973) 289-301.

Chari et al. "Immunoconjugates containing novel maytansinoids: promising anticancer drugs," *Cancer Research*, 52 (1992) 127-131.

Chen et al., "Association of a transmembrane polymorphism of Fcy receptor IIb (FCGR2B) with systemic lupus erythematosus in Taiwanese patients," *Arthritis and Rheumatism*, 54:12 (2006) 3908-3917.

Chin et al., "An expanded eukaryotic genetic code," *Science*, 301 (2003) 964-967.

Chu et al., "Coengagement of BCR coreceptor CD19 and inhibitory Fc receptor gammaRIIb suppresses B cell function: a potential therapeutic strategy for autoimmune disease," Internet: Xencor.com/downloads/biosymposia-b-cell-ibc-abeng-poster-2007-12-11.pdf.

Chu et al., "Inhibition of B cell receptor-mediated activation of primary human B cells by coengagement of CD19 and FcgammaRIIb with Fc-engineered antibodies," *Molecular Immunology*, 45:15 (2008) 3926-3933.

Clark, "IGG effector mechanisms," *Chemical Immunology*, 65 (1997) 88-110.

Cox et al., "Glycan optimization of a human monoclonal antibody in the aquatic plant *Lemna minor*," *Nature Biotechnology*, 24:2 (2006) 1591-1597.

Cropp et al., "An expanding genetic code," *Trends in Genetics*, 20:12 (2004) 625-630.

(56) References Cited

OTHER PUBLICATIONS

Dall'Acqua et al., "Increasing the affinity of a human IgG1 for the neonatal Fc receptor: biological consequences," *Journal of Immunology*, 169 (2002) 5171-5180.
Dall'Ozzo et al., "Rituximab-dependent cytotoxicity by natural killer cells: influence of FCGR3A polymorphism on the concentration-effect relationship," *Cancer Research*, 64 (2004) 4664-4669.
Davies et al. "Expression of GnTIII in a recombinant anti-CD20 CHO production cell line: Expression of antibodies with altered glycoforms leads to an increase in ADCC through higher affinity for FCγRIII," *Biotechnol. Bioeng.*, 74:4 (2001) 288-294.
Davies et al. "Fc receptor homologs: newest members of a remarkably diverse Fc receptor gene family," *Immunological Reviews*, 190 (2002) 123-136.
Defranco et al., "The complexity of signaling pathways activated by the BCR," *Curr. Opin. in Immunol.*, 9 (1997) 296-308.
De Goer De Nerve et al., "Differential Effect of Agonistic Anti-CD40 on Human Mature and Immature Dendritic Cells: The Janus Face of Anti-CD-40", *Blood*, 106 (2005) 2806-2814.
Desai et al., "Fcγ receptor IIB on dendritic cells enforces peripheral tolerance by inhibiting effecetor T cell responses," *J. Immuno.*, 178 (2007) 6217-6226.
De Pascalis et al., "Grafting of 'abbreviated' complementarity-determining regions containing specificity-determining residues essential for ligand contact to engineer a less immunogenic humanized monoclonal antibody," *J. Immunol.*, 169 (2002) 3076-3084.
Dhodapkar et al, "Selective Blockade of Inhibitory Fcγ Receptor Enables Human Dendritic Cell Maturation With IL-12p70 Production and Immunity to Antibody-Coated Tumor Cells", *PNAS*, 102:8 (2005) 2910-2915.
Dickinson et al., "Bidirectional FcRn-dependent IgC transport in a polarized human intestinal epithelial cell line," *J. Clin. Invest.*, 104 (1999) 903-911.
Doody et al., "Activation of B lymphocytes: integrating signals from CD19, CD22 and FcγRIIb1," *Curr. Opin. Immunol.*, 8 (1996) 378-382.
Doronina et al., "Development of potent monoclonal antibody auristatin conjugates for cancer therapy," *Nature Biotech.*, 21:7 (2003) 778-784.
Edelman et al., "The covalent structure of an entire γG immunoglobulin molecule," *Biochemistry*, 63 (1969) 78-85.
Eppstein et al., "Biological activity of liposome-encapsulated murine interferon γ is mediated by a cell membrane receptor," *Proc. Natl. Acad. Sci.*, 82 (1985) 3688-3692.
Floto et al., "Loss of function of a lupus-associated FcγRIIb polymorphism through exclusion from lipid rafts," *Nature Medicine*, 11:10 (2005) 1056-1058.
Francisco et al., "cAC10-vcMMAE, an anti-CD30-monomethyl auristatin E conjugate with potent and selective antitumor activity," *Blood*, 102:4 (2003) 1458-1465.
Fukuyama et al., "The inhibitory Fcγ receptor modulates autoimmunity by limiting the accumulation of immunoglobulin G+ anti-Dna plasma cells," *Nature Immunology*, 6:1 (2005) 99-106.
Gabizon et al., "Pharmacokinetics and tissue distribution of doxorubicin encapsulated in stable liposomes with long circulation time," *J. Natl. Cancer Instl.*, 18 (1989) 1484-1488.
Ghetie et al., "Multiple roles for the major histocompatibility complex Class I-related receptor FcRn," *Annual Rev. Immunol.*, 18 (2000) 739-766.
Gorman et al., "Humanisation of monoclonal antibodies for therapy," *Semin Immunol.*, 2:6 (1990) 457-466.
Griffiths et al., "Strategies for selection of antibodies by phage display," *Current Opinion in Biotech.*, 9 (1998) 102-108.
Hayhurst et al., "High-throughput antibody isolation," *Curr. Opin. in Chem. Biol.*, 5 (2001) 683-689.
Heyman et al., "Feedback regulation by IgG antibodies," *Immunol. Letters*, 88:2 (2003) 157-161.
Hinman et al., "Preparation and characterization of monoclonal antibody conjugates of the calicheamicins: a novel and potent family of antitumor antibiotics," *Cancer Research*, 53 (1993) 3336-3341.

Hinton et al., "Engineered human IgG antibodies with longer serum half-lives in primates," *J. Biol Chem.*, 279:8 (2004) 6213-6216.
Hinton et al., "An engineered human IgG antibody with longer serum half-life," *J. Immunol.*, 176:1 (2006) 346-356.
Hogarth et al., "Fc receptors are major mediators of antibody based inflammation in autoimmunity," *Curr. Opin. in Immunol.*, 14 (2002) 798-802.
Holliger et al., "Engineered antibody fragments and the rise of single domains: antibody engineering and manufacture," *Nature Biotech.*, 23:9 (2005) 1126-1136.
Hubbard et al., "Synthesis and processing of asparagine-linked oligosaccharides," *Annual Rev. Biochem.*, 50 (1981) 555-583.
Hwang et al., "Hepatic uptake and degradation of unilamellar sphingomyelin/cholesterol lipsomes: a kinetic study," *Proc. Natl. Acad. Sci.*, 77:7 (1980) 4030-4034.
Jefferis et al., "IgG-Fc-mediated effector functions: molecular definition of interaction sites for effector ligands and the role of glycosylation," *Immunol. Rev.*, 163 (1998) 59-76.
Jefferis et al., "Interaction sites on human IgG-Fc for FcγR: current models," *Immunol. Letters*, 82:1 (2002) 57-65.
Jones et al., "Replacing the complementarity-determining regions in a human antibody with those from a mouse," *Nature*, 321 (1986) 522-525.
Kan et al., "Thioether-bonded constructs of Fab'y and Fcγ modules utilizing differential reduction of interchain disulfide bonds," *J. Immunol.*, 166 (2001) 1320-1326.
Kaneko et al., "Anti-inflammatory activity of immunoglobulin G resulting from Fc sialylation," *Science*, 313:5787 (2006) 670-673.
Kiener et al., "Co-ligation of the antigen and Fc receptors gives rise to the selective modulation of intracellular signaling in b cells: regulation of the association of phosphatidylinositol 3-kinase and inositol 5-phosphatase with the antigen receptor complex," *J. Biological Chem.*, 272 (1997) 3838-3844.
Kim et al., "Analysis of FcγRIII and IgG Fc polymorphism reveals functional and evolutionary implications of protein-protein interaction," *J. Mol. Evol.*, 53 (2001) 1-9.
Lefranc et al., "Gm, Am and Km immunoglobulin allotypes of two populations in Tunisia," *Human Genetics*, 50:2 (1979) 199-211.
Li et al., "A novel polymorphism in the Fcγ receptor IIB (CD32B) transmembrane region alters receptor signaling," *Arthritis and Rheumatism*, 48:11 (2003) 3242-3252.
Li et al., "CD72 down-modulates BCR-induced signal transduction and diminishes survival in primary mature B lymphocytes," *J. Immunol.*, 176:9 (2006) 5321-5328.
Li et al., "Optimization of humanized IgCs in glycoengineered *Pichia pastoris*," *Nature Biotech.*, 24:2 (2006) 210-215.
Lifely et al., "Glycosylation and biological activity of campath-1H expressed in different cell lines and grown under different culture conditions," *Glycobiology*, 5:8 (1995) 813-822.
Lode et al., "Targeted therapy with a novel enediyene antibiotic calichemamicin $\Theta^I_1$ effectively suppresses growth and dissemination of liver metastases in a syngeneic model of murine neuroblastoma," *Cancer Research*, 53 (1998) 2925-2928.
Lowman et al., "Selecting high-affinity binding proteins by monovalent phage display," *Biochemistry*, 30:45 (1991) 10832-10838.
Mackay et al., "Selective dyregulation of the FcγIIB receptor on memory B cells in SLE," *J. Exp. Med.*, 203:9 (2006) 2157-2164.
Massey, "Catalytic antibodies catching on," *Nature*, 320 (1987) 457-458.
Maynard et al., "Antibody engineering," *Annu. Rev. Biomed. Eng.*, 2 (2000) 339-376.
Mcgaha et al., "Restoration of tolerance in lupus by targeted inhibitory receptor expression," *Science*, (2005) 590-593.
Mechetina et al., "Identification of CD16-2, a novel mouse receptor homologous to CD16/FcγRIII," *Immunogenetics*, 4 (2002) 463-468.
Meeker et al., "A unique human B lymphocyte antigen defined by a monoclonal antibody," *Hybridoma*, 3:4 (1984) 305-320.
Mihaylova et al., "Selective silencing of disease-associated B-lymphocytes by chimeric molecules targeting their Fc gamma IIb receptor," *International Immunology*, 20:2 (2008) 165-175.
Mimura et al., "Role of oligosaccharide residues of IgG1-Fc in FcγRIIb binding," *J. Biol. Chem.*, 276:49 (2001) 45539-45547.

(56) References Cited

OTHER PUBLICATIONS

Morea et al., "Antibody modeling: implications for engineering and design," *Methods*, 20 (2000) 267-279.

Morea et al., "Antibody structure, prediction and redesign," *Biophysical Chem.*, 68 (1997) 9-16.

Muta et al., "A 13-amino-acid motif in the cytoplasmic domain of FcγRIIB modulates B-cell receptor signaling," *Nature*, 368:6466 (1994) 70-73.

Nakamura et al., "Fcγ receptor IIB-deficient mice develop Goodpasture's syndrome upon immunization with type IV collagen: a novel murine model for autoimmune glomerular basement membrane disease," *J. Exp. Med.*, 191:5 (2000) 899-906.

Nechansky et al., "Compensation of endogenous IgG mediated inhibition of antibody-dependent cellular cytotoxicity by glycol-engineering of therapeutic antibodies," *Mole. Immuno.* 44:7 (2007) 1826-1828.

Nielsen et al., "Regulation of b-cell activation by complement receptors and Fc receptors," *Transfus. Med. Hemother*, 32 (2005) 339-347.

Nimmerjahn et al., "Fc gamma receptors: old friends and new family members," *Immunity*, 24:1 (2006) 19-28.

Niwa et al., "Enhancement of the antibody-dependent cellular cytotoxicity of low-fucose IgC1 is independent of FcγRIIIa functional polymorphism," *Clinical Cander Rsch.*, 10 (2004) 6248-6255.

Olferiev et al., "The role of activating protein 1 in the transcriptional regulation of the human FCGR2B promoter mediated by the -343 G_C polymorphism associated with systemic lupus erythematosus," *J. Bio. Chem.*, 282:3 (2007) 1738-1746.

Ono et al., "Role of the inositol phosphatase SHIP in negative regulation of the immune system by the receptor FcγRIIB," *Nature*, 383:6597 (1996) 263-266.

Ozaki et al., "Humanized Anti-HM1.24 Antibody Mediates Myeloma Cell Cytotoxicity That Is Enhanced by Cytokine Stimulation of Effector Cells", *Blood*, 93:11 (1999) 3922-3930.

Penichet et al., "Antibody-cytokine fusion proteins for the therapy of cancer," *J Immunol. Methods*, 248 (2001) 91-101.

Pierce, "Lipid rafts and B-cell activation," *Nat. Rev. Immunol.*, 2:2 (2002) 96-105.

Prakken et al., "Heat shock protein 60 and ajuvant arthritis: a model for t cell regulation in human arthritis," *Springer Seminars in Immunopathology*, 25:1 (2003) 47-63.

Pritchard et al., "B cell inhibitory receptors and autoimmunity," *Immunology*, 108:3 (2003) 263-273.

Radaev et al., "Recognition of IgG by FcγReceptor," *J. Biol. Chem.*, 276:19 (2001) 16478-16483.

Radaev et al., "The structure of a human type III Fcγ receptor in complex with Fc," *J. Bio. Chem.*, 276:19 (2001) 16468-16477.

Raghavan et al., "Fc receptors and their interactions with immunoglobulins" *Annu. Rev. Cell Div. Biol.*, 12 (1996) 181-220.

Rankin et al., "CD32B, The Human Inhibitory Fc-γ Receptor IIb, as a Target for Monoclonal Antibody Therapy of B-Cell Lymphoma", *Blood*, 108 (2006) 2384-2391.

Ravetch et al., "IgG Fc receptors" *Annu. Rev. Immunol.*, 19 (2001) 275-290.

Ravetch et al., "Immune inhibitory receptors: frontiers in cellular immunology," *Science*, 290 (2000) 84-89.

Roque et al., "Antibodies and genetically engineered related molecules: production and purification," *Biotechnol. Prog.*, 20 (2004) 639-654.

Samuelsson et al., "Anti-inflammatory activity of IVIG mediated through the inhibitory Fc receptor," *Science*, 291 (2001) 484.

Scallon et al., "Higher levels of sialylated Fc glycans in immunoglobulin G molecules can adversely impact functionality," *Mol. Immunol*,. 44:7 (2007) 1524-1534.

Shields et al., "High resolution mapping of the binding site on human IgG1 for Fcγ RI, Fcγ RII, Fcγ RIII, and FcRn and design of IgG1 varients with improved binding to the FcγR," *J. Biol. Chem.*, 276:9 (2001) 6591-6604.

Shields et al., "Lack of fucose on human IgG1 n-linked oligosaccharide improves binding to human FcγRIII and antibody-dependent cellular toxicity," *J. Biol. Chem.*, 277:30 (2002) 26733-26740.

Shinkawa et al., "The absence of fucose but not the presence of galactose or bisecting n-acetylglucosamine of human IgG1 complex-type oligosaccharides shows the critical role of enhancing antibody-dependent cellular cytotoxicity," *J. Biol. Chem.*, 278:5 (2003) 3466-3473.

Shopes et al., "A genetically engineered human IgG mutant with enhanced cytolytic activity," *J Immunol.*, 148:9 (1992) 2918-2922.

Simmons et al., "Expression of full-length immunoglobulins in *Esherichia coli*; rapid and efficient production of a aglycosylated antibodies," *J. Immunol. Methods*, 263 (2002) 133-147.

Smith et al., "Filamentous fusion phage: novel expression vectors that display cloned antigens on the virion surface," *Science*, (1985) 1315-1317.

Sonderman et al., "Molecular basis for immune complex recognition: A comparison of Fc-Receptor structures," *J. Mol. Biol.*, 309 (2001) 737-749.

Sonderman et al., "The 3.2-Å crystal structure of the human IgG1 Fc fragment-FcγRIII complex" *Nature*, 406 (2000) 267-273.

Stefanescu et al., "Inhibitory Fc gamma receptors: from gene to disease," *J. Clinical Immunol.*, 24:4 (2004) 315-326.

Stevenson et al., "Engineered antibody for treating lymphoma," *Recent Res. in Cancer Research*, 159 (2002) 105-112.

Su et al., "Expression profile of FcγRIIb on leukocytes and its dysregulation in systemic lupus erythematosus," *J. Immunol.*, 178:5 (2007) 3272-3280.

Tan et al., "CD40-CD40L interaction in Alzheimer's disease," *Current Opinion in Pharmacology*, 2 (2002) 445-451.

Tan et al., "'Superhumanized' antibodies: reduction of immunogenic potential by complementarity-determining region grafting with huma germline sequences: application to an Anti-CD28," *J. Immunol.*, 169 (2002) 1119-1125.

Tchorbanov et al., Elective silencing of DNA-specific B lymphocytes delays lupus activity in MRL/1pr mice,: *Euro. J. Immuno.*, 37:12 (2007) 3587-3596.

Thrush et al., "Immunotoxins: an update," *Ann. Rev. Immunol.*, 14:49 (1996) 71.

Trail et al., "Monoclonal antibody drug conjugates in the treatment of cancer," *Curr. Opin. Immunol.*, 11 (1999) 584-588.

Tridandapani et al., "Role of SHIP in FcGamma RIIB-mediated inhibition of Ras activation in B cells," *Mole. Immunol*,.35:17 (1998) 1135-1146.

Tsurushita et al., "Humanization of monoclonal antibodies," *Molecular B Cells*, (2004) 533-545.

Umana et al., "Engineered glycoforms of an antineuro-blastoma IgG1 with optimized antibody-dependent cellular cytotoxic activity," *Nature*, 17 (1999) 176-180.

Van Loghem et al., "Allotypic makers," *Monogr. Allergy*, 19 (1986) 40-51.

Verhoeyen et al., "Reshaping human antibodies: Grafting an antilysozyme activity," *Science*, 239:4847 (1988) 1534-1536.

Veri et al., "Monoclonal antibodies capable of discriminating the human inhibitory Fc gamma-receptor IIB (CD32B) from the activating Fc gamma-receptor IIA (CD32A): biochemical, biological, and functional characterization," *Immunology*, 121:3 (2007) 392-404.

Vonderhei De et al., "Clinical Activity and Immune Modulation in Cancer Patients Treated With CP-870,893, a Novel CD40 Agonist Monoclonal Antibody", *J. Clin. Oncol.*, 25:7 (2007) 876-883.

Weng et al., "Two immunoglobulin G fragment C receptor polymorphisms independently predict response to rituximab in patients with follicular lymphoma," *J. Clin. Oncol.*, 21 (2003) 3940-3947.

Wernersson et al., "IGG-mediated enhancement of antibody responses is low in Fc receptor gamma chain-deficient deficient mice and increased in FcγRII-deficient mice," *J. Immunol.*, 163:2 (1999) 618-622.

Wilman, "Prodrugs in cancer chemotherapy," *Biochemical Society Transactions*, (1986) 375-382.

Wright et al., "Effect of glycosylation on antibody function: Implications for genetic engineering," *Trends in Biotechnology*, 15:1 (1997) 23-32.

(56) References Cited

OTHER PUBLICATIONS

Yamane-Ohnuki et al., "Establishment of FUT8 knockout Chinese hamster ovary cells: an ideal host cell line for producing completely defucosylated antibodies with enhanced antibody-dependent cellular cytotoxicity," *Wiley InterScience*, 87:5 (2004) 614-622.
Yazawa et al., "Immunotherapy using unconjugated CD19 monoclonal antibodies in animal models for B lymphocyte malignancies and autoimmune disease," *PNAS*, 102:42 (2005) 15178-15183.
Yoshida et al., "Human neonatal Fc receptor mediates transport of IgG into luminal secretions for delivery of antigens to mucosal dendritic cells," *Immunity*, 20 (2004) 769-783.
Yuasa et al., "Deletion of FcGamma receptor IIB renders H-2B mice susceptible to collagen-induced arthritis," *J. Exp. Med.*, 189:1 (1999) 187-194.
Zhang et al., "A new strategy for the synthesis of glycoproteins," *Science*, 303 (2004) 371-373.
Zhukovsky et al., "XmaB 5574: an FC engineered anti CD-19 monoclonal antibody with in vitro and in vivo efficacy against Lymphoma and Leukemia," *Internet*, www.Xencor.com/downloads/aarc-sandiego-april-12-16-2008.pdf.
Restriction Requirement of Aug. 2, 2010, U.S. Appl. No. 12/156,183, 8 pages.
Examiner Interview Summary of Aug. 24, 2010, U.S. Appl. No. 12/156,183, filed May 30, 2008, 3 pages.
Amendment and Response to Restriction Requirement of Sep. 2, 2010, U.S. Appl. No. 12/156,183, filed May 30, 2008, 8 pages.
Non-Final Office Action of Oct. 4, 2010, U.S. Appl. No. 12/156,183, filed May 30, 2008, 15 pages.
Examiner Interview Summary of Jan. 20, 2011, U.S. Appl. No. 12/156,183, filed May 30, 2008, 3 pages.
Amendment and Response to Non-Final Office Action of Apr. 4, 2011, U.S. Appl. No. 12/156,183, filed May 30, 2008, 9 pages.
Notice of Allowance and Examiner Interview Summary of Jun. 28, 2011, U.S. Appl. No. 12/156,183, filed May 30, 2008, 8 pages.
Issue Notification of Nov. 2, 2011, U.S. Appl. No. 12/156,183, filed May 30, 2008, 1 page.
Non-Final Office Action of Sep. 3, 2010, U.S. Appl. No. 12/156,184, filed May 30, 2008, 16 pages.
Amendment and Response to Non-Final Office Action of Mar. 3, 2011, U.S. Appl. No. 12/156,184, filed May 30, 2008, 8 pages.
Final Office Action of Apr. 12, 2011, U.S. Appl. No. 12/156,184, filed May 30, 2008, 12 pages.
Notice of Abandonment of Oct. 28, 2011, U.S. Appl. No. 12/156,184, filed May 30, 2008, 2 pages.
Restriction Requirement of Apr. 30, 2012, U.S. Appl. No. 13/301,627, 8 pages.
Amendment and Response to Restriction Requirement of Jul. 30, 2012, U.S. Appl. No. 13/301,627, 7 pages.
Non-Final Office Action of Aug. 30, 2012, U.S. Appl. No. 13/301,627, 16 pages.
Ramsland et al., "Structural Basis for FcγRIIa Recognition of Human IgG and Formation of Inflammatory Signaling Complexes," J. Immunol., 187 (2011) 3208-3217.
Sarmay et al., "Integration of activatory and inhibitory signals in human B-cells," Immunology Letters 54 (1996) 93-100.
Written Opinion of the International Searching Authority, PCT/US2008/06915, dated Dec. 1, 2009, 7 pages.
Restriction Requirement of May 11, 2012, U.S. Appl. No. 13/294,103, 9 pages.
Amendment and Response to Restriction Requirement dated Aug. 10, 2012, U.S. Appl. No. 13/294,103, 10 pages.
Non-Final Office Action of Aug. 30, 2012, U.S. Appl. No. 13/294,103, 18 pages.
Amendment and Response to Non-Final Office Action of Aug. 30, 2012, U.S. Appl. No. 13/294,103, filed Nov. 30, 2012, 18 pages.
Final Office Action of Feb. 11, 2013, U.S. Appl. No. 13/294,103, 23 pages.
Notice of Appeal of Aug. 12, 2013, U.S. Appl. No. 13/294,103, 1 page.
Amendment and Response to Non-Final Office Action of Aug. 30, 2012, U.S. Appl. No. 13/301,627, 21 pages.
Final Office Action of Apr. 9, 2013, U.S. Appl. No. 13/301,627, 20 pages.
Amendment and Response to Final Office Action filed with RCE, Sep. 9, 2013, U.S. Appl. No. 13/301,627, 19 pages.
Lazar declaration, Dec. 27, 2010, pp. 1-4.
Lapusan et al. Invest New Drugs (2012) 30:1121-1131.
White et al., "Interaction with FcγRIIB is Critical for the Agonistic Activity of Anti-CD40 Monoclonal Antibody," Journal of Immunology (2011), 187, pp. 1-10.
Li et al., "Inhibitory Fcγ Receptor Engagement Drives Adjuvant and Anti-Tumor Activities of Agonistic CD40 Antibodies," Science (2011), vol. 333, pp. 1030-1034.

\* cited by examiner

| Allotype | Allotype | Position | | |
|---|---|---|---|---|
| | | 214 | 356 358 | 431 |
| G1m(1,17) | G1m(a,z) | K | D L | A |
| G1m(1,2,17) | G1m(a,x,z) | K | D L | G |
| G1m(3) | G1m(f) | R | E M | A |
| G1m(1,3) | G1m(a,f) | R | D L | A |

Figure 2B

| Allotype | Allotype | Position |
|---|---|---|
| | | 282 |
| G2m(23) | G2m(n+) | V |
| | G2m(n-) | M |

Figure 4

| FcγR positions contributing to FcγRIIb:FcγRIIIa binding selectivity | | | | | |
|---|---|---|---|---|---|
| Position | human FcγRIIb | human FcγRIIIa(V) | Position | human FcγRIIb | human FcγRIIIa(V) |
| 116 | V | H | 113 | K | T |
| 154 | N | L | 152 | T | R |
| 159 | L | N | 158 | T | K |
| 86 | E | G | 112 | D | N |
| 157 | Y | S | 126 | S | G |
| 132 | S | H | 19 | E | K |
| 130 | S | F | 129 | F | Y |
| 114 | P | A | 127 | K | R |
| 131 | R | H | 18 | Q | E |
| 134 | P | S | 60 | N | V |
| 160 | Y | V | 150 | H | F |
| 85 | S | I | 59 | N | T |

Figure 5

| IgG positions contributing to FcγRIIb:FcγRIIIa binding selectivity | | | | | | | | |
|---|---|---|---|---|---|---|---|---|
| Position | IgG1 | IgG2 | IgG3 | IgG4 | Position | IgG1 | IgG2 | IgG3 | IgG4 |
| 236 | G | - | G | G | 269 | E | E | E | E |
| 237 | G | G | G | G | 266 | V | V | V | V |
| 235 | L | A | L | L | 332 | I | I | I | I |
| 329 | P | P | P | P | 325 | N | N | N | N |
| 298 | S | S | S | S | 270 | D | D | D | D |
| 239 | S | S | S | S | 268 | H | H | H | Q |
| 265 | D | D | D | D | 326 | K | K | K | K |
| 327 | A | G | A | G | 331 | P | P | P | S |
| 330 | A | A | A | S | 264 | V | V | V | V |
| 297 | N | N | N | N | 233 | E | P | E | E |
| 267 | S | S | S | S | 240 | V | V | V | V |
| 234 | L | V | L | F | 241 | F | F | F | F |
| 238 | P | P | P | P | 263 | V | V | V | V |
| 299 | T | T | T | T | 300 | Y | F | F | Y |
| 328 | L | L | L | L | | | | | |

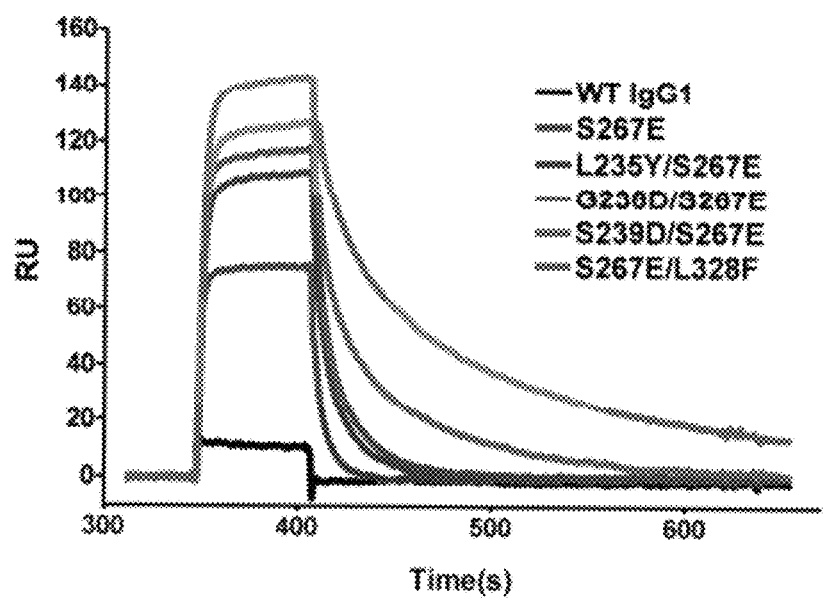

Figure 7A

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| IgG1 WT | 329 | 646 | 859 | 1467 | 191 | 1352 |
| L234D/G236N/S267E | | | 1180 | 287 | | |
| L234D/S267E | 11500 | | 67.7 | 67.8 | 1370 | |
| L234E/H268D | | | | 249 | | |
| L234E/S267E | 2510 | n.d. | 80.4 | 97 | n.d. | |
| L234E/S267E/L328F | 7750 | 8920 | 4.93 | 7.53 | n.d. | |
| L234F | 9110 | n.d. | 3760 | 3590 | n.d. | |
| L234F/G236N | | | n.d. | n.d. | | |
| L234F/S236D | | | n.d. | n.d. | | |
| L234F/S267E | 498 | 1270 | 41.6 | 55.7 | 2040 | |
| L234G | | | 10000 | 10000 | | |
| L234I | | | 15500 | 13600 | | |
| L234K | | | 100000 | 100000 | | |
| L234N | | | n.d. | n.d. | | |
| L234P | | | 60700 | 22800 | | |
| L234Q | | | 23100 | 10000 | | |
| L234S | | | 1240 | 7640 | | |
| L234V | | | 6425 | 3221 | | |
| L234W | 10500 | 1160 | 1897 | 1771 | 6590 | |
| L234W/G236D/S239E/S267E | | | 151 | 129 | | |
| L234W/H268D/L328Y | | | | 248 | | |
| L234W/L328Y/I332E | | | | 232 | | |
| L234W/S239D/L328Y | | | | 44.8 | | |
| L234W/S239E/S267E | | | 8.72 | 34.7 | | |
| L234Y | | | 16800 | 61900 | | |
| L235A | 18400 | 13300 | 5178 | 4183 | 609 | |
| L235D/S239D | | | | 357 | | |
| L235D/S267E | 854000 | n.d. | 66.1 | 88.1 | n.d. | |
| L235D/S267E/L328F | 573000 | 2350 | 6.45 | 18.2 | n.d. | |
| L235E | | | 2580 | 2668 | | |
| L235F/H268D/L328Y | | | | 370 | | |
| L235F/L328Y/I332E | | | | 443 | | |
| L235F/S239D/L328Y | | | | 215 | | |
| L235F/S267E | 18700 | 1610 | 26.4 | 51.7 | n.d. | |
| L235H | | | 1136 | 1998 | | |
| L235I | 16700 | 3580 | 1289 | 1615 | 212 | |
| L235N | | | 24100 | 10000 | | |
| L235P | | | 7013 | 251022 | | |
| L235Q | | | 420 | n.d. | | |
| L235R | | | 838 | 263 | | |
| L235S | | | 100000 | 100000 | | |
| L235S/S267E | | | 1200 | 37800 | | |

Figure 7B

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| L235T/S267E | | | 281 | 619 | | |
| L235W | | | n.d. | n.d. | | |
| L235Y | 142000 | 479 | 669 | 1400 | 380 | |
| L235Y/G236D/S267E | n.d. | n.d. | 88.8 | 56.7 | n.d. | |
| L235Y/S239D/S267E | 307 | 617 | 8.68 | 12.6 | 73.5 | |
| L235Y/S267D | | | | 92.2 | | |
| L235Y/S267E | 95000 | 687 | 22.9 | 39.4 | n.d. | |
| L235Y/S267E/H268E | 32100 | 4130 | 17.8 | 21 | 447 | |
| L235Y/S267E/L328F | 75539 | 853 | 5.02 | 7.83 | n.d. | |
| G236A/G237A | | | | 25400 | | |
| G236D | 15631 | 3871 | 1133 | 953 | n.d. | n.d. |
| G236D/H268D | | | | 126 | | |
| G236D/S239D/S267E | 4810 | 2980 | 32.2 | 17.3 | n.d. | |
| G236D/S267E | 3705 | 2728 | 34.0 | 26.6 | 579 | n.d. |
| G236D/S267E/H268E | 3650 | 6300 | 28.7 | 13.4 | n.d. | |
| G236D/S267E/L328F | 4478 | 21500 | 14.3 | 9.87 | n.d. | |
| G236E/S267E | | | 23.5 | 129 | | |
| G236F | | | 100000 | 100000 | | |
| G236H | | | 6350 | n.d. | | |
| G236I | | | n.d. | n.d. | | |
| G236K | | | 100000 | 100000 | | |
| G236L | | | n.d. | n.d. | | |
| G236M | | | 10000 | 10000 | | |
| G236N/S267E | 9270 | n.d. | 263 | 74.2 | n.d. | |
| G236P | | | 10000 | 10000 | | |
| G236Q | | | 10000 | 10000 | | |
| G236R | | | 100000 | 100000 | | |
| G236S | 12300 | 172 | 369 | 1441 | 52200 | |
| G236S/G237A | | | | 18400 | | |
| G236T | 21000 | 1330 | 2456 | 651920 | n.d. | |
| G236V | | | 8060 | 100000 | | |
| G236W | | | 10000 | 10000 | | |
| G236Y | | | n.d. | n.d. | | |
| G237A | 30500 | n.d. | 1220 | 7676 | n.d. | |
| G237D/S267E | 3770 | n.d. | 63.1 | 86.1 | n.d. | |
| G237E | | | 100000 | 100000 | | |
| G237H | | | n.d. | n.d. | | |
| G237K | | | 100000 | 100000 | | |
| G237L | | | n.d. | n.d. | | |
| G237N/S267E | 3250 | | 14 | 36.2 | n.d. | |
| G237P | | | 100000 | 100000 | | |
| G237Q | | | 10000 | 10000 | | |
| G237S | | | 10600 | 10000 | | |
| G237V | | | 25100 | 10000 | | |
| G237Y | | | 952 | 4450 | | |

Figure 7C

| Substitution(s) | FcyRI Kd (pM) | FcyRIIaH Kd (nM) | FcyRIIaR Kd (nM) | FcyRIIb Kd (nM) | FcyRIIIaV Kd (nM) | FcyRIIIaF Kd (nM) |
|---|---|---|---|---|---|---|
| S239D | 93.4 | 590 | 230 | 408 | 23.5 | 214 |
| S239D/A327D/L328Y | | | | 123 | | |
| S239D/H268D | | | | 102 | | |
| S239D/H268D/L328F | | | | 167 | | |
| S239D/H268D/L328F/I332E | | | | 27.6 | | |
| S239D/H268D/L328W | | | | 28.7 | | |
| S239D/H268D/L328W/I332E | | | | 52.7 | | |
| S239D/H268D/L328Y | | | | 60.1 | | |
| S239D/H268D/L328Y/I332E | | | | 27.1 | | |
| S239D/H268E/L328Y | | | | 67.7 | | |
| S239D/I332E | 37.4 | 163 | 68.6 | 101 | 7.07 | 28.2 |
| S239D/K326D/L328Y | | | | 113 | | |
| S239D/L328F/I332E | | | | 176 | | |
| S239D/L328Y | | | | 264 | | |
| S239D/L328Y/I332E | | | | 198 | | |
| S239D/S267A/L328Y | | | | 74.1 | | |
| S239D/S267D | | | | 65.9 | | |
| S239D/S267E | 14.2 | 510 | 7.16 | 13.3 | 51.2 | 516 |
| S239D/S267E/H268E | 326 | 817 | 7.52 | 6.91 | 18.6 | |
| S239D/S267E/I332E | | | | 11.8 | | |
| S239D/S267E/L328F | 227 | 378 | 2.06 | 3.43 | 687 | |
| S239E | 200 | 1320 | 1249 | 1828 | 54.8 | |
| S239N | | | 990 | 1013 | | |
| S239Q | | | 1007 | 2012 | | |
| D265E | | | 2794 | 3517 | | |
| V266D | | | 1220 | 10000 | | |
| V266I | | | n.d. | n.d. | | |
| V266M | 264 | 553 | 274 | 770 | 350 | |
| V266M/S267E | 166 | 59.2 | 28 | 50.2 | 4270 | |
| S267A | 287 | 530 | 200 | 408 | 201 | |
| S267A/H268D/L328Y | | | | 137 | | |
| S267A/L328Y/I332E | | | | 109 | | |
| S267D | 156 | 695 | 95.5 | 330 | 127 | |
| S267D/A327D | | | | 213 | | |
| S267D/A327E | | | | 121 | | |
| S267D/H268D | | | | 103 | | |
| S267D/H268E | | | | 82.6 | | |
| S267E | 117 | 859 | 29.1 | 71.9 | 503 | n.d. |
| S267E/A327D | 198 | | 51.3 | 69.1 | 96300 | |
| S267E/A327E | 143 | 243 | 29.3 | 47.5 | 21400 | |
| S267E/H268D | | | | 44 | | |
| S267E/H268E | 93.5 | 845 | 20.6 | 36.1 | 60.8 | |
| S267E/H268E/L328F | 333 | 763 | 3.4 | 4.26 | 2080 | |
| S267E/L328F | 220 | 923 | 3.12 | 6.06 | 5040 | n.d. |
| S267E/L328H | | | 185 | 284 | | |

Figure 7D

| Substitution(s) | FcγRI Kd (pM) | FcγRIIaH Kd (nM) | FcγRIIaR Kd (nM) | FcγRIIb Kd (nM) | FcγRIIIaV Kd (nM) | FcγRIIIaF Kd (nM) |
|---|---|---|---|---|---|---|
| S267E/L328I | | | 11.6 | 27.5 | | |
| S267E/L328Q | | | | 121 | | |
| S267E/L328Y | 1470 | 481 | 7.06 | 34.1 | n.d. | |
| S267E/N325L | | | 20.7 | 46.6 | | |
| S267G | 626 | 2120 | 517 | 1450 | 2120 | |
| H268D | 140 | 342 | 205 | 480 | 62.2 | |
| H268D/A327D | | | | 191 | | |
| H268D/A327D/L328Y | | | | 420 | | |
| H268D/K326D/L328Y | | | | 78.9 | | |
| H268D/L328F/I332E | | | | 119 | | |
| H268D/L328W/I332E | | | | 36.9 | | |
| H268D/L328Y | | | | 767 | | |
| H268D/L328Y/I332E | | | | 300 | | |
| H268E | 120 | 453 | 269 | 560 | 87.5 | |
| H268E/L328Y/I332E | | | | 172 | | |
| H268N | | | 481 | 1250 | | |
| H268Q | | | 544 | n.d. | | |
| S298D | | | 592 | 1840 | | |
| S298E | | | n.d. | n.d. | | |
| S298L | | | | n.d. | | |
| S298M | | | | n.d. | | |
| S298Q | | | n.d. | n.d. | | |
| K326A | | | | n.d. | | |
| K326D/L328Y/I332E | | | | 553 | | |
| K326E | | | | 241 | | |
| K326W | | | | 483 | | |
| A327D | 160 | 882 | 536 | 1100 | 481 | |
| A327D/L328Y/I332E | | | | 636 | | |
| A327G | | | 2692 | 4159 | | |
| A327L | | | | n.d. | | |
| A327N | 11800 | n.d. | 1410 | 1740 | n.d. | |
| A327Q | | | 1354 | 133661 | | |
| L328E | | | | n.d. | | |
| L328F | 452 | 2360 | 166 | 541 | 58408 | 5109 |
| L328Y/I332E | | | | 705 | | |
| P329E | | | 10000 | 10000 | | |
| A330D | | | | n.d. | | |
| A330H | | | | n.d. | | |
| A330K | | | | 947 | | |
| A330S | | | | 23100 | | |
| P331S | | | | 39400 | | |
| IgG1/2ELLGG | 161 | 428 | 481 | 563 | 667 | |
| IgG1/2ELLGG_S267E/L328F | 140 | 651 | 3.19 | 6.63 | n.d. | |
| G236R/L328R | n.d. | n.d. | n.d. | n.d. | n.d. | n.d. |
| ^236R/L328R | n.d. | n.d. | n.d. | n.d. | n.d. | n.d. |

Figure 8A

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| IgG1 WT | 1 | 1 | 1 | 1 | 1 | 1 |
| L234D/G236N/S267E | | | 0.728 | 5.11 | | |
| L234D/S267E | 0.0286 | | 12.7 | 21.7 | 0.14 | |
| L234E/H268D | | | | 5.89 | | |
| L234E/S267E | 0.131 | n.d. | 10.7 | 15.1 | n.d. | |
| L234E/S267E/L328F | 0.0425 | 0.0725 | 174 | 195 | n.d. | |
| L234F | 0.0362 | n.d. | 0.228 | 0.409 | n.d. | |
| L234F/G236N | | | n.d. | n.d. | | |
| L234F/S236D | | | n.d. | n.d. | | |
| L234F/S267E | 0.661 | 0.509 | 20.7 | 28.4 | 0.0938 | |
| L234G | | | 0.0859 | 0.147 | | |
| L234I | | | 0.0554 | 0.108 | | |
| L234K | | | 0.00859 | 0.0147 | | |
| L234N | | | n.d. | n.d. | | |
| L234P | | | 0.0141 | 0.0644 | | |
| L234Q | | | 0.0372 | 0.147 | | |
| L234S | | | 0.693 | 0.192 | | |
| L234V | | | 0.134 | 0.456 | | |
| L234W | 0.0314 | 0.557 | 0.453 | 0.829 | 0.029 | |
| L234W/G236D/S239E/S267E | | | 5.69 | 11.4 | | |
| L234W/H268D/L328Y | | | | 5.92 | | |
| L234W/L328Y/I332E | | | | 6.32 | | |
| L234W/S239D/L328Y | | | | 32.8 | | |
| L234W/S239E/S267E | | | 98.5 | 42.3 | | |
| L234Y | | | 0.0511 | 0.0837 | | |
| L235A | 0.0179 | 0.0486 | 0.166 | 0.351 | 0.314 | |
| L235D/S239D | | | | 4.11 | | |
| L235D/S267E | 0.00039 | n.d. | 13 | 16.7 | n.d. | |
| L235D/S267E/L328F | 0.00057 | 0.275 | 133 | 80.4 | n.d. | |
| L235E | | | 0.333 | 0.55 | | |
| L235F/H268D/L328Y | | | | 3.97 | | |
| L235F/L328Y/I332E | | | | 3.31 | | |
| L235F/S239D/L328Y | | | | 6.82 | | |
| L235F/S267E | 0.0176 | 0.402 | 32.5 | 28.4 | n.d. | |
| L235H | | | 0.756 | 0.734 | | |
| L235I | 0.0197 | 0.181 | 0.666 | 0.908 | 0.903 | |
| L235N | | | 0.0356 | 0.147 | | |
| L235P | | | 0.122 | 0.00585 | | |
| L235Q | | | 2.04 | n.d. | | |
| L235R | | | 1.02 | 5.58 | | |
| L235S | | | 0.00859 | 0.0147 | | |
| L235S/S267E | | | 0.716 | 0.0388 | | |
| L235T/S267E | | | 3.06 | 2.37 | | |

Figure 8B

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| L235W | | | n.d. | n.d. | | |
| L235Y | 0.00232 | 1.35 | 1.28 | 1.05 | 0.504 | |
| L235Y/G236D/S267E | n.d. | n.d. | 9.67 | 26 | n.d. | |
| L235Y/S239D/S267E | 1.07 | 1.05 | 98.9 | 116 | 2.6 | |
| L235Y/S267D | | | | 15.9 | | |
| L235Y/S267E | 0.00347 | 0.941 | 37.5 | 37.2 | n.d. | |
| L235Y/S267E/H268E | 0.0103 | 0.157 | 48.2 | 69.9 | 0.428 | |
| L235Y/S267E/L328F | 0.00436 | 0.758 | 171 | 187 | n.d. | |
| G236A/G237A | | | | 0.0578 | | |
| G236D | 0.0211 | 0.167 | 0.758 | 1.54 | n.d. | n.d. |
| G236D/H268D | | | | 11.6 | | |
| G236D/S239D/S267E | 0.0685 | 0.217 | 26.7 | 84.8 | n.d. | |
| G236D/S267E | 0.0889 | 0.237 | 25.2 | 55.1 | 0.331 | n.d. |
| G236D/S267E/H268E | 0.0902 | 0.103 | 29.9 | 110 | n.d. | |
| G236D/S267E/L328F | 0.0736 | 0.0301 | 59.9 | 149 | n.d. | |
| G236E/S267E | | | 36.5 | 11.4 | | |
| G236F | | | 0.00859 | 0.0147 | | |
| G236H | | | 0.135 | n.d. | | |
| G236I | | | n.d. | n.d. | | |
| G236K | | | 0.00859 | 0.0147 | | |
| G236L | | | n.d. | n.d. | | |
| G236M | | | 0.0859 | 0.147 | | |
| G236N/S267E | 0.0365 | n.d. | 3.27 | 19.8 | n.d. | |
| G236P | | | 0.0859 | 0.147 | | |
| G236Q | | | 0.0859 | 0.147 | | |
| G236R | | | 0.00859 | 0.0147 | | |
| G236S | 0.0268 | 3.76 | 2.33 | 1.02 | 0.00367 | |
| G236S/G237A | | | | 0.0797 | | |
| G236T | 0.0157 | 0.486 | 0.35 | 0.00225 | n.d. | |
| G236V | | | 0.106 | 0.0147 | | |
| G236W | | | 0.0859 | 0.147 | | |
| G236Y | | | n.d. | n.d. | | |
| G237A | 0.0108 | n.d. | 0.704 | 0.191 | n.d. | |
| G237D/S267E | 0.0874 | n.d. | 13.6 | 17 | n.d. | |
| G237E | | | 0.00859 | 0.0147 | | |
| G237H | | | n.d. | n.d. | | |
| G237K | | | 0.00859 | 0.0147 | | |
| G237L | | | n.d. | n.d. | | |
| G237N/S267E | 0.101 | | 61.5 | 40.5 | n.d. | |
| G237P | | | 0.00859 | 0.0147 | | |
| G237Q | | | 0.0859 | 0.147 | | |
| G237S | | | 0.081 | 0.147 | | |
| G237V | | | 0.0342 | 0.147 | | |
| G237Y | | | 0.902 | 0.33 | | |
| S239D | 3.53 | 1.1 | 3.73 | 3.6 | 8.14 | 6.32 |
| S239D/A327D/L328Y | | | | 11.9 | | |

Figure 8C

| Substitution(s) | Fold FcyRI | Fold FcyRIIaH | Fold FcyRIIaR | Fold FcyRIIb | Fold FcyRIIIaV | Fold FcyRIIIaF |
|---|---|---|---|---|---|---|
| S239D/H268D | | | | 14.4 | | |
| S239D/H268D/L328F | | | | 8.79 | | |
| S239D/H268D/L328F/I332E | | | | 53.2 | | |
| S239D/H268D/L328W | | | | 51.1 | | |
| S239D/H268D/L328W/I332E | | | | 27.8 | | |
| S239D/H268D/L328Y | | | | 24.4 | | |
| S239D/H268D/L328Y/I332E | | | | 54.1 | | |
| S239D/H268E/L328Y | | | | 21.7 | | |
| S239D/I332E | 8.81 | 3.98 | 12.6 | 14.6 | 27.1 | 48 |
| S239D/K326D/L328Y | | | | 13 | | |
| S239D/L328F/I332E | | | | 8.34 | | |
| S239D/L328Y | | | | 5.56 | | |
| S239D/L328Y/I332E | | | | 7.41 | | |
| S239D/S267A/L328Y | | | | 19.8 | | |
| S239D/S267D | | | | 22.3 | | |
| S239D/S267E | 23.2 | 1.27 | 120 | 111 | 3.74 | 2.62 |
| S239D/S267E/H268E | 1.01 | 0.791 | 114 | 212 | 10.3 | |
| S239D/S267E/I332E | | | | 124 | | |
| S239D/S267E/L328F | 1.45 | 1.71 | 416 | 428 | 0.216 | |
| S239E | 1.65 | 0.49 | 0.688 | 0.803 | 3.49 | |
| S239N | | | 0.867 | 1.45 | | |
| S239Q | | | 0.853 | 0.729 | | |
| D265E | | | 0.307 | 0.417 | | |
| V266D | | | 0.704 | 0.147 | | |
| V266I | | | n.d. | n.d. | | |
| V266M | 1.25 | 1.17 | 3.13 | 1.91 | 0.547 | |
| V266M/S267E | 1.98 | 10.9 | 30.7 | 29.2 | 0.0448 | |
| S267A | 1.15 | 1.22 | 4.29 | 3.6 | 0.952 | |
| S267A/H268D/L328Y | | | | 10.7 | | |
| S267A/L328Y/I332E | | | | 13.5 | | |
| S267D | 2.11 | 0.93 | 8.99 | 4.45 | 1.51 | |
| S267D/A327D | | | | 6.89 | | |
| S267D/A327E | | | | 12.1 | | |
| S267D/H268D | | | | 14.2 | | |
| S267D/H268E | | | | 17.8 | | |
| S267E | 2.81 | 0.753 | 29.5 | 20.4 | 0.381 | n.d. |
| S267E/A327D | 1.66 | | 16.7 | 21.2 | 0.00199 | |
| S267E/A327E | 2.3 | 2.66 | 29.3 | 30.9 | 0.00894 | |
| S267E/H268D | | | | 33.3 | | |
| S267E/H268E | 3.52 | 0.765 | 41.7 | 40.6 | 3.15 | |
| S267E/H268E/L328F | 0.991 | 0.826 | 253 | 344 | 0.092 | |
| S267E/L328F | 1.5 | 0.7 | 275 | 242 | 0.038 | n.d. |
| S267E/L328H | | | 4.64 | 5.17 | | |
| S267E/L328I | | | 74 | 53.4 | | |
| S267E/L328Q | | | | 12.1 | | |
| S267E/L328Y | 0.224 | 1.34 | 122 | 43.1 | n.d. | |
| S267E/N325L | | | 41.5 | 31.5 | | |

Figure 8D

| Substitution(s) | Fold FcγRI | Fold FcγRIIaH | Fold FcγRIIaR | Fold FcγRIIb | Fold FcγRIIIaV | Fold FcγRIIIaF |
|---|---|---|---|---|---|---|
| S267G | 0.526 | 0.305 | 1.66 | 1.01 | 0.0903 | |
| H268D | 2.35 | 1.89 | 4.19 | 3.06 | 3.08 | |
| H268D/A327D | | | | 7.68 | | |
| H268D/A327D/L328Y | | | | 3.49 | | |
| H268D/K326D/L328Y | | | | 18.6 | | |
| H268D/L328F/I332E | | | | 12.3 | | |
| H268D/L328W/I332E | | | | 39.8 | | |
| H268D/L328Y | | | | 1.91 | | |
| H268D/L328Y/I332E | | | | 4.89 | | |
| H268E | 2.74 | 1.43 | 3.19 | 2.62 | 2.19 | |
| H268E/L328Y/I332E | | | | 8.53 | | |
| H268N | | | 1.79 | 1.17 | | |
| H268Q | | | 1.58 | n.d. | | |
| S298D | | | 1.45 | 0.797 | | |
| S298E | | | n.d. | n.d. | | |
| S298L | | | | n.d. | | |
| S298M | | | | n.d. | | |
| S298Q | | | n.d. | n.d. | | |
| K326A | | | | n.d. | | |
| K326D/L328Y/I332E | | | | 2.65 | | |
| K326E | | | | 6.09 | | |
| K326W | | | | 3.04 | | |
| A327D | 2.06 | 0.733 | 1.6 | 1.33 | 0.398 | |
| A327D/L328Y/I332E | | | | 2.31 | | |
| A327G | | | 0.319 | 0.353 | | |
| A327L | | | | n.d. | | |
| A327N | 0.0279 | n.d. | 0.609 | 0.843 | n.d. | |
| A327Q | | | 0.634 | 0.011 | | |
| L328E | | | | n.d. | | |
| L328F | 0.728 | 0.274 | 5.16 | 2.71 | 0.00328 | 0.265 |
| L328Y/I332E | | | | 2.08 | | |
| P329E | | | 0.0859 | 0.147 | | |
| A330D | | | | n.d. | | |
| A330H | | | | n.d. | | |
| A330K | | | | 1.55 | | |
| A330S | | | | 0.0635 | | |
| P331S | | | | 0.0372 | | |
| IgG1/2ELLGG | 2.05 | 1.51 | 1.79 | 2.61 | 0.287 | |
| IgG1/2ELLGG_S267E/L328F | 2.35 | 0.993 | 269 | 221 | n.d. | |
| G236R/L328R | n.d. | n.d. | n.d. | n.d. | n.d. | n.d. |
| ^236R/L328R | n.d. | n.d. | n.d. | n.d. | n.d. | n.d. |

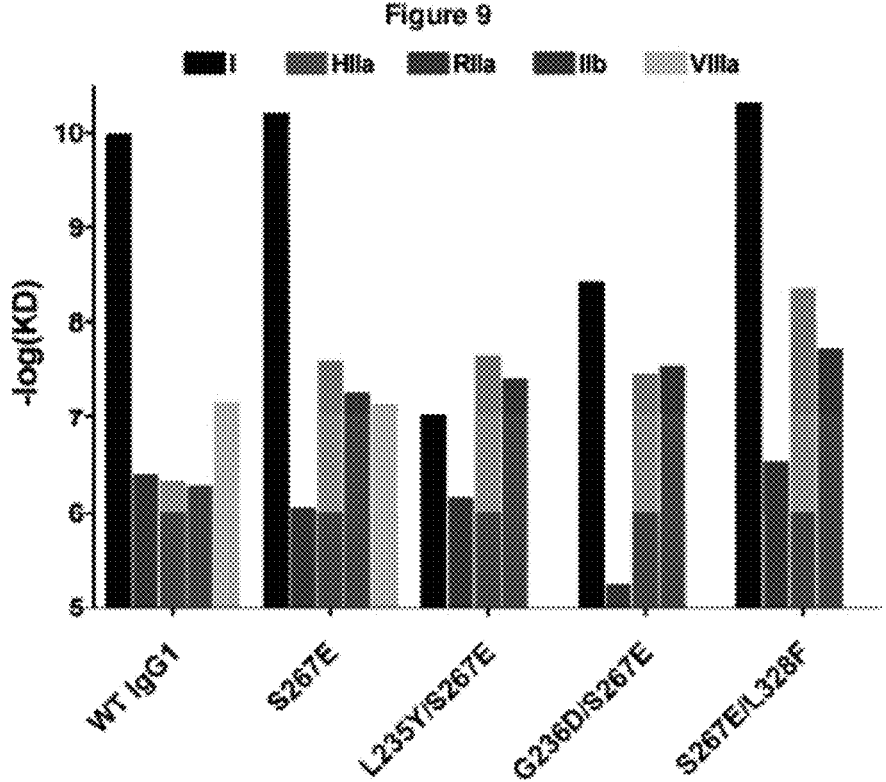
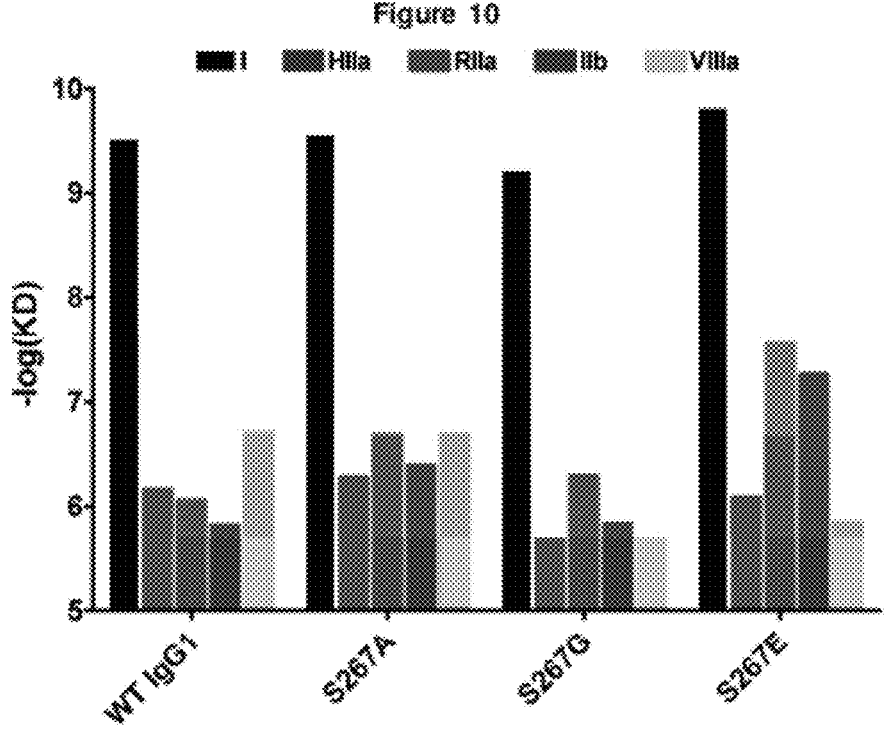

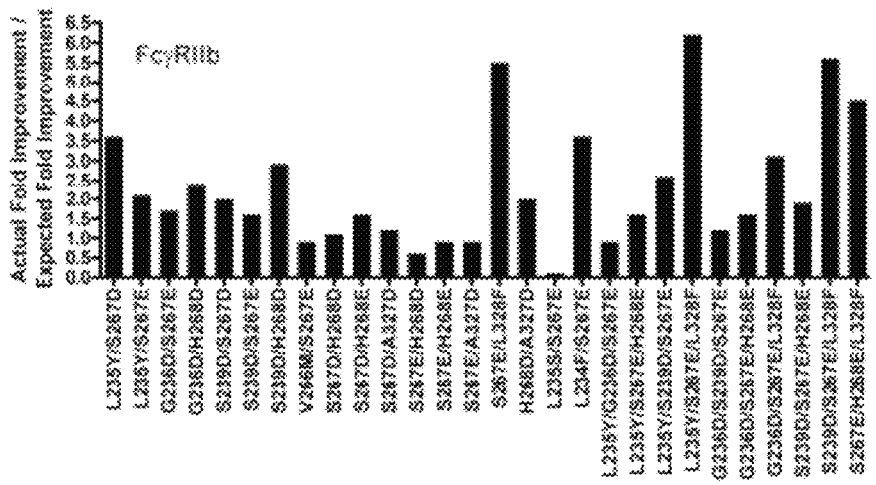
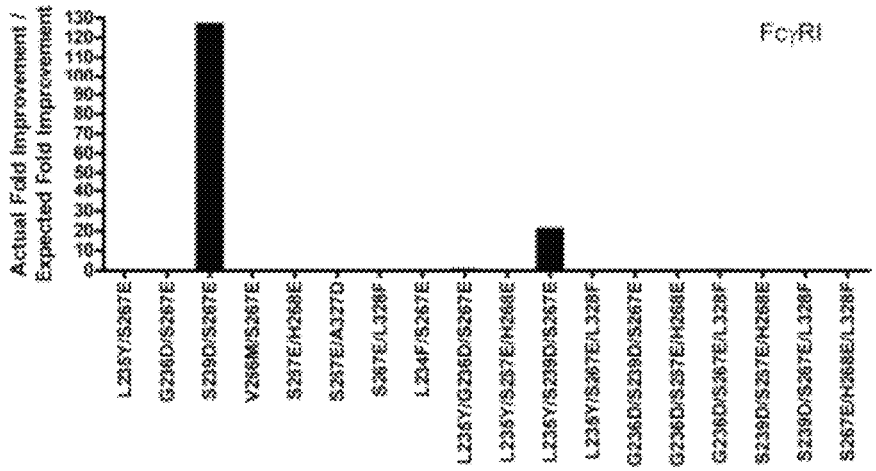

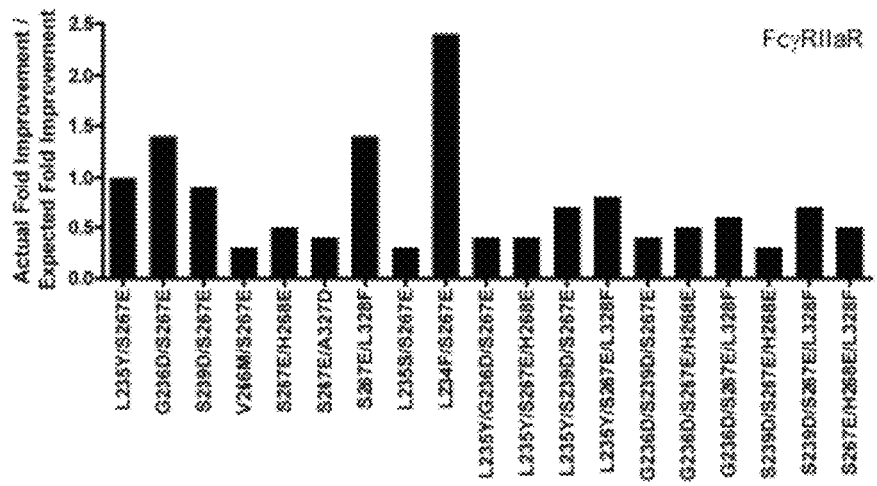
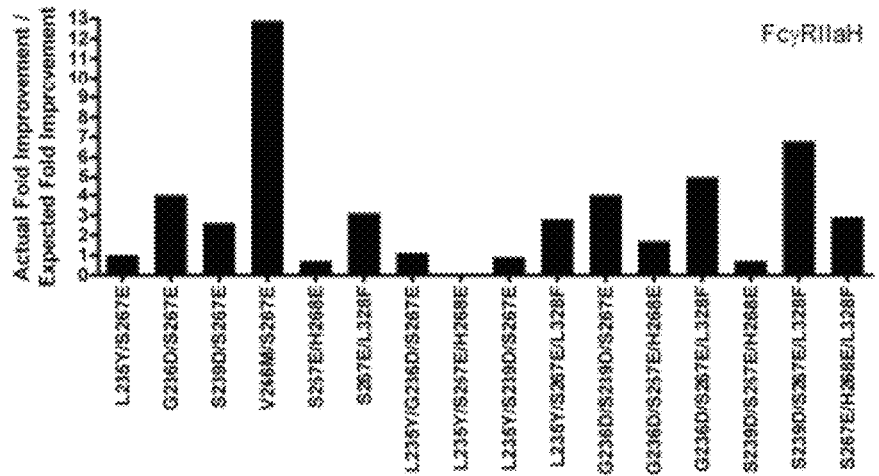

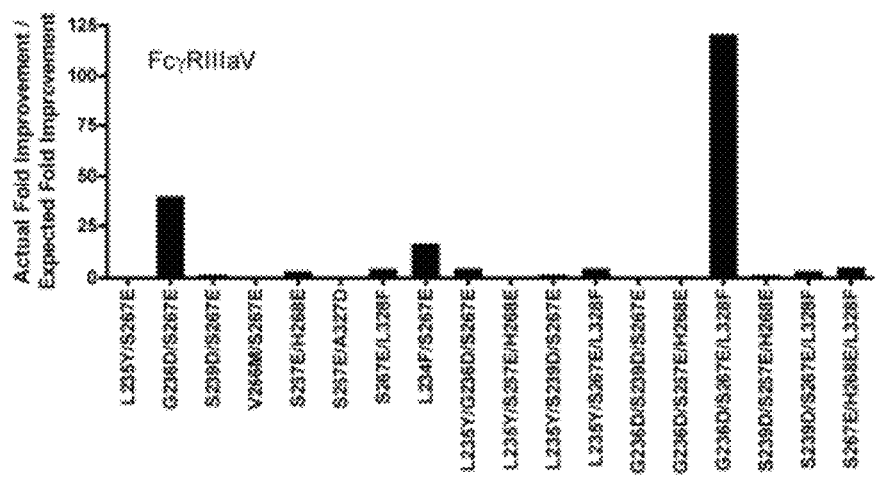

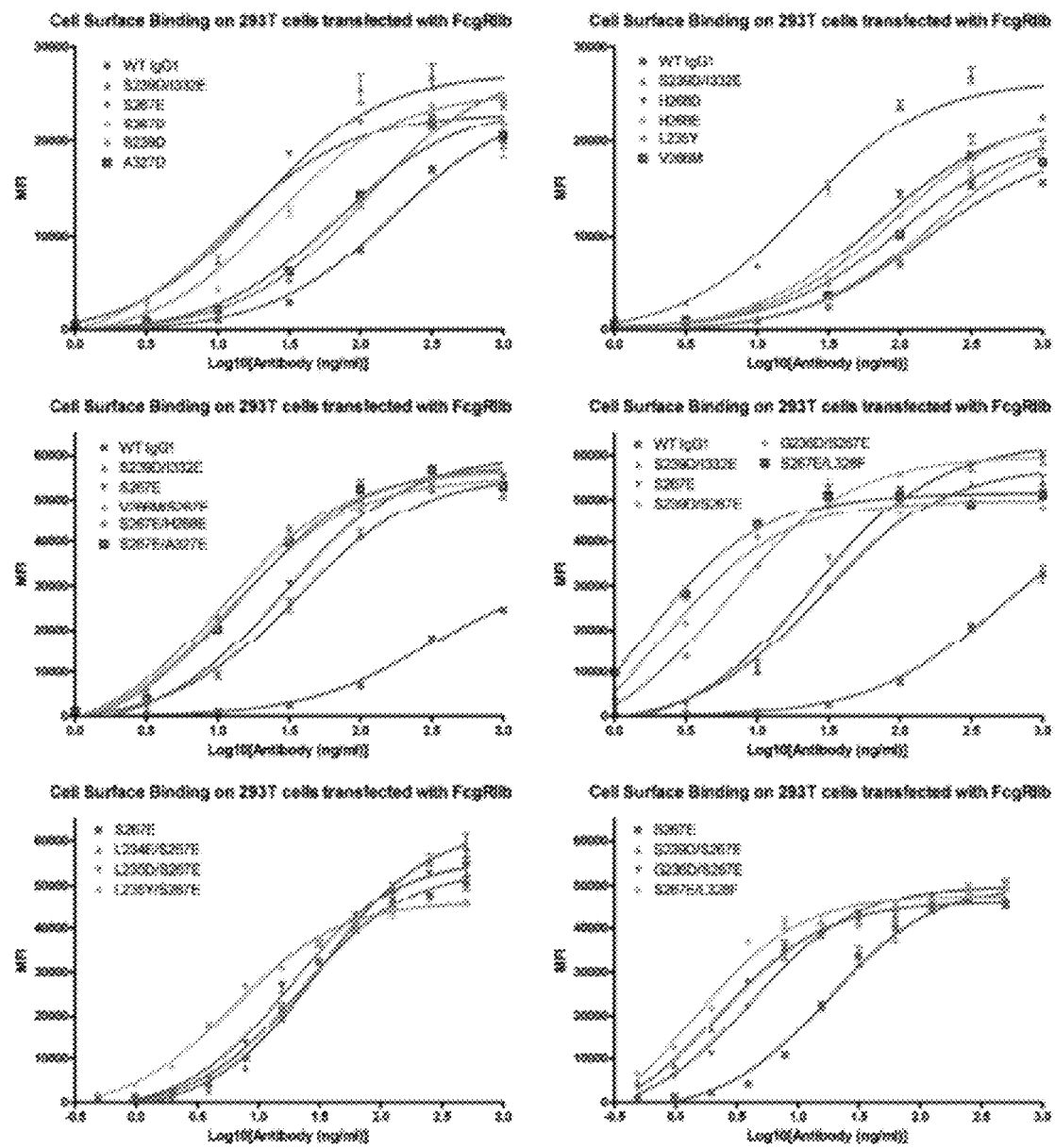

Figure 13A

| Substitution(s) | Method | mFcγRIIb Fold | mFcγRIV Fold | cynoFcγRIIb Fold | cynoFcγRIIIa Fold |
|---|---|---|---|---|---|
| L234D/G236N/S267E | Kd | NB | | NB | |
| L234D/S267E | off- | 1.041 | NB | | |
| L234D/S267E | off- | | | 0.495 | 0.116 |
| L234F | off- | NB | 0.144 | | |
| L234F | off- | | | 0.936 | 0.561 |
| L234G | off- | NB | NB | | |
| L234G | off- | | | NB | 0.113 |
| L234K | off- | NB | NB | | |
| L234K | off- | | | NB | NB |
| L234N | off- | NB | 0.200 | | |
| L234N | off- | | | NB | 0.371 |
| L234Q | off- | NB | NB | | |
| L234Q | off- | | | NB | 0.379 |
| L234W | Kd | | | 1.896 | |
| L234W/G236D/S239E/S267E | Kd | 0.029 | | NB | |
| L234W/H268D/L328Y | Kd | 5.923 | | 4.629 | |
| L234W/L328Y/I332E | Kd | 0.617 | | 2.038 | |
| L234W/S239D/L328Y | Kd | 44.110 | | 5.922 | |
| L234W/S239E/S267E | Kd | 0.761 | | 2.246 | |
| L234Y | Kd | | | 1.013 | |
| L235A | off- | NB | 0.496 | | |
| L235A | off- | | | NB | 0.530 |
| L235D/S239D | off- | | 1.571 | | 1.407 |
| L235E | off- | NB | 0.857 | | |
| L235E | off- | | | NB | 0.367 |
| L235F/H268D/L328Y | Kd | 6.822 | | 3.169 | |
| L235F/L328Y/I332E | Kd | 0.843 | | 4.109 | |
| L235F/S239D/L328Y | Kd | 31.204 | | 5.196 | |
| L235F/S267E | off- | NB | 0.515 | | |
| L235F/S267E | off- | | | 1.392 | 0.255 |
| L235H | Kd | | | 0.832 | |
| L235N | off- | NB | 0.241 | | |
| L235N | off- | | | NB | 0.351 |
| L235R | off- | NB | 0.347 | | |
| L235R | off- | | | NB | NB |
| L235W | Kd | | | 1.443 | |
| L235Y | off- | 1.022 | 0.507 | | |
| L235Y | off- | | | 0.920 | 0.535 |
| G236A/G237A | Kd | NB | | NB | |
| G236D | off- | NB | NB | | |
| G236D | off- | | | NB | NB |
| G236D/S267E | off- | NB | NB | | |
| G236D/S267E | off- | | | NB | NB |
| G236E/S267E | off- | NB | NB | | |
| G236E/S267E | off- | | | NB | 0.327 |
| G236F | off- | NB | NB | | |
| G236F | off- | | | NB | 0.138 |
| G236N/S267E | off- | NB | NB | | |

Figure 13B

| | | | | | |
|---|---|---|---|---|---|
| G236N/S267E | off- | | | 0.587 | NB |
| G236P | off- | NB | NB | | |
| G236P | off- | | | NB | NB |
| G236R | off- | NB | NB | | |
| G236R | off- | | | NB | NB |
| G236S | Kd | | | 3.549 | 1.453 |
| G236S/G237A | Kd | NB | | NB | |
| G236V | off- | NB | NB | | |
| G236V | off- | | | 0.703 | NB |
| G237A | off- | NB | NB | | |
| G237A | off- | | | NB | NB |
| G237E | off- | NB | NB | | |
| G237E | off- | | | NB | NB |
| G237H | off- | NB | NB | | |
| G237H | off- | | | NB | NB |
| G237K | off- | NB | NB | | |
| G237K | off- | | | NB | NB |
| G237S | off- | NB | NB | | |
| G237S | off- | | | NB | NB |
| S239D | Kd | 2.006 | 2.525 | 1.638 | 7.579 |
| S239D | off- | 2.912 | 1.907 | | |
| S239D | off- | | | 1.986 | 2.325 |
| S239D/A327D/L328Y | Kd | 45.296 | | 1.309 | |
| S239D/H268D | Kd | 1.857 | 1.063 | 5.683 | 8.675 |
| S239D/H268D | Kd | 1.518 | | 16.693 | |
| S239D/H268D | off- | | 2.209 | | 3.618 |
| S239D/H268D/L328F | Kd | 6.007 | | 3.169 | |
| S239D/H268D/L328F/I332E | Kd | 2.592 | | 27.604 | |
| S239D/H268D/L328W | Kd | 47.801 | | 23.740 | |
| S239D/H268D/L328W/I332E | Kd | 4.814 | | 4.549 | |
| S239D/H268D/L328Y | Kd | 48.629 | | 22.246 | |
| S239D/H268D/L328Y/I332E | Kd | 3.036 | | 9.099 | |
| S239D/H268E/L328Y | Kd | 26.535 | | 5.873 | |
| S239D/I332E | Kd | 5.442 | 7.473 | 10.196 | 11.520 |
| S239D/I332E | Kd | 1.150 | | 17.815 | |
| S239D/K326D/L328Y | Kd | 131.128 | | 10.192 | |
| S239D/L328F/I332E | Kd | 2.093 | | 3.086 | |
| S239D/L328Y | Kd | 11.463 | | 2.135 | |
| S239D/L328Y/I332E | Kd | 1.702 | | 5.121 | |
| S239D/S267A/L328Y | Kd | 46.483 | | 6.463 | |
| S239D/S267D | Kd | 1.983 | 1.005 | 1.793 | 7.660 |
| S239D/S267D | off- | | 1.875 | | 2.734 |
| S239D/S267E | Kd | 1.746 | 0.726 | 1.588 | 3.881 |
| S239D/S267E | off- | 7.871 | 1.545 | | |
| S239D/S267E | off- | | | 2.526 | 1.677 |
| S239D/S267E/I332E | Kd | 1.003 | | 10.047 | |
| S239D/S267E/L328F | Kd | | | 4.581 | 1.171 |
| S239E | off- | 3.105 | 1.925 | | |
| S239E | off- | | | 1.249 | 2.261 |
| S239N | off- | 0.610 | 1.074 | | |
| S239N | off- | | | 0.660 | 1.146 |
| S239Q | off- | 1.740 | 0.711 | | |
| S239Q | off- | | | 0.401 | 0.622 |
| D265E | off- | 0.833 | 0.526 | | |
| D265E | off- | | | 0.648 | 0.636 |
| V266D | off- | NB | NB | | |
| V266D | off- | | | NB | NB |
| V266I | off- | 1.416 | 1.193 | | |
| V266I | off- | | | 0.826 | 0.979 |

Figure 13C

| Mutation | Type | Val1 | Val2 | Val3 | Val4 |
|---|---|---|---|---|---|
| V266M | off- | 2.036 | 1.229 | | |
| V266M | off- | | | NB | 0.433 |
| S267A | off- | 3.022 | 1.534 | | |
| S267A | off- | | | 1.048 | 1.274 |
| S267A/H268D/L328Y | Kd | 32.404 | | 3.262 | |
| S267A/L328Y/I332E | Kd | 2.633 | | 3.655 | |
| S267D | off- | 1.945 | 1.267 | | |
| S267D | off- | | | 1.031 | 1.271 |
| S267D/A327D | off- | 0.000 | | 0.000 | |
| S267D/H268D | Kd | 0.902 | 0.598 | 1.860 | 5.333 |
| S267D/H268D | off- | 0.968 | | 1.956 | |
| S267E | off- | 1.437 | 0.770 | | |
| S267E | off- | | | 1.093 | 0.515 |
| S267E/A327D | off- | 0.971 | | 0.697 | |
| S267E/A327E | off- | 2.796 | 1.036 | | |
| S267E/A327E | off- | | | 1.033 | 0.465 |
| S267E/H268E/L328F | Kd | | | 3.514 | 1.043 |
| S267E/L328F | Kd | 1.060 | 0.020 | 0.881 | NB |
| S267E/L328F | off- | 4.887 | 0.198 | | |
| S267E/L328F | off- | | | 1.263 | NB |
| S267E/L328H | off- | 1.111 | NB | | |
| S267E/L328H | off- | | | 0.420 | NB |
| S267E/L328I | off- | 2.105 | 0.588 | | |
| S267E/L328I | off- | | | 0.831 | 0.437 |
| S267E/L328Q | off- | 0.881 | 0.454 | | |
| S267E/L328Q | off- | | | 0.367 | 0.124 |
| S267E/L328Y | Kd | 1.513 | 0.026 | 1.313 | NB |
| S267E/L328Y | Kd | 1.037 | | 0.404 | |
| S267E/L328Y | off- | 7.915 | NB | | |
| S267E/L328Y | off- | | | 1.934 | NB |
| S267E/N325L | off- | NB | 0.240 | | |
| S267E/N325L | off- | | | NB | NB |
| S267G | off- | NB | 0.586 | | |
| S267G | off- | | | NB | 0.343 |
| H268D | Kd | 1.111 | 0.470 | 1.475 | 4.235 |
| H268D | off- | 2.626 | 1.447 | | |
| H268D | off- | | | 3.937 | 1.653 |
| H268D/A327D | Kd | 3.220 | 0.443 | 1.467 | 1.733 |
| H268D/A327D | off- | 5.095 | | 1.797 | |
| H268D/A327D/L328Y | Kd | 18.722 | | 3.581 | |
| H268D/K326D/L328Y | Kd | 19.368 | | 9.381 | |
| H268D/L328F/I332E | Kd | 1.478 | | 4.885 | |
| H268D/L328W/I332E | Kd | 4.260 | | 7.465 | |
| H268D/L328Y | Kd | 2.785 | | 2.924 | |
| H268D/L328Y/I332E | Kd | 1.281 | | 4.085 | |
| H268E | off- | 2.443 | 1.417 | | |
| H268E | off- | | | 2.230 | 1.509 |
| H268E/L328Y/I332E | Kd | 1.498 | | 4.157 | |
| H268N | off- | 1.597 | 1.025 | | |
| H268N | off- | | | 1.345 | 0.990 |
| H268Q | off- | 0.877 | 1.085 | | |
| H268Q | off- | | | 0.864 | 0.983 |
| S298D | off- | NB | 0.618 | | |
| S298D | off- | | | NB | 0.309 |
| S298E | off- | NB | 0.136 | | |
| S298E | off- | | | NB | 0.046 |
| S298L | Kd | 0.208 | | 0.040 | |
| S298M | Kd | 0.549 | | 2.846 | |
| S298Q | off- | 1.412 | 0.291 | | |

Figure 13D

| | | | | | |
|---|---|---|---|---|---|
| S298Q | off- | | | 0.714 | 0.271 |
| K326A | Kd | 0.164 | | 1.359 | |
| K326D/L328Y/I332E | Kd | 1.872 | | 4.775 | |
| K326E | Kd | 0.605 | | 1.029 | |
| K326W | Kd | 0.429 | | 0.078 | |
| A327D | Kd | 1.857 | 0.315 | 1.156 | 0.783 |
| A327D | off- | 4.102 | 0.876 | | |
| A327D | off- | | | 1.147 | 0.515 |
| A327D/L328Y/I332E | Kd | 1.239 | | 1.019 | |
| A327G | off- | 1.452 | 1.229 | | |
| A327G | off- | | | 0.903 | 0.443 |
| A327L | Kd | NB | | NB | |
| A327N | off- | 0.643 | 1.159 | | |
| A327N | off- | | | NB | 0.313 |
| A327Q | off- | NB | 0.361 | | |
| A327Q | off- | | | NB | 0.223 |
| L328E | Kd | 0.016 | | NB | |
| L328F | off- | 3.122 | 0.261 | | |
| L328F | off- | | | 0.380 | 0.144 |
| L328Y/I332E | Kd | 0.434 | | 4.599 | |
| P329E | off- | NB | NB | | |
| P329E | off- | | | NB | NB |
| A330D | Kd | 2.633 | | NB | |
| A330H | Kd | 0.013 | | NB | |
| A330K | Kd | 0.296 | | 2.019 | |
| A330S | Kd | 0.054 | | 0.255 | |
| P331S | Kd | 0.085 | | 0.250 | |

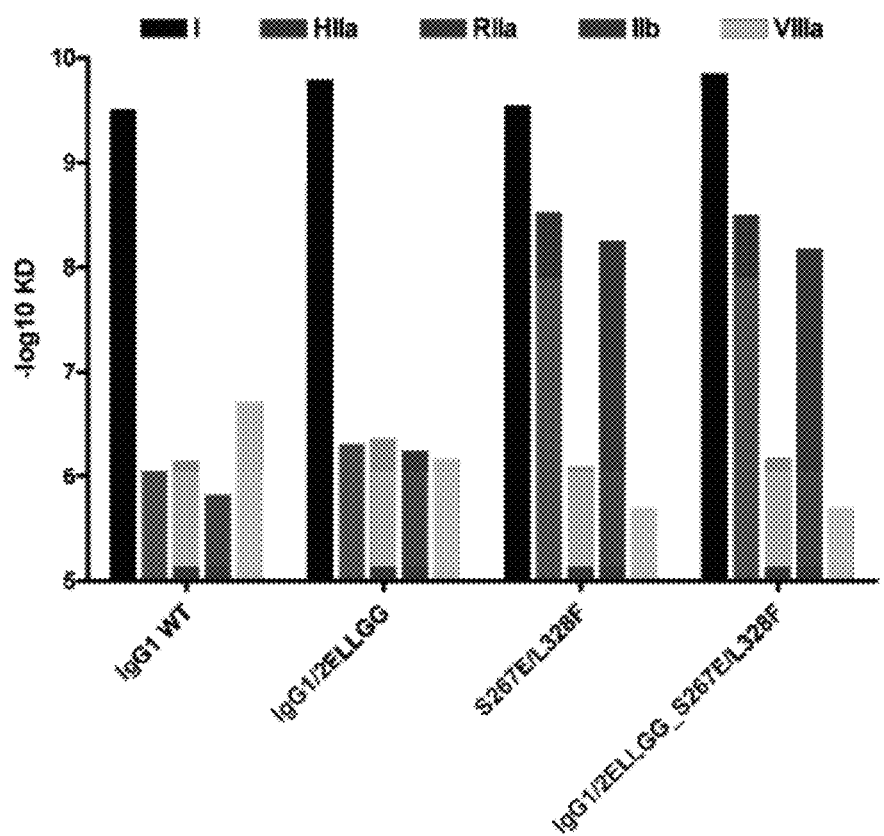

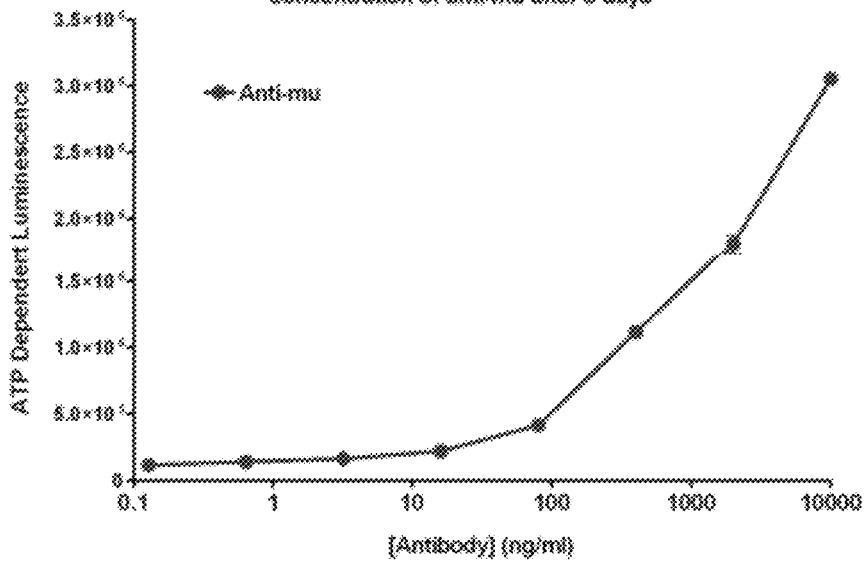
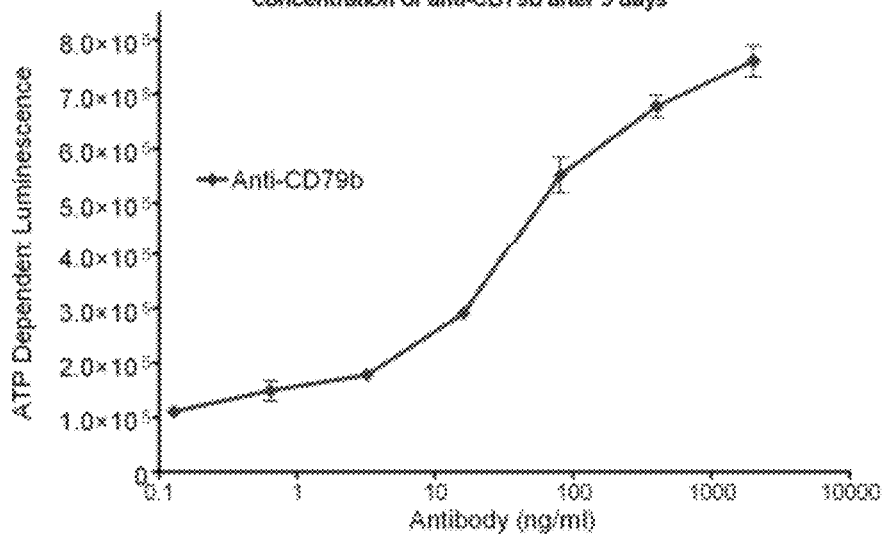

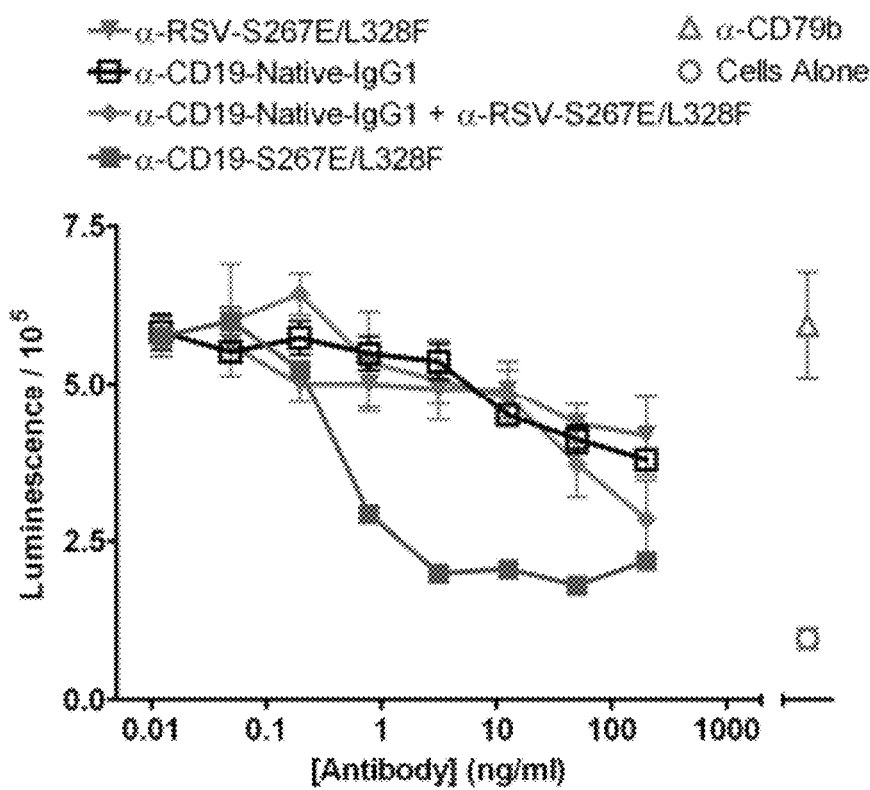

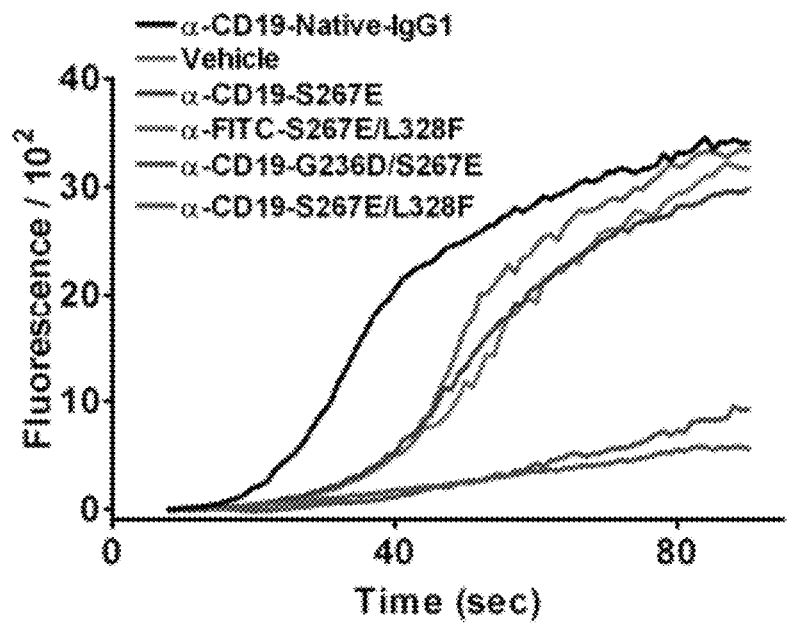
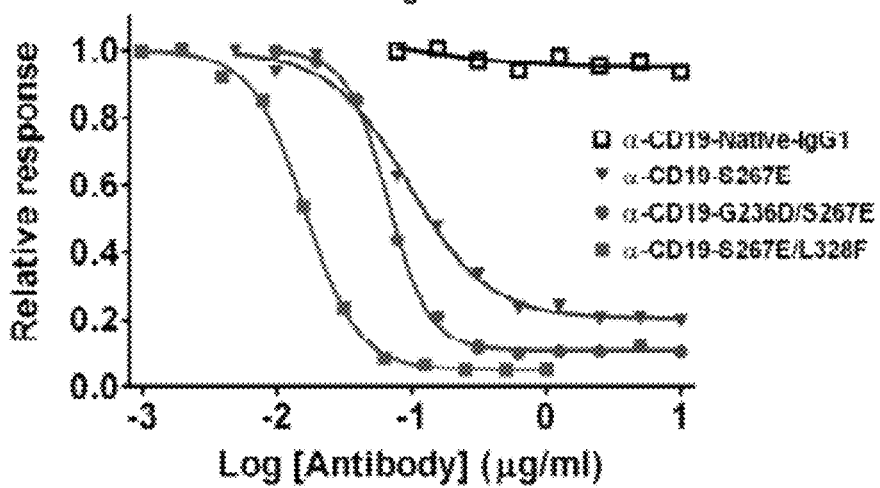

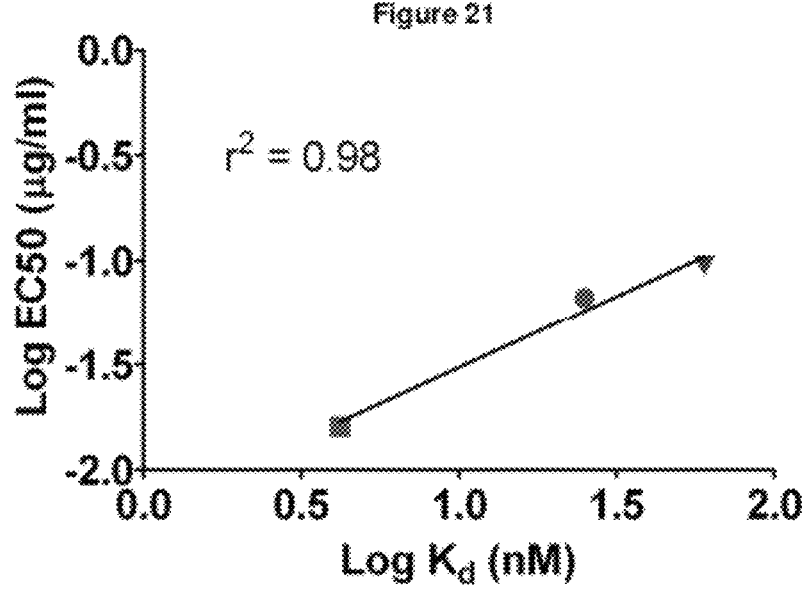
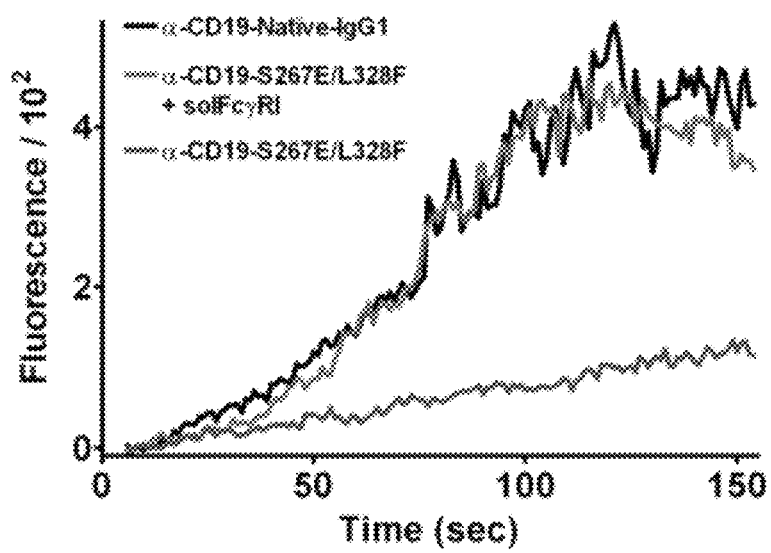

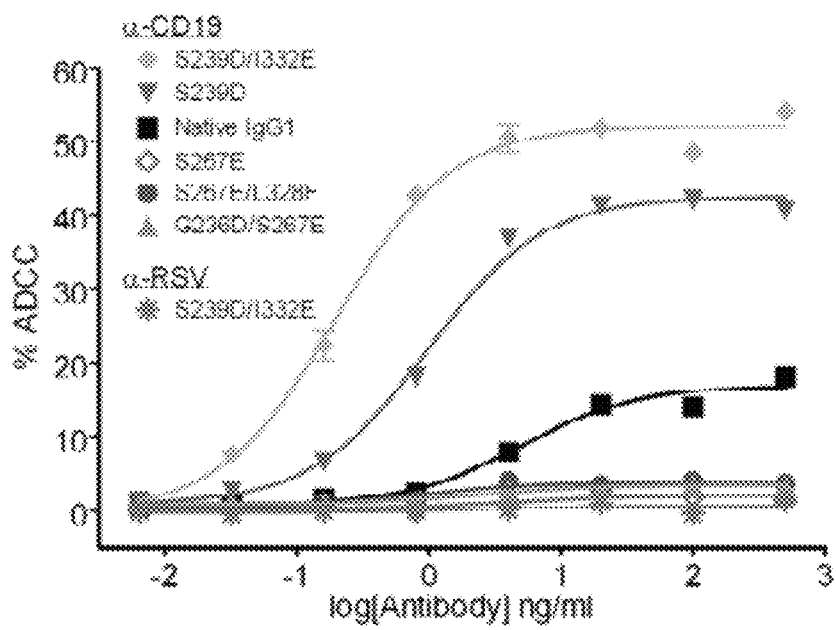
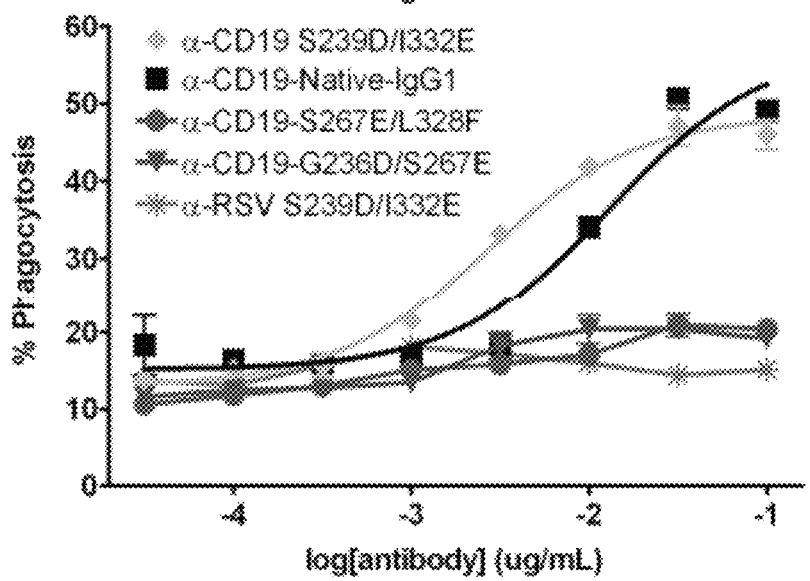

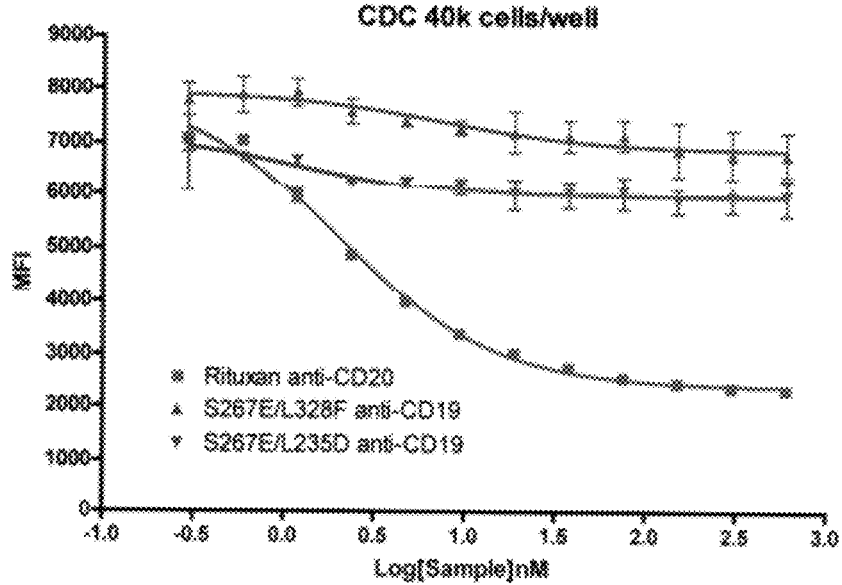

Figure 29

| Antigen | Expression | Function |
|---|---|---|
| CD19 | B, DC | BCR co-receptor |
| CD20 | B | Membrane $Ca^{++}$ regulator |
| CD21 (CR2) | B, DC | BCR co-receptor |
| CD22 | B | BCR co-receptor, negative regulator |
| CD23 / FcεRII | B, MΦ, Eos, DC | IgE receptor |
| FcεRI (α, β, and γ subunits) | Mast, Baso | IgE receptor |
| CD24 / BBA-1 / HSA | B | Cell adhesion and motility |
| CD27 | Memory B cells | T-cell interface |
| CD35 (CR1) | B | Complement receptor |
| CD38 | B, plasma | Cell adhesion |
| CD40 | B, DC | T-cell interface, T-cell co-stimulator |
| CD45RA | B | Membrane phosphatase |
| CD52 / CAMPATH-1 / HE5 | B | Cellular signaling |
| CD72 | B | BCR signaling modulator |
| CD79a (Igα) | B, DC | BCR signaling component |
| CD79b (Igβ) | B, DC | BCR signaling component |
| IgM (μ) | B | BCR antigen recognition component |
| CD80 | B, DC | T-cell interface |
| CD81 | B | BCR co-receptor |
| CD86 | B, DC | T-cell interface |
| Leu13 | B | BCR co-receptor |
| HLA-DR, -DP, -DQ | B, MΦ, DC | T-cell interface |
| CD138 | Plasma | Cellular adhesion and growth factor co-receptor |
| CD317 / HM1.24 | Plasma | Bone marrow stromal cell antigen (BST2) |
| CD11a | MΦ | integrin alpha L |
| CD11b | MΦ | integrin alpha M |
| CD11c | MΦ | integrin alpha X |
| CD14 | MΦ, PMN | LPS receptor |
| CD68 | MΦ | KP1, macrosialin |
| CD163 | MΦ | hemoglobin/haptoglobin scavenger receptor |
| CD172a | MΦ | SIRP-alpha |
| CD200R | MΦ | OX2 receptor |
| CD206 | MΦ | MΦ mannose receptor |

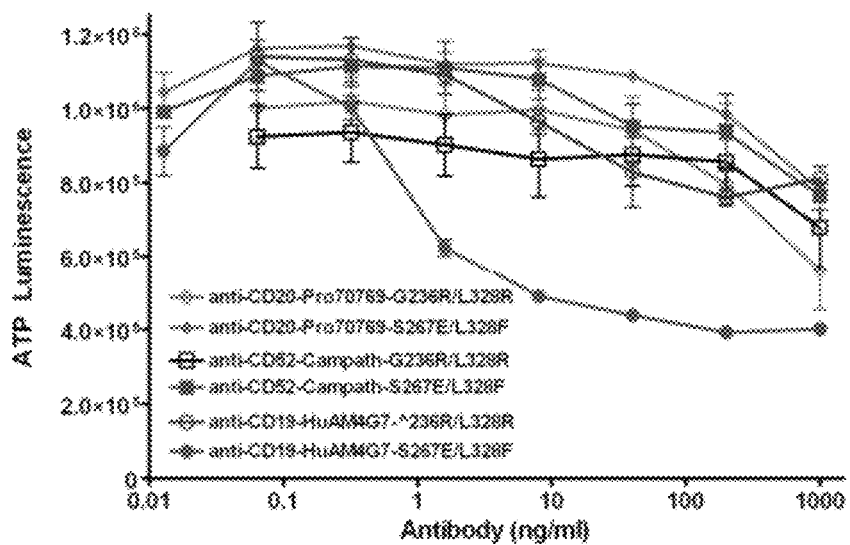
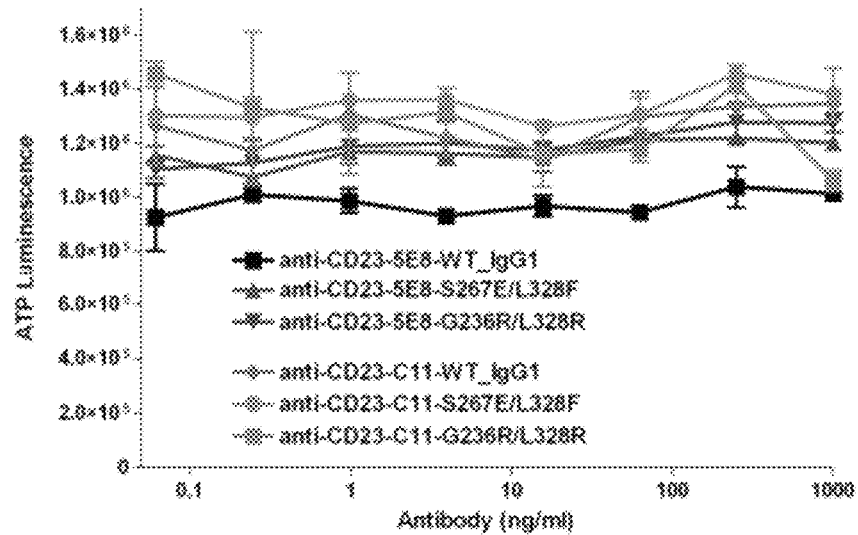

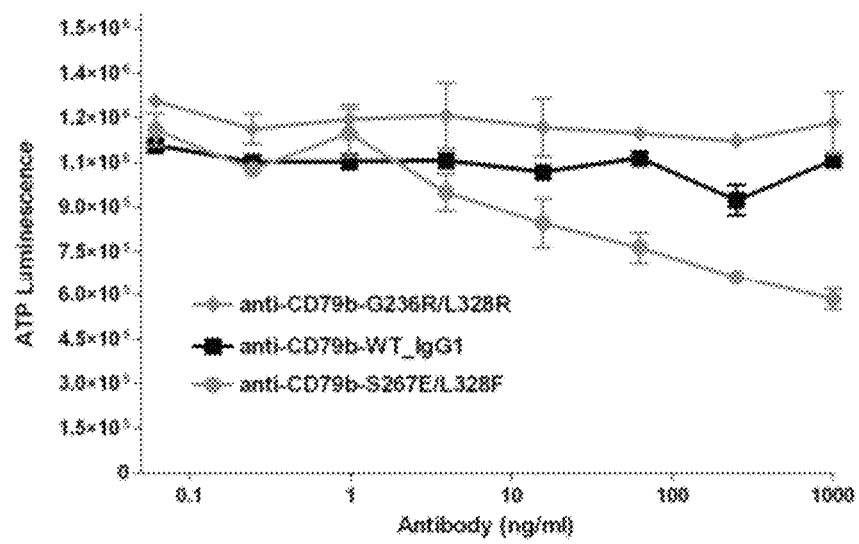
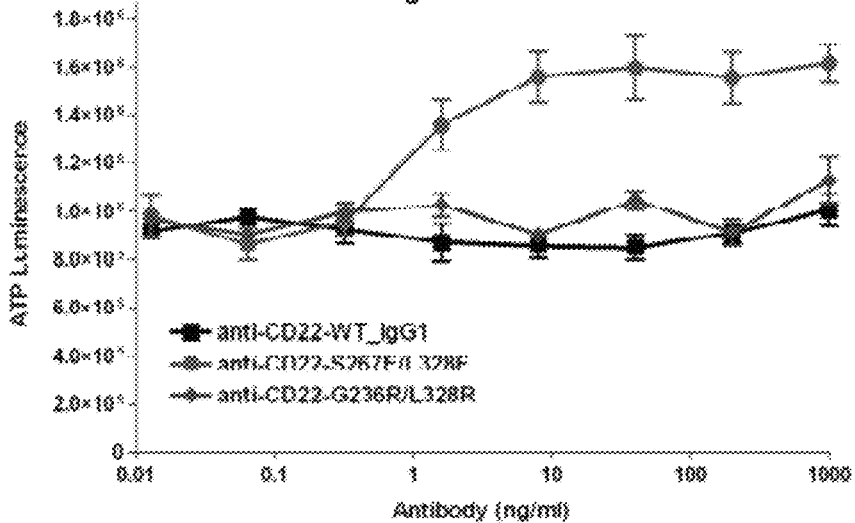

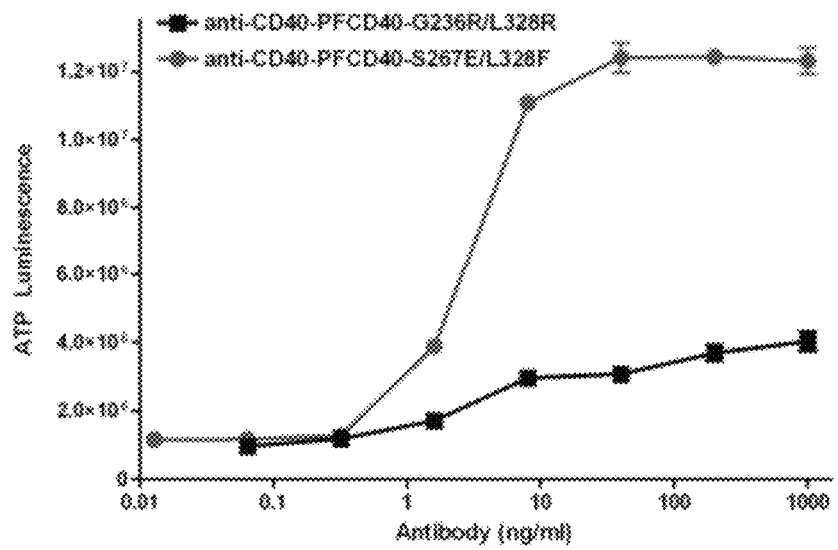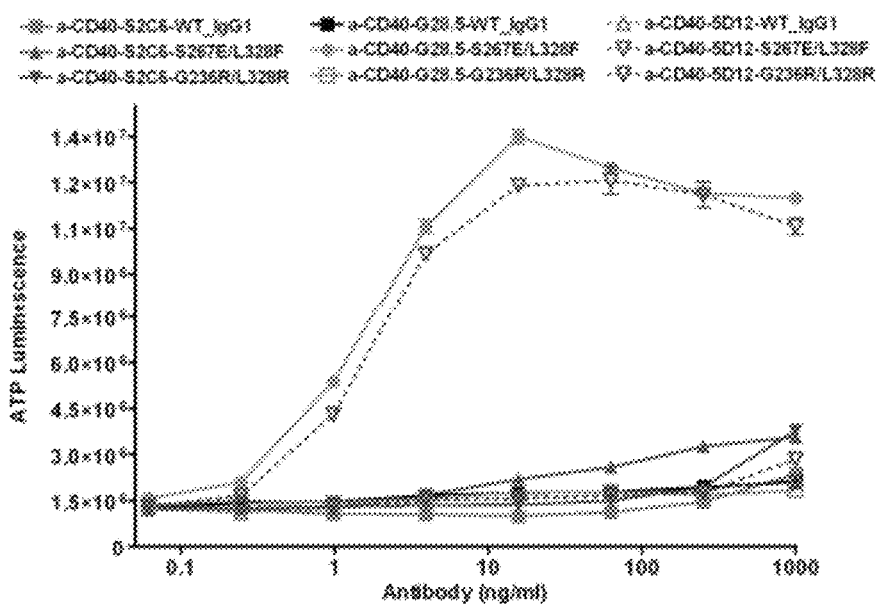

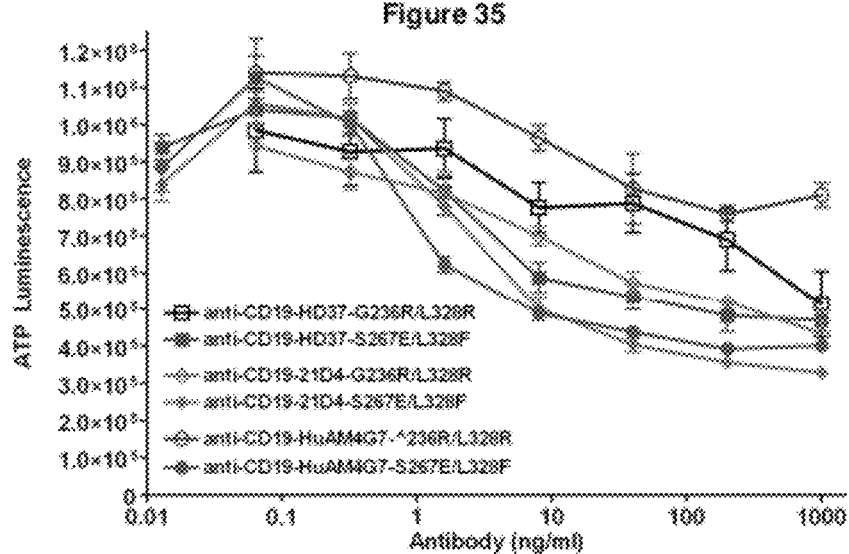

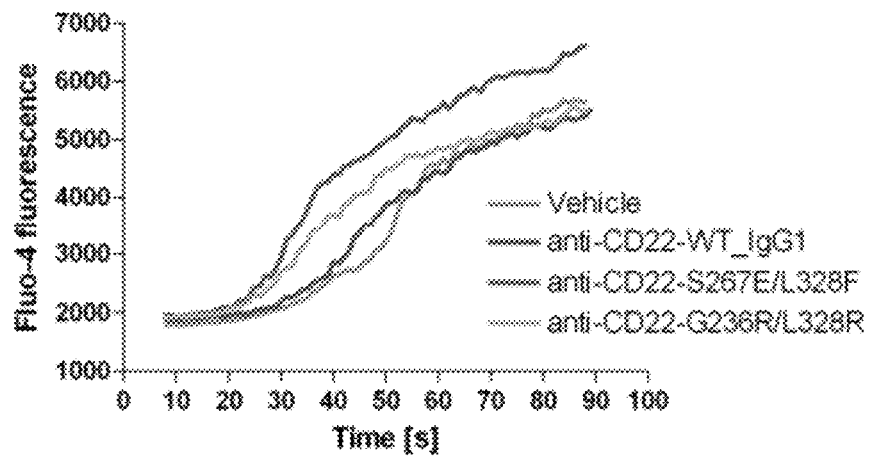
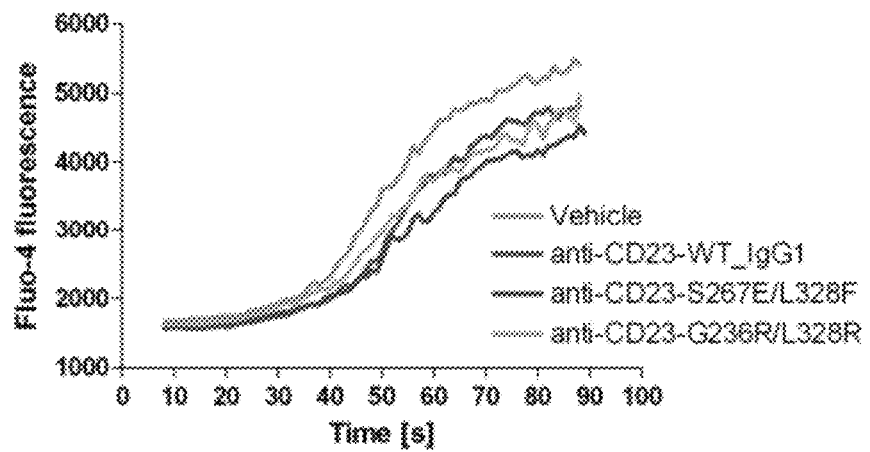

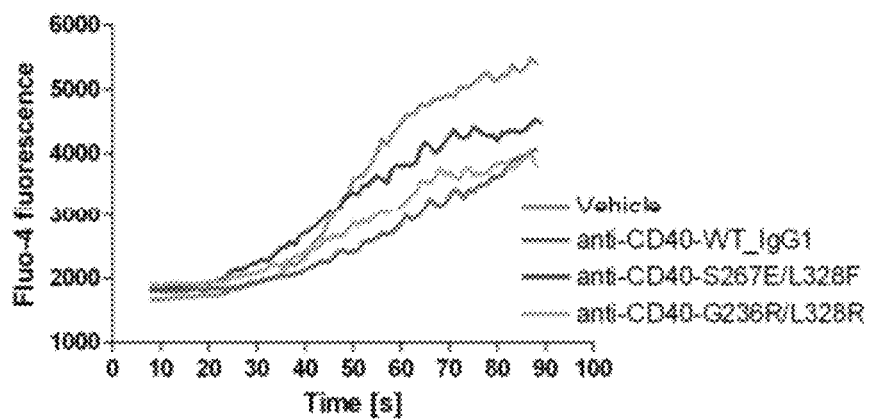
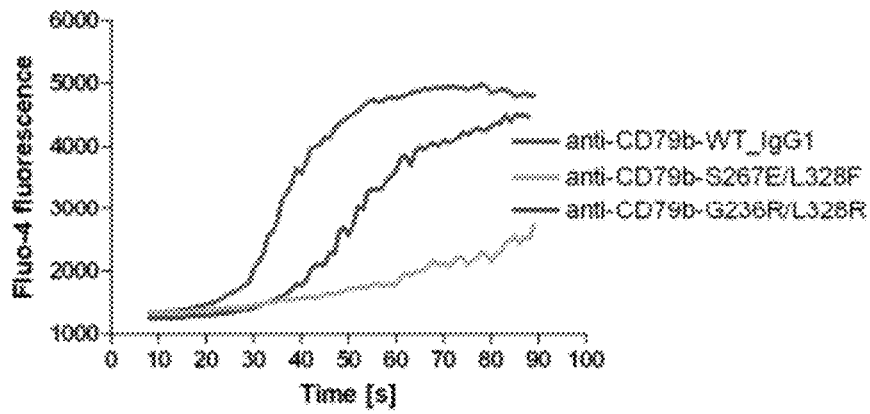

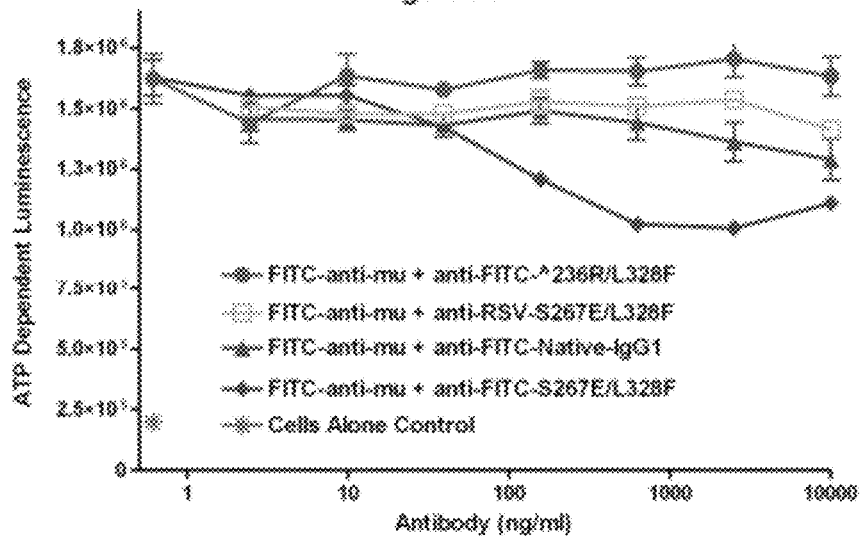
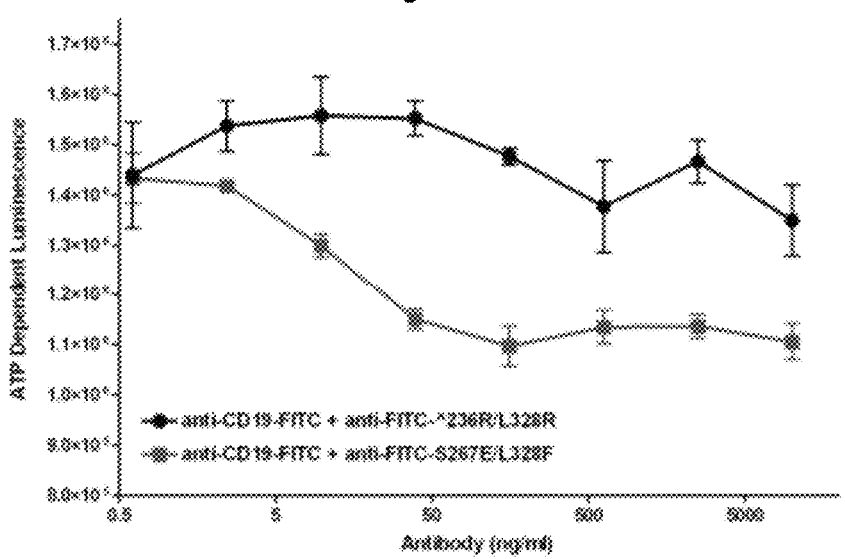

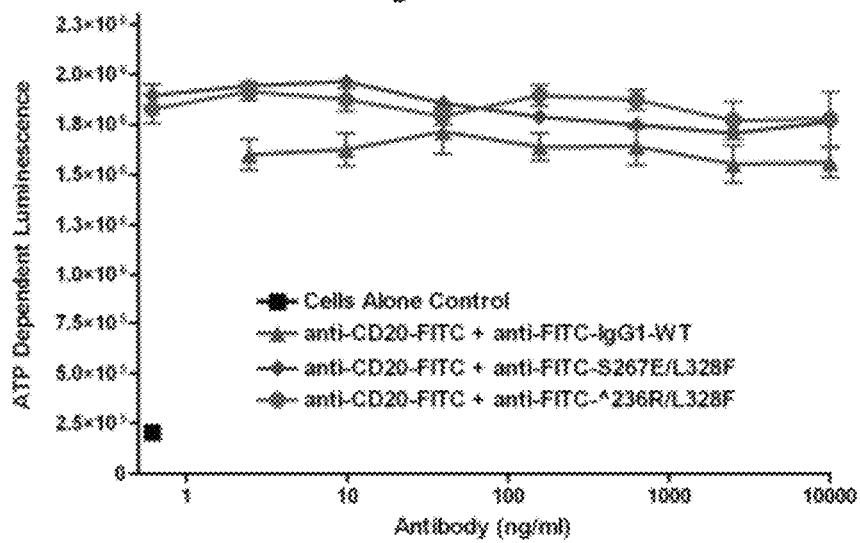
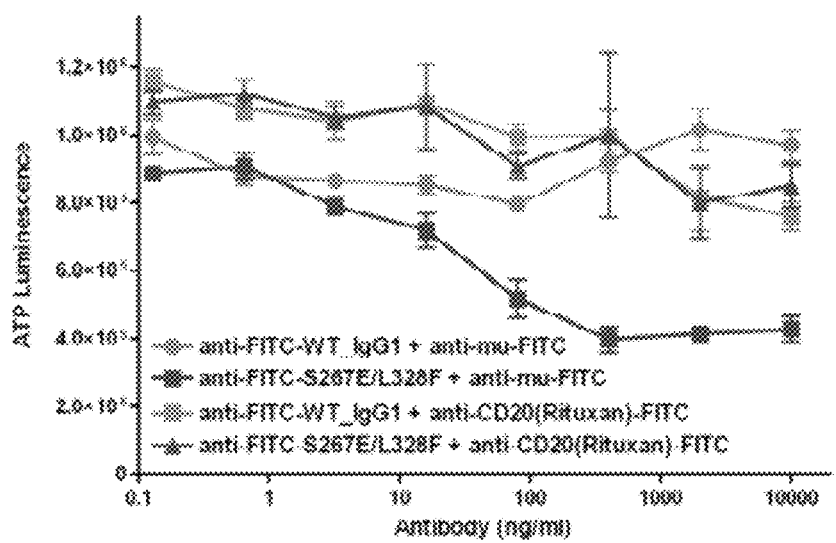

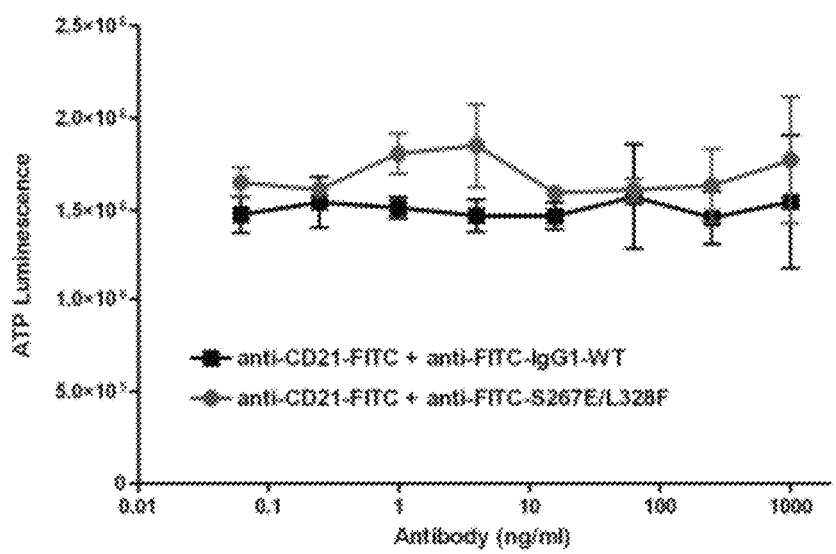
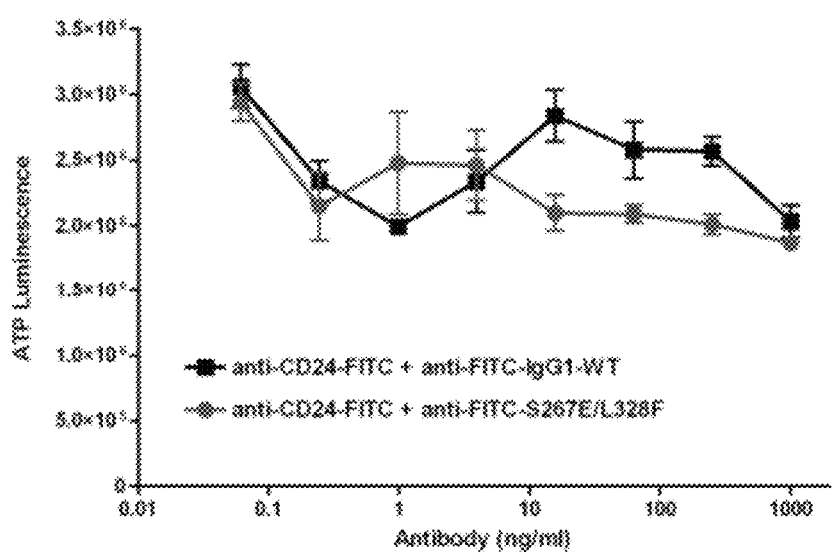

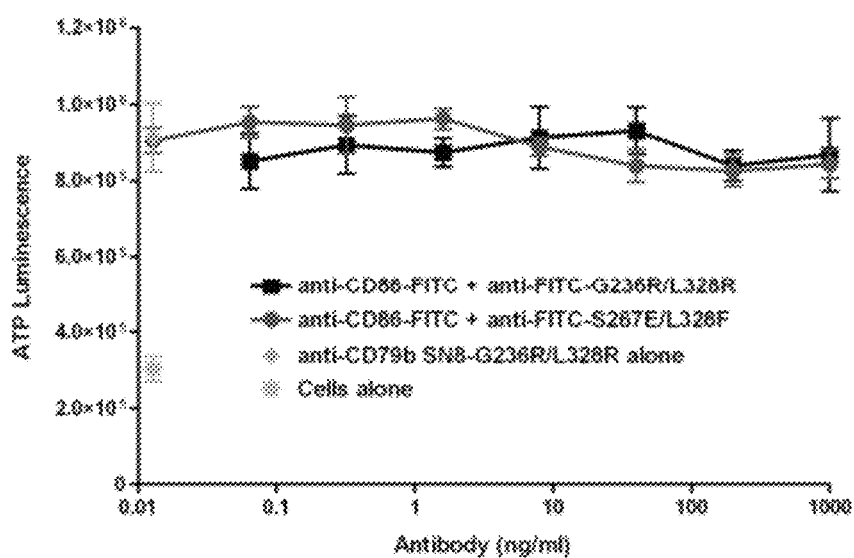
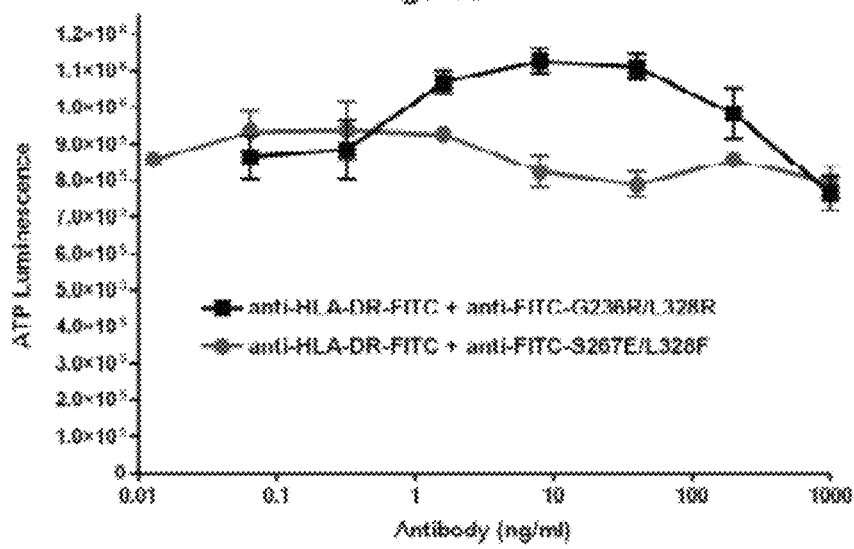

Figure 53

| Antigen | Approach | B cell viability | Calcium release |
|---|---|---|---|
| μ | Hapten | Inhibitory | ND |
| CD19 | Fc variant | Inhibitory | Inhibitory |
| | Hapten | Inhibitory | ND |
| CD20 | Fc variant | Not active | ND |
| | Hapten | Not active | ND |
| CD21 | Hapten | Not active | ND |
| CD22 | Fc variant | Stimulatory | Stimulatory |
| CD23 | Fc variant | Not active | Not active |
| CD24 | Hapten | Not active | ND |
| CD35 | Hapten | Not active | ND |
| CD40 | Fc variant | Stimulatory | Stimulatory |
| CD45RA | Hapten | Not active | ND |
| CD72 | Hapten | Stimulatory | ND |
| CD79a | Hapten | Inhibitory | ND |
| CD79b | Fc variant | Inhibitory | Inhibitory |
| | Hapten | Inhibitory | ND |
| CD80 | Hapten | Not active | ND |
| CD81 | Hapten | Possibly inhibitory | ND |
| CD86 | Hapten | Not active | ND |
| HLA-DR | Hapten | Possibly inhibitory | ND |
| ND = not determined | | | |

Figure 54A

HuAM4G7 VL (SEQ ID NO:1)
DIVMTQSPATLSLSPGERATLSCRSSKSLQNVNGNTYLYWFQQKPGQSPQLLIYRMSNLNS
GVPDRFSGSGSGTEFTLTISSLEPEDFAVYYCMQHLEYPITFGAGTKLEIK

HuAM4G7 VH (SEQ ID NO:2)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGTRVFDYWGQGTLVTVSS

Ckappa light chain (SEQ ID NO:3)
RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC Native IgG1 constant chain (SEQ ID NO:4)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK S267E/L328F IgG1 constant chain (SEQ ID NO:5)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKAFPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK G236D/S267E IgG1 constant chain (SEQ ID NO:6)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLDGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK HuAM4G7 light chain (VH-Cκ) (SEQ ID NO:7)
DIVMTQSPATLSLSPGERATLSCRSSKSLQNVNGNTYLYWFQQKPGQSPQLLIYRMSNLNS
GVPDRFSGSGSGTEFTLTISSLEPEDFAVYYCMQHLEYPITFGAGTKLEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC HuAM4G7 IgG1 heavy chain (SEQ ID NO:8)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGTRVFDYWGQGTLVTVSS
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

Figure 54B

HuAM4G7 S267E/L328F heavy chain (SEQ ID NO:9)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGTRVFDYWGQGTLVTVSS
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKAFPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK HuAM4G7 G236D/S267E heavy chain (SEQ ID NO:10)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGTRVFDYWGQGTLVTVSS
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLDGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK anti-RSV Numax VL (SEQ ID NO:11)
DIQMTQSPSTLSASVGDRVTITCSASSRVGYMHWYQQKPGKAPKLLIYDTSKLASGVPSRF
SGSGSGTEFTLTISSLQPDDFATYYCFQGSGYPFTFGGGTKVEIK
anti-RSV Numax VH (SEQ ID NO:12)
QVTLRESGPALVKPTQTLTLTCTFSGFSLSTAGMSVGWIRQPPGKALEWLADIWWDDKKH
YNPSLKDRLTISKDTSKNQVVLKVTNMDPADTATYYCARDMIFNFYFDVWGQGTTVTVSS anti-FITC VL (SEQ ID NO:13)
DVVMTQTPLSLPVSLGDQASISCRSSQSLVHSNGNTYLRWYLQKPGQSPKVLIYKVSNRFS
GVPDRFSGSGSGTDFTLKISRVEAEDLGVYFCSQSTHVPWTFGGGTKLEIK
anti-FITC VH (SEQ ID NO:14)
EVKLDETGGGLVQPGRPMKLSCVASGFTFSDYWMNWVRQSPEKGLEWVAQIRNKPYNYE
TYYSDSVKGRFTISRDDSKSSVYLQMNNLRVEDMGIYYCTGSYYGMDYWGQGTSVTVSS anti-CD79b SN8 VL (SEQ ID NO:15)
DIVLTQSPASLAVSLGQRATISCKASQSVDYDGDSFLNWYQQKPGQPPKLFIYAASNLESGI
PARFSGSGSGTDFTLNIHPVEEEDAATYYCQQSNEDPLTFGAGTELELK
anti-CD79b SN8 VH (SEQ ID NO:16)
EVQLQQSGAELMKPGASVKISCKATGYTFSSYWIEWVKQRPGHGLEWIGEILPGGGDTNY
NEIFKGKATFTADTSSNTAYMQLSSLTSEDSAVYYCTRRVPVYFDYWGQGTSVTVSS anti-CD20 Pro70769 VL (SEQ ID NO:17)
DIQMTQSPSSLSASVGDRVTITCRASSSVSYMHWYQQKPGKAPKPLIYAPSNLASGVPSRF
SGSGSGTDFTLTISSLQPEDFATYYCQQWSFNPPTFGQGTKVEIK
anti-CD20 Pro70769 VH (SEQ ID NO:18)
EVQLVESGGGLVQPGGSLRLSCAASGYTFTSYNMHWVRQAPGKGLEWVGAIYPGNGDTS
YNQKFKGRFTISVDKSKNTLYLQMNSLRAEDTAVYYCARVVYYSNSYWYFDVWGQGTLVT
VSS anti-CD52 Campath VL (SEQ ID NO:19)
DIQMTQSPSSLSASVGDRVTITCKASQNIDKYLNWYQQKPGKAPKLLIYNTNNLQTGVPSRF
SGSGSGTDFTFTISSLQPEDIATYYCLQHISRPRTFGQGTKVEIK

Figure 54C anti-CD52 Campath VH (SEQ ID NO:20)
QVQLQESGPGLVRPSQTLSLTCTVSGFTFTDFYMNWVRQPPGRGLEWIGFIRDKAKGYTT
EYNPSVKGRVTMLVDTSKNQFSLRLSSVTAADTAVYYCAREGHTAAPFDYWGQGSLVTVS
S anti-CD23 5E8 VL (SEQ ID NO:21)
DIQMTQSPSSLSASVGDRVTITCRASQDIRYYLNWYQQKPGKAPKLLIYVASSLQSGVPSRF
SGSGSGTEFTLTVSSLQPEDFATYYCLQVYSTPRTFGQGTKVEIK
anti-CD23 5E8 VH (SEQ ID NO:22)
EVQLVESGGGLAKPGGSLRLSCAASGFRFTFNNYYMDWVRQAPGQGLEWVSRISSSGDP
TWYADSVKGRFTISRENANNTLFLQMNSLRAEDTAVYYCASLTTGSDSWGQGVLVTVSS anti-CD23 C11 VL (SEQ ID NO:23)
DIVITQDELSNPVTSGESVSISCRSSKSLLYKDGKTYLNWFLQRPGQSPQLLMYLMSTRASG
VSDRFSGSGSGTDFTLEISRVKAEDVGVYYCQQLVEYPFTFGSGTKLEIK
anti-CD23 C11 VH (SEQ ID NO:24)
EVKLEESGGGLVQPGGSMKLSCVASGFTFSGYWMSWVRQSPEKGLEWVAEIRLKSDNYA
THYAESVKGKFTISRDDSKSRLYLQMNSLRAEDSGVYYCTDFIDWGQGTLVTVSS anti-CD22 RFB4 VL (SEQ ID NO:25)
DIQMTQTTSSLSASLGDRVTISCRASQDISNYLNWYQQKPDGTVKLLIYYTSILHSGVPSRFS
GSGSGTDYSLTISNLEQEDFATYFCQQGNTLPWTFGGGTKLEIK
anti-CD22 RFB4 VH (SEQ ID NO:26)
EVQLVESGGGLVKPGGSLKLSCAASGFAFSIYDMSWVRQTPEKRLEWVAYISSGGGTTYY
PDTVKGRFTISRDNAKNTLYLQMSSLKSEDTAMYYCARHSGYGSSYGVLFAYWGQGTLVT
TSA anti-CD40 PFCD40 VL (SEQ ID NO:27)
DIQMTQSPSSVSASVGDRVTITCRASQGIYSWLAWYQQKPGKAPNLLIYTASTLQSGVPSR
FSGSGSGTDFTLTISSLQPEDFATYYCQQANIFPLTFGGGTKVEIK
anti-CD40 PFCD40 VH (SEQ ID NO:28)
QVQLVQSGAEVKKPGASVKVSCKASGYTFTGYYMHWVRQAPGQGLEWMGWINPDSGGT
NYAQKFQGRVTMTRDTSISTAYMELNRLRSDDTAVYYCARDQPLGYCTNGVCSYFDYWG
QGTLVTVSS anti-CD40 S2C6 VL (SEQ ID NO:29)
DVVVTQTPLSLPVSLGAQASISCRSSQSLVHSNGNTFLHWYLQKPGQSPKLLIYTVSNRFS
GVPDRFSGSGSGTDFTLKISRVEAEDLGVYFCSQTTHVPWTFGGGTKLEIQ
anti-CD40 S2C6 VH (SEQ ID NO:30)
EVQLQQSGPDLVKPGASVKISCKASGYSFTGYYIHWVKQSHGKSLEWIGRVIPNNGGTSYN
QKFKGKAILTVDKSSSTAYMELRSLTSEDSAVYYCAREGIYWWGHGTTLTVSS anti-CD40 G28.5 VL (SEQ ID NO:31)
DAVMTQNPLSLPVSLGDEASISCRSSQSLENSNGNTFLNWFFQKPGQSPQLLIYRVSNRFS
GVPDRFSGSGSGTDFTLKISRVEAEDLGVYFCLQVTHVPYTFGGGTTLEIK
anti-CD40 G28.5 VH (SEQ ID NO:32)
DIQLQQSGPGLVKPSQSLSLTCSVTGYSITTNYNWNWIRQFPGNKLEWMGYIRYDGTSEYT
PSLKNRVSITRDTSMNQFFLRLTSVTPEDTATYYCARLDYWGQGTSVTVSS anti-CD40 5D12 VL (SEQ ID NO:33)
ELQLTQSPLSLPVSLGDQASISCRSSQSLVNSNGNTYLHWYLQKPGQSPKLLIYKVSNRFS
GVPDRFSGSGSGTDFTLKISRVEAEDLGVYFCSQSTHVPWTFGGGTKLEIK

Figure 54D anti-CD40 5D12 VH (SEQ ID NO:34)
QVKLEESGPGLVAPSQSLSITCTVSGFSLSRYSVYWVRQPPGKGLEWLGMMWGGGSTDY
NSALKSRLSISKDTSKSQVFLKMNSLQTDDTAMYYCVRTDGDYWGQGTSVTVSS anti-CD19 HD37 VL (SEQ ID NO:35)
DILLTQTPASLAVSLGQRATISCKASQSVDYDGDSYLNWYQQIPGQPPKLLIYDASNLVSGIP
PRFSGSGSGTDFTLNIHPVEKVDAATYHCQQSTEDPWTFGGGTKLEIK
anti-CD19 HD37 VH (SEQ ID NO:36)
QVQLQQSGAELVRPGSSVKISCKASGYAFSSYWMNWVKQRPGQGLEWIGQIWPGDGDT
NYNGKFKGKATLTADESSSTAYMQLSSLASEDSAVYFCARRETTTVGRYYYAMDYWGQG
TSVTVSS anti-CD19 21D4 VL (SEQ ID NO:37)
AIQLTQSPSSLSASVGDRVTITCRASQGISSALAWYQQKPGKAPKLLIYDASSLESGVPSRF
SGSGSGTDFTLTISSLQPEDFATYYCQQFNSYPYTFGQGTKLEIK
anti-CD19 21D4 VH (SEQ ID NO:38)
EVQLVQSGAEVKKPGESLKISCKGSGYSFSSSWIGWVRQMPGKGLEWMGIIYPDDSDTRY
SPSFQGQVTISADKSIRTAYLQWSSLKASDTAMYYCARHVTMWGVIIDFWGQGTLVTVSS anti-CD19 murine 4G7 VL (SEQ ID NO:39)
DIVMTQAAPSIPVTPGESVSISCRSSKSLLNSNGNTYLYWFLQRPGQSPQLLIYRMSNLASG
VPDRFSGSGSGTAFTLRISRVEAEDVGVYYCMQHLEYPFTFGAGTKLELK
anti-CD19 murine 4G7 VH (SEQ ID NO:40)
EVQLQQSGPELIKPGASVKMSCKASGYTFTSYVMHWVKQKPGQGLEWIGYINPYNDGTKY
NEKFKGKATLTSDKSSSTAYMELSSLTSEDSAVYYCARGTYYYGSRVFDYWGQGTTLTVS
S

SEQUENCE LISTING

<160> NUMBER OF SEQ ID NOS: 40

<210> SEQ ID NO 1
<211> LENGTH: 112
<212> TYPE: PRT
<213> ORGANISM: Artificial Sequence
<220> FEATURE:
<223> OTHER INFORMATION: Synthesized HuAM4G7 VL

<400> SEQUENCE: 1

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 2
<211> LENGTH: 121
<212> TYPE: PRT

<213> ORGANISM: Artificial Sequence
<220> FEATURE:
<223> OTHER INFORMATION: Synthesized HuAM4G7 VH

<400> SEQUENCE: 2

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
        115                 120

<210> SEQ ID NO 3
<211> LENGTH: 107
<212> TYPE: PRT
<213> ORGANISM: Homo sapiens

<400> SEQUENCE: 3

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 330
<212> TYPE: PRT
<213> ORGANISM: Artificial Sequence
<220> FEATURE:
<223> OTHER INFORMATION: Synthesized S267E/L328F IgG1 constant chain

<400> SEQUENCE: 5

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Phe Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 330
<212> TYPE: PRT
<213> ORGANISM: Artificial Sequence
<220> FEATURE:
<223> OTHER INFORMATION: Synthesized G236D/S267E IgG1 constant chain

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Asp Gly Pro Ser Val Phe Leu Phe Pro Pro
            115                 120                 125
```

Lys Pro Lys Asp Thr Leu Met Ile Ser Arg Thr Pro Glu Val Thr Cys
            130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 219
<212> TYPE: PRT
<213> ORGANISM: Artificial Sequence
<220> FEATURE:
<223> OTHER INFORMATION: Synthesized HuAM4G7 light chain (VH-C )

<400> SEQUENCE: 7

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 8
<211> LENGTH: 451
<212> TYPE: PRT
<213> ORGANISM: Artificial Sequence
<220> FEATURE:
<223> OTHER INFORMATION: Synthesized HuAM4G7 IgG1 heavy chain

<400> SEQUENCE: 8

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 9
<211> LENGTH: 451
<212> TYPE: PRT
<213> ORGANISM: Artificial Sequence
<220> FEATURE:
<223> OTHER INFORMATION: Synthesized HuAM4G7 S267E/L328F heavy chain

<400> SEQUENCE: 9

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
            85                  90                  95

Ala Arg Gly Thr Tyr Tyr Gly Thr Arg Val Phe Asp Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205
```

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Glu His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 10
<211> LENGTH: 451
<212> TYPE: PRT
<213> ORGANISM: Artificial Sequence
<220> FEATURE:
<223> OTHER INFORMATION: Synthesized HuAM4G7 G236D/S267E heavy chain

<400> SEQUENCE: 10

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110
```

```
Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Asp
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 11
<211> LENGTH: 106
<212> TYPE: PRT
<213> ORGANISM: Artificial Sequence
<220> FEATURE:
<223> OTHER INFORMATION: Synthesized anti-RSV Numax VL

<400> SEQUENCE: 11

Asp Ile Gln Met Thr Gln Ser Pro Ser Thr Leu Ser Ala Ser Val Gly
1               5                   10                  15
```

```
Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```

<210> SEQ ID NO 12
<211> LENGTH: 120
<212> TYPE: PRT
<213> ORGANISM: Artificial Sequence
<220> FEATURE:
<223> OTHER INFORMATION: Synthesized anti-RSV Numax VH

<400> SEQUENCE: 12

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120
```

<210> SEQ ID NO 13
<211> LENGTH: 112
<212> TYPE: PRT
<213> ORGANISM: Artificial Sequence
<220> FEATURE:
<223> OTHER INFORMATION: Synthesized anti-FITC VL

<400> SEQUENCE: 13

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95
```

```
Thr His Val Pro Trp Thr Phe Gly Gly Gly Thr Lys Leu Glu Ile Lys
            100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Synthesized anti-FITC VH

<400> SEQUENCE: 14

Glu Val Lys Leu Asp Glu Thr Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115

<210> SEQ ID NO 15
<211> LENGTH: 111
<212> TYPE: PRT
<213> ORGANISM: Mus musculus

<400> SEQUENCE: 15

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Phe Leu Asn Trp Tyr Gln Gln Lys Pro Gly Gln Pro Pro
            35                  40                  45

Lys Leu Phe Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Glu Leu Glu Leu Lys
            100                 105                 110

<210> SEQ ID NO 16
<211> LENGTH: 117
<212> TYPE: PRT
<213> ORGANISM: Mus musculus

<400> SEQUENCE: 16

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
```

```
                    20                  25                  30
Trp Ile Glu Trp Val Lys Gln Arg Pro Gly His Gly Leu Glu Trp Ile
            35                  40                  45
Gly Glu Ile Leu Pro Gly Gly Asp Thr Asn Tyr Asn Glu Ile Phe
        50                  55                  60
Lys Gly Lys Ala Thr Phe Thr Ala Asp Thr Ser Ser Asn Thr Ala Tyr
65                  70                  75                  80
Met Gln Leu Ser Ser Leu Thr Ser Glu Asp Ser Ala Val Tyr Tyr Cys
                85                  90                  95
Thr Arg Arg Val Pro Val Tyr Phe Asp Tyr Trp Gly Gln Gly Thr Ser
                100                 105                 110
Val Thr Val Ser Ser
        115

<210> SEQ ID NO 17
<211> LENGTH: 106
<212> TYPE: PRT
<213> ORGANISM: Artificial Sequence
<220> FEATURE:
<223> OTHER INFORMATION: Synthesized anti-CD20 Pro70769 VL

<400> SEQUENCE: 17

Asp Ile Gln Met Thr Gln Ser Pro Ser Ser Leu Ser Ala Ser Val Gly
1               5                   10                  15
Asp Arg Val Thr Ile Thr Cys Arg Ala Ser Ser Ser Val Ser Tyr Met
                20                  25                  30
His Trp Tyr Gln Gln Lys Pro Gly Lys Ala Pro Lys Pro Leu Ile Tyr
            35                  40                  45
Ala Pro Ser Asn Leu Ala Ser Gly Val Pro Ser Arg Phe Ser Gly Ser
        50                  55                  60
Gly Ser Gly Thr Asp Phe Thr Leu Thr Ile Ser Ser Leu Gln Pro Glu
65                  70                  75                  80
Asp Phe Ala Thr Tyr Tyr Cys Gln Gln Trp Ser Phe Asn Pro Pro Thr
                85                  90                  95
Phe Gly Gln Gly Thr Lys Val Glu Ile Lys
                100                 105

<210> SEQ ID NO 18
<211> LENGTH: 122
<212> TYPE: PRT
<213> ORGANISM: Artificial Sequence
<220> FEATURE:
<223> OTHER INFORMATION: Synthesized anti-CD20 Pro70769 VH

<400> SEQUENCE: 18

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Ser Tyr
                20                  25                  30
Asn Met His Trp Val Arg Gln Ala Pro Gly Lys Gly Leu Glu Trp Val
            35                  40                  45
Gly Ala Ile Tyr Pro Gly Asn Gly Asp Thr Ser Tyr Asn Gln Lys Phe
        50                  55                  60
Lys Gly Arg Phe Thr Ile Ser Val Asp Lys Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

```
Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 19
<211> LENGTH: 107
<212> TYPE: PRT
<213> ORGANISM: Artificial Sequence
<220> FEATURE:
<223> OTHER INFORMATION: Synthesized anti-CD52 Campath VL

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 20
<211> LENGTH: 121
<212> TYPE: PRT
<213> ORGANISM: Artificial Sequence
<220> FEATURE:
<223> OTHER INFORMATION: Synthesized anti-CD52 Campath VH

<400> SEQUENCE: 20

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
        115                 120

<210> SEQ ID NO 21
<211> LENGTH: 107
<212> TYPE: PRT
<213> ORGANISM: Mus musculus

<400> SEQUENCE: 21
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Leu Gln Val Tyr Ser Thr Pro Arg
                85                  90                  95

Thr Phe Gly Gln Gly Thr Lys Val Glu Ile Lys
            100                 105
```

<210> SEQ ID NO 22
<211> LENGTH: 118
<212> TYPE: PRT
<213> ORGANISM: Mus musculus

<400> SEQUENCE: 22

```
Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Arg Phe Thr Phe Asn
            20                  25                  30

Asn Tyr Tyr Met Asp Trp Val Arg Gln Ala Pro Gly Gln Gly Leu Glu
        35                  40                  45

Trp Val Ser Arg Ile Ser Ser Gly Asp Pro Thr Trp Tyr Ala Asp
50                  55                  60

Ser Val Lys Gly Arg Phe Thr Ile Ser Arg Glu Asn Ala Asn Asn Thr
65                  70                  75                  80

Leu Phe Leu Gln Met Asn Ser Leu Arg Ala Glu Asp Thr Ala Val Tyr
                85                  90                  95

Tyr Cys Ala Ser Leu Thr Thr Gly Ser Asp Ser Trp Gly Gln Gly Val
            100                 105                 110

Leu Val Thr Val Ser Ser
            115
```

<210> SEQ ID NO 23
<211> LENGTH: 112
<212> TYPE: PRT
<213> ORGANISM: Mus musculus

<400> SEQUENCE: 23

```
Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Met Tyr Leu Met Ser Thr Arg Ala Ser Gly Val Ser
50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95
```

Val Glu Tyr Pro Phe Thr Phe Gly Ser Gly Thr Lys Leu Glu Ile Lys
            100                 105                 110

<210> SEQ ID NO 24
<211> LENGTH: 114
<212> TYPE: PRT
<213> ORGANISM: Mus musculus

<400> SEQUENCE: 24

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Gly Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Ala Glu Asp Ser Gly Val Tyr
                85                  90                  95

Tyr Cys Thr Asp Phe Ile Asp Trp Gly Gln Gly Thr Leu Val Thr Val
            100                 105                 110

Ser Ser

<210> SEQ ID NO 25
<211> LENGTH: 107
<212> TYPE: PRT
<213> ORGANISM: Mus musculus

<400> SEQUENCE: 25

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 26
<211> LENGTH: 123
<212> TYPE: PRT
<213> ORGANISM: Mus musculus

<400> SEQUENCE: 26

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

```
Ala Tyr Ile Ser Ser Gly Gly Thr Thr Tyr Tyr Pro Asp Thr Val
        50                  55                  60
Lys Gly Arg Phe Thr Ile Ser Arg Asp Asn Ala Lys Asn Thr Leu Tyr
 65                  70                  75                  80
Leu Gln Met Ser Ser Leu Lys Ser Glu Asp Thr Ala Met Tyr Tyr Cys
                85                  90                  95
Ala Arg His Ser Gly Tyr Gly Ser Ser Tyr Gly Val Leu Phe Ala Tyr
            100                 105                 110
Trp Gly Gln Gly Thr Leu Val Thr Thr Ser Ala
            115                 120

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Val Ser Ala Ser Val Gly
  1               5                  10                  15
Asp Arg Val Thr Ile Thr Cys Arg Ala Ser Gln Gly Ile Tyr Ser Trp
                20                  25                  30
Leu Ala Trp Tyr Gln Gln Lys Pro Gly Lys Ala Pro Asn Leu Leu Ile
            35                  40                  45
Tyr Thr Ala Ser Thr Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ile Phe Pro Leu
                85                  90                  95
Thr Phe Gly Gly Gly Thr Lys Val Glu Ile Lys
            100                 105

<210> SEQ ID NO 28
<211> LENGTH: 126
<212> TYPE: PRT
<213> ORGANISM: Homo sapiens

<400> SEQUENCE: 28

Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
            35                  40                  45
Gly Trp Ile Asn Pro Asp Ser Gly Gly Thr Asn Tyr Ala Gln Lys Phe
        50                  55                  60
Gln Gly Arg Val Thr Met Thr Arg Asp Thr Ser Ile Ser Thr Ala Tyr
 65                  70                  75                  80
Met Glu Leu Asn Arg Leu Arg Ser Asp Thr Ala Val Tyr Tyr Cys
                85                  90                  95
Ala Arg Asp Gln Pro Leu Gly Tyr Cys Thr Asn Gly Val Cys Ser Tyr
            100                 105                 110
Phe Asp Tyr Trp Gly Gln Gly Thr Leu Val Thr Val Ser Ser
            115                 120                 125

<210> SEQ ID NO 29
```

<211> LENGTH: 112
<212> TYPE: PRT
<213> ORGANISM: Mus musculus

<400> SEQUENCE: 29

```
Asp Val Val Thr Gln Thr Pro Leu Ser Leu Pro Val Ser Leu Gly
1               5                   10                  15

Ala Gln Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Gln
            100                 105                 110
```

<210> SEQ ID NO 30
<211> LENGTH: 114
<212> TYPE: PRT
<213> ORGANISM: Mus musculus

<400> SEQUENCE: 30

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Ser His Gly Lys Ser Leu Glu Trp Ile
        35                  40                  45

Gly Arg Val Ile Pro Asn Asn Gly Gly Thr Ser Tyr Asn Gln Lys Phe
    50                  55                  60

Lys Gly Lys Ala Ile Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Ile Tyr Trp Trp Gly His Gly Thr Thr Leu Thr Val
            100                 105                 110

Ser Ser
```

<210> SEQ ID NO 31
<211> LENGTH: 112
<212> TYPE: PRT
<213> ORGANISM: Mus musculus

<400> SEQUENCE: 31

```
Asp Ala Val Met Thr Gln Asn Pro Leu Ser Leu Pro Val Ser Leu Gly
1               5                   10                  15

Asp Glu Ala Ser Ile Ser Cys Arg Ser Ser Gln Ser Leu Glu Asn Ser
            20                  25                  30

Asn Gly Asn Thr Phe Leu Asn Trp Phe Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Thr Leu Glu Ile Lys
            100                 105                 110
```

<210> SEQ ID NO 32
<211> LENGTH: 112
<212> TYPE: PRT
<213> ORGANISM: Mus musculus

<400> SEQUENCE: 32

```
Asp Ile Gln Leu Gln Gln Ser Gly Pro Gly Leu Val Lys Pro Ser Gln
1               5                   10                  15

Ser Leu Ser Leu Thr Cys Ser Val Thr Gly Tyr Ser Ile Thr Thr Asn
                20                  25                  30

Tyr Asn Trp Asn Trp Ile Arg Gln Phe Pro Gly Asn Lys Leu Glu Trp
            35                  40                  45

Met Gly Tyr Ile Arg Tyr Asp Gly Thr Ser Glu Tyr Thr Pro Ser Leu
        50                  55                  60

Lys Asn Arg Val Ser Ile Thr Arg Asp Thr Ser Met Asn Gln Phe Phe
65                  70                  75                  80

Leu Arg Leu Thr Ser Val Thr Pro Glu Asp Thr Ala Thr Tyr Tyr Cys
                85                  90                  95

Ala Arg Leu Asp Tyr Trp Gly Gln Gly Thr Ser Val Thr Val Ser Ser
            100                 105                 110
```

<210> SEQ ID NO 33
<211> LENGTH: 112
<212> TYPE: PRT
<213> ORGANISM: Mus musculus

<400> SEQUENCE: 33

```
Glu Leu Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val Asn Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 34
<211> LENGTH: 113
<212> TYPE: PRT
<213> ORGANISM: Mus musculus

<400> SEQUENCE: 34

```
Gln Val Lys Leu Glu Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
                20                  25                  30
```

```
Ser Val Tyr Trp Val Arg Gln Pro Gly Lys Gly Leu Glu Trp Leu
            35                  40                  45

Gly Met Met Trp Gly Gly Ser Thr Asp Tyr Asn Ser Ala Leu Lys
 50                      55                  60

Ser Arg Leu Ser Ile Ser Lys Asp Thr Ser Lys Ser Gln Val Phe Leu
 65                  70                  75                  80

Lys Met Asn Ser Leu Gln Thr Asp Asp Thr Ala Met Tyr Tyr Cys Val
                 85                  90                  95

Arg Thr Asp Gly Asp Tyr Trp Gly Gln Gly Thr Ser Val Thr Val Ser
             100                 105                 110

Ser
```

<210> SEQ ID NO 35
<211> LENGTH: 111
<212> TYPE: PRT
<213> ORGANISM: Mus musculus

<400> SEQUENCE: 35

```
Asp Ile Leu Leu Thr Gln Thr Pro Ala Ser Leu Ala Val Ser Leu Gly
 1               5                  10                  15

Gln Arg Ala Thr Ile Ser Cys Lys Ala Ser Gln Ser Val Asp Tyr Asp
                 20                  25                  30

Gly Asp Ser Tyr Leu Asn Trp Tyr Gln Gln Ile Pro Gly Gln Pro Pro
             35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
             100                 105                 110
```

<210> SEQ ID NO 36
<211> LENGTH: 124
<212> TYPE: PRT
<213> ORGANISM: Mus musculus

<400> SEQUENCE: 36

```
Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
                 20                  25                  30

Trp Met Asn Trp Val Lys Gln Arg Pro Gly Gln Gly Leu Glu Trp Ile
             35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
             100                 105                 110

Tyr Trp Gly Gln Gly Thr Ser Val Thr Val Ser Ser
             115                 120
```

```
<210> SEQ ID NO 37
<211> LENGTH: 107
<212> TYPE: PRT
<213> ORGANISM: Mus musculus

<400> SEQUENCE: 37

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 38
<211> LENGTH: 120
<212> TYPE: PRT
<213> ORGANISM: Mus musculus

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Trp Gly Val Ile Ile Asp Phe Trp Gly Gln
            100                 105                 110

Gly Thr Leu Val Thr Val Ser Ser
        115                 120

<210> SEQ ID NO 39
<211> LENGTH: 112
<212> TYPE: PRT
<213> ORGANISM: Mus musculus

<400> SEQUENCE: 39

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
```

```
                50                  55                 60
Asp Arg Phe Ser Gly Ser Gly Ser Gly Thr Ala Phe Thr Leu Arg Ile
 65                  70                 75                  80

Ser Arg Val Glu Ala Glu Asp Val Gly Val Tyr Tyr Cys Met Gln His
                 85                 90                  95

Leu Glu Tyr Pro Phe Thr Phe Gly Ala Gly Thr Lys Leu Glu Leu Lys
                100                105                 110

<210> SEQ ID NO 40
<211> LENGTH: 121
<212> TYPE: PRT
<213> ORGANISM: Mus musculus

<400> SEQUENCE: 40

Glu Val Gln Leu Gln Gln Ser Gly Pro Glu Leu Ile Lys Pro Gly Ala
 1               5                  10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
             35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                 90                  95

Ala Arg Gly Thr Tyr Tyr Tyr Gly Ser Arg Val Phe Asp Tyr Trp Gly
                100                105                 110

Gln Gly Thr Thr Leu Thr Val Ser Ser
                115                120
```

METHODS AND COMPOSITIONS FOR INHIBITING CD32B EXPRESSING CELLS

RELATED APPLICATIONS

This application claims benefit under 35 U.S.C §120 to, and is a continuation of U.S. application Ser. No. 13/301,464 (filed Nov. 21, 2011); which claims benefit under 35 U.S.C §120 to, and is a continuation of Ser. No. 12/156,183 (filed May 30, 2008), now U.S. Pat. No. 8,063,187; which claims benefit under 35 U.S.C §119(e) of U.S. Provisional Application Nos. 60/940,776 (filed May 30, 2007); 60/953,174 (filed Jul. 31, 2007); 60/970,413 (filed Sep. 6, 2007); 60/976,279 (filed Sep. 28, 2007); 60/990,509 (filed Nov. 27, 2007); 61/012,035 (filed Dec. 6, 2007); 61/013,775 (filed Dec. 14, 2007), 61/019,395 (filed Jan. 7, 2008), 61/032,059 (filed Feb. 27, 2008), 61/043,585 (filed Apr. 9, 2008), and 61/046,397 (filed Apr. 18, 2008). Each of the above applications is incorporated herein by reference in its entirety.

SEQUENCE LISTING

A Sequence Listing submitted in computer readable form (CRF) is hereby incorporated by reference.

TECHNICAL FIELD

The present disclosure relates to methods of inhibiting cells that express the Fc gamma receptor CD32b (FcγRIIb), immunoglobulin compositions that may be useful for such methods, and application of such compositions for treating immune disorders and hematological malignancies.

BACKGROUND

Antigen recognition by B cells is mediated by the B cell receptor (BCR), a surface-bound immunoglobulin in complex with signaling components CD79a (Igα) and CD79b (Igβ). Crosslinking of BCR upon engagement of antigen results in phosphorylation of immunoreceptor tyrosine-based activation motifs (ITAMs) within CD79a and CD79b, initiating a cascade of intracellular signaling events that recruit downstream molecules to the membrane and stimulate calcium mobilization. This leads to the induction of diverse B cell responses (e.g., cell survival, proliferation, antibody production, antigen presentation, differentiation, etc.) which lead to a humoral immune response (DeFranco, A. L., 1997, Curr. Opin. Immunol. 9, 296-308; Pierce, S. K., 2002, Nat. Rev. Immunol. 2, 96-105; Ravetch, J. V. & Lanier, L. L., 2000, Science 290, 84-89). Other components of the BCR coreceptor complex enhance (e.g., CD19, CD21, and CD81) or suppress (e.g., CD22 and CD72) BCR activation signals (Doody, G. M. et al., 1996, Curr. Opin. Immunol. 8, 378-382; Li, D. H. et al., 2006, J. Immunol. 176, 5321-5328). In this way, the immune system maintains multiple BCR regulatory mechanisms to ensure that B cell responses are tightly controlled.

When antibodies are produced to an antigen, the circulating level of immune complexes (e.g., antigen bound to antibody) increases. These immune complexes downregulate antigen-induced B cell activation. It is believed that these immune complexes downregulate antigen-induced B cell activation by coengaging cognate BCR with the low-affinity inhibitory receptor FcγRIIb, the only IgG receptor on B cells (Heyman, B., 2003, Immunol. Lett. 88, 157-161). It is also believed that this negative feedback of antibody production requires interaction of the antibody Fc domain with FcγRIIb since immune complexes containing F(ab')$_2$ antibody fragments are not inhibitory (Chan, P. L. & Sinclair, N. R., 1973, Immunology 24, 289-301). The intracellular immunoreceptor tyrosine-based inhibitory motif (ITIM) of FcγRIIb is necessary to inhibit BCR-induced intracellular signals (Amigorena, S. et al., 1992, Science 256, 1808-1812; Muta, T., et al., 1994, Nature 368, 70-73). This inhibitory effect occurs through phosphorylation of the FcγRIIb ITIM, which recruits SH2-containing inositol polyphosphate 5-phosphatase (SHIP) to neutralize ITAM-induced intracellular calcium mobilization (Kiener, P. A., et al., 1997, J. Biol. Chem. 272, 3838-3844; Ono, M., et al., 1996, Nature 383, 263-266; Ravetch, J. V. & Lanier, L. L., 2000, Science 290, 84-89). In addition, FcγRIIb-mediated SHIP phosphorylation inhibits the downstream Ras-MAPK proliferation pathway (Tridandapani, S. et al., 1998, Immunol. 35, 1135-1146).

SUMMARY OF EXEMPLARY EMBODIMENTS

The present disclosure provides novel immunoglobulins, compositions comprising such immunoglobulins, and methods of using the immunoglobulin to inhibit cells that express FcγRIIb. The FcγRIIb$^+$ cell inhibitory methods disclosed herein comprise contacting FcγRIIb$^+$ cells with an immunoglobulin that binds FcγRIIb and coengages a target antigen on the cell's surface and an FcγRIIb on the cell's surface. In one embodiment, the immunoglobulin binds with FcγRIIb, wherein the affinity of said binding has a Kd less than about 100 nM, e.g., less than or equal to about 95 nM, less than or equal to about 90 nM, less than or equal to about 85 nM, less than or equal to about 80 nM, less than or equal to about 75 nM, less than or equal to about 74 nM. In one embodiment, the immunoglobulin comprises an Fc region, wherein said Fc region comprises one or more modifications compared to a parent Fc region, wherein said modifications are at positions selected from the group consisting of 234, 235, 236, 237, 239, 265, 266, 267, 268, 298, 325, 326, 327, 328, 329, 330, 331, and 332, wherein numbering is according to the EU index. In another embodiment, the immunoglobulin is a bispecific antibody comprising a first Fv region and a second Fv region, wherein said first Fv region binds the target antigen, and said second Fv region binds FcγRIIb with a Kd of less than about 100 nM. In another embodiment, the immunoglobulin is an Fc fusion comprising an Fc region, wherein said Fc region binds FcγRIIb with a Kd of less than about 100 nM. FcγRIIb$^+$ cells as disclosed herein may be cancer cells, B cells, plasma cells, dendritic cells, macrophages, neutrophils, mast cells, basophils, eosinophils, and a combination thereof.

Also disclosed herein are novel methods of inhibiting activation of B cells. The B cell inhibitory methods disclosed herein comprise contacting B cells with an immunoglobulin that binds FcγRIIb and coengages a target antigen on the B cell's surface and an FcγRIIb on the B cell's surface. In one embodiment, the immunoglobulin binds with FcγRIIb, wherein the affinity of said binding has a Kd less than about 100 nM, e.g., less than or equal to about 95 nM, less than or equal to about 90 nM, less than or equal to about 85 nM, less than or equal to about 80 nM, less than or equal to about 75 nM, less than or equal to about 74 nM. In one embodiment, the immunoglobulin comprises an Fc region, wherein said Fc region comprises one or more modifications compared to a parent Fc region, wherein said modifications are at positions selected from the group consisting of 234, 235, 236, 237, 239, 265, 266, 267, 268, 298, 325, 326, 327, 328, 329, 330, 331, and 332, wherein numbering is according to the EU index. In another embodiment, the immunoglobulin is a bispecific antibody comprising a first Fv region and a second Fv region, wherein said first Fv region binds the target antigen, and said second Fv region binds FcγRIIb with a Kd of less than about 100 nM. In another embodiment, the immunoglobulin is an Fc fusion comprising an Fc region, wherein said Fc region binds FcγRIIb with a Kd of less than about 100 nM. In one embodiment, the immunoglobulin binds at least two B cell proteins, .e.g., at least two proteins bound, or that may be bound, on the surface of B cells. In one embodiment, the first of said B cell proteins is FcγRIIb and the second of said B cell proteins is part of the B cell receptor (BCR) complex. In another embodiment, the second of said B cell proteins is not involved directly in antigen recognition. In another embodiment, the second of said B cell proteins is an antigen bound to the BCR complex. In some embodiments, the immunoglobulins inhibit release of calcium from the B cells upon their stimulation through the B cell receptor. In another embodiment, an immunoglobulin disclosed herein binds at least two B cell proteins bound on the surface of the same B cell.

Also disclosed herein are novel methods of treating B cell-mediated disorders, e.g., autoimmune diseases, inflammatory diseases, hematological malignancies, etc. The treatment methods disclosed herein comprise administration to a patient in need of such administration a therapeutic amount of an immunoglobulin that binds FcγRIIb+ cells and coengages a target antigen on the cell's surface and an FcγRIIb on cell's surface. In one embodiment, the immunoglobulin binds with FcγRIIb, wherein the affinity of said binding has a Kd less than about 100 nM, e.g., less than or equal to about 95 nM, less than or equal to about 90 nM, less than or equal to about 85 nM, less than or equal to about 80 nM, less than or equal to about 75 nM, less than or equal to about 74 nM. In one embodiment, the immunoglobulin comprises an Fc region, wherein said Fc region comprises one or more modifications compared to a parent Fc region, wherein said modifications are at positions selected from the group consisting of 234, 235, 236, 237, 239, 265, 266, 267, 268, 298, 325, 326, 327, 328, 329, 330, 331, and 332, wherein numbering is according to the EU index. In another embodiment, the immunoglobulin is a bispecific antibody comprising a first Fv region and a second Fv region, wherein said first Fv region binds the target antigen, and said second Fv region binds FcγRIIb with a Kd of less than about 100 nM. In another embodiment, the immunoglobulin is an Fc fusion comprising an Fc region, wherein said Fc region binds FcγRIIb with a Kd of less than about 100 nM. In some embodiments, autoimmune and inflammatory diseases that may be treated by the methods disclosed herein include Systemic Lupus Erythematosus, Rheumatoid arthritis, Sjogren's syndrome, Multiple sclerosis, Idiopathic thrombocytopenic purpura (ITP), Graves disease, Inflammatory bowel disease, Psoriasis, Type I diabetes, and Asthma.

Disclosed herein are novel FcγRIIb+ cell inhibitory immunoglobulin compositions. The compositions disclosed herein include immunoglobulins that bind FcγRIIb+ cells and coengage a target antigen on the cell's surface and an FcγRIIb on cell's surface. In one embodiment, the immunoglobulin binds with FcγRIIb, wherein the affinity of said binding has a Kd less than about 100 nM, e.g., less than or equal to about 95 nM, less than or equal to about 90 nM, less than or equal to about 85 nM, less than or equal to about 80 nM, less than or equal to about 75 nM, less than or equal to about 74 nM. In one embodiment, the immunoglobulin comprises an Fc region, wherein said Fc region comprises one or more modifications compared to a parent Fc region, wherein said modifications are at positions selected from the group consisting of 234, 235, 236, 237, 239, 265, 266, 267, 268, 298, 325, 326, 327, 328, 329, 330, 331, and 332, wherein numbering is according to the EU index. In another embodiment, the immunoglobulin is a bispecific antibody comprising a first Fv region and a second Fv region, wherein said first Fv region binds the target antigen, and said second Fv region binds FcγRIIb with a Kd of less than about 100 nM. In another embodiment, the immunoglobulin is an Fc fusion comprising an Fc region, wherein said Fc region binds FcγRIIb with a Kd of less than about 100 nM.

In some embodiments, the immunoglobulins that bind FcγRIIb+ cells and coengage a target antigen on the cell's surface and an FcγRIIb on cell's surface disclosed herein may bind and/or coengage a target antigen selected from the group consisting of: CD19, CD20, CD21 (CR2), CD22, CD23/FcεRII, FcεRI, (α, β, and γ subunits), CD24/BBA-1/HSA, CD27, CD35 (CR1), CD38, CD40, CD45RA, CD52/CAM-PATH-1/HE5, CD72, CD79a (Igα), CD79b (Igβ), IgM (μ), CD80, CD81, CD86, Leu13, HLA-DR, -DP, -DQ, CD138, CD317/HM1.24, CD11a, CD11b, CD11c, CD14, CD68, CD163, CD172a, CD200R, and CD206. In other embodiments, the immunoglobulins that bind FcγRIIb+ cells and coengage a target antigen on the cell's surface and an FcγRIIb on cell's surface disclosed herein may bind and/or coengage a target antigen selected from the group consisting of: IgM (μ), CD19, CD20, CD21, CD22, CD23, CD24, CD35, CD40, CD45RA, CD72, CD79a, CD79b, CD80, CD81, CD86, and HLA-DR. In one embodiment, immunoglobulins that bind FcγRIIb+ cells and coengage a target antigen on the cell's surface and an FcγRIIb on cell's surface disclosed herein may bind and/or coengage a target antigen selected from the group consisting of: IgM (μ), CD79a, CD79b, CD19, CD21, CD22, CD72, CD81, and Leu13. In one embodiment, immunoglobulins that bind FcγRIIb+ cells and coengage a target antigen on the cell's surface and an FcγRIIb on cell's surface disclosed herein may bind and/or coengage a target antigen selected from the group consisting of: IgM (μ), CD19, CD79a, CD79b, CD81, and HLA-DR. In another embodiment, immunoglobulins that bind FcγRIIb+ cells and coengage a target antigen on the cell's surface and an FcγRIIb on cell's surface disclosed herein may bind and/or coengage a target antigen selected from the group consisting of: CD22, CD40, and CD72.

In one embodiment, the immunoglobulins that bind FcγRIIb+ cells and coengage a target antigen on the cell's surface and an FcγRIIb on cell's surface disclosed herein may bind and/or coengage an autoantigen or allergen. In an alternate embodiment, an immunoglobulin disclosed herein may be an Fc fusion that is covalently linked to an autoantigen or allergen. In one embodiment, the autoantigen is selected from the group consisting citrullinated proteins and peptides such as CCP-1, CCP-2 (cyclical citrullinated peptides), fibrinogen, fibrin, vimentin, fillaggrin, collagen I and II peptides, alpha-enolase, translation initiation factor 4G1, perinuclear factor, keratin, Sa (cytoskeletal protein vimentin), components of articular cartilage such as collagen II, IX, and XI, circulating serum proteins such as RFs (IgG, IgM), fibrinogen, plasminogen, ferritin, nuclear components such as RA33/hnRNP A2, Sm, eukaryotic trasnlation elogation factor 1 alpha 1, stress proteins such as HSP-65, -70, -90, BiP, inflammatory/immune factors such as B7-H1, IL-1 alpha, and IL-8, enzymes such as calpastatin, alpha-enolase, aldolase-A, dipeptidyl peptidase, osteopontin, glucose-6-phosphate isomerase, receptors such as lipocortin 1, neutrophil nuclear proteins such as lactoferrin and 25-35 kD nuclear protein, granular proteins such as bactericidal permeability increasing protein (BPI), elastase, cathepsin G, myeloperoxidase, proteinase 3, platelet antigens, myelin protein antigen, islet cell antigen, rheumatoid factor, histones, ribosomal P proteins, cardiolipin, vimentin, nucleic acids such as dsDNA, ssDNA, and RNA, ribonuclear particles and proteins such as Sm antigens (including but not limited to SmD's and SmB'/B), U1RNP, A2/B1 hnRNP, Ro (SSA), and La (SSB) antigens.

In one embodiment, immunoglobulins that bind FcγRIIb+ cells and coengage a target antigen on the cell's surface and an FcγRIIb on cell's surface disclosed herein may be variant immunoglobulins relative to a parent immunoglobulin. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 239, 265, 266, 267, 268, 298, 325, 326, 327, 328, 329, 330, 331, and 332, wherein numbering is according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 239, 266, 267, 268, 325, 326, 327, 328, and 332, according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 266, 267, 268, 327, 328, according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 235, 236, 266, 267, 268, 328, according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 235, 236, 239, 266, 267, 268, and 328, according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 266, 267, 268, 327, 328, according to the EU index In one embodiment, said modification(s) is at least one substitution (e.g., one or more substitution(s), two or more substitution(s), etc.) selected from the group consisting of 234F, 234G, 234I, 234K, 234N, 234P, 234Q, 234S, 234V, 234W, 234Y, 234D, 234E, 235A, 235E, 235H, 235I, 235N, 235P, 235Q, 235R, 235S, 235W, 235Y, 235D, 235F, 235T, 236D, 236F, 236H, 236I, 236K, 236L, 236M, 236P, 236Q, 236R, 236S, 236T, 236V, 236W, 236Y, 236A, 236E, 236N, 237A, 237E, 237H, 237K, 237L, 237P, 237Q, 237S, 237V, 237Y, 237D, 237N, 239D, 239E, 239N, 239Q, 265E, 266D, 266I, 266M, 267A, 267D, 267E, 267G, 268D, 268E, 268N, 268Q, 298D, 298E, 298L, 298M, 298Q, 325L, 326A, 326E, 326W, 326D, 327D, 327G, 327L, 327N, 327Q, 327E, 328E, 328F, 328Y, 328H, 328I, 328Q, 328W, 329E, 330D, 330H, 330K, 330S, 331S, and 332E, wherein numbering is according to an EU index. In one embodiment, said modification(s) is at least one substitution (e.g., one or more substitution(s), two or more substitution(s), etc.) selected from the group consisting of 234N, 234F, 234D, 234E, 234W, 235Q, 235R, 235W, 235Y, 235D, 235F, 235T, 236D, 236H, 236I, 236L, 236S, 236Y, 236E, 236N, 237H, 237L, 237D, 237N, 239D, 239N, 239E, 266I, 266M, 267A, 267D, 267E, 267G, 268D, 268E, 268N, 268Q, 298E, 298L, 298M, 298Q, 325L, 326A, 326E, 326W, 326D, 327D, 327L, 327E, 328E, 328F, 328Y, 328H, 328I, 328Q, 328W, 330D, 330H, 330K, and 332E, wherein numbering is according to an EU index. In one embodiment, said modification(s) is at least one substitution (e.g., one or more substitution(s), two or more substitution(s), etc.) selected from the group consisting of 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E, wherein numbering is according to an EU index. In one embodiment, said modification(s) is at least one substitution (e.g., one or more substitution(s), two or more substitution(s), etc.) selected from the group consisting of L234E, L235Y, L235R, G236D, G236N, G237N, V266M, S267E, H268E, H268D, A327D, A327E, L328F, L328Y, L328W, wherein numbering is according to an EU index. In one embodiment, said modification(s) is at least one substitution (e.g., one or more substitution(s), two or more substitution(s), etc.) selected from the group consisting of 235Y, 236D, 239D, 266M, 267E, 268D, 268E, 328F, 328W, and 328Y, wherein numbering is according to an EU index. In one embodiment, said modification(s) is at least one substitution (e.g., one or more substitution(s), two or more substitution(s), etc.) selected from the group consisting of L235Y, G236D, V266M, S267E, H268E, H268D, L328F, L328Y, and L328W, wherein numbering is according to an EU index.

In one embodiment, said modification(s) is at least two modifications (e.g., a combination of modifications) at positions selected from the group consisting of 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332, wherein numbering is according to an EU index. In one embodiment, said modification(s) is at least two modifications (e.g., a combination of modifications) at positions selected from the group consisting of 235/267, 236/267, 239/268, 239/267, 267/268, and 267/328, wherein numbering is according to an EU index. In one embodiment, said modification(s) is at least two substitutions (e.g., a combination of substitutions) selected from the group consisting of 234D/267E, 234E/267E, 234F/267E, 234E/328F, 234W/239D, 234W/239E, 234W/267E, 234W/328Y, 235D/267E, 235D/328F, 235F/239D, 235F/267E, 235F/328Y, 235Y/236D, 235Y/239D, 235Y/267D, 235Y/267E, 235Y/268E, 235Y/328F, 236D/239D, 236D/267E, 236D/268E, 236D/328F, 236N/267E, 237D/267E, 237N/267E, 239D/267D, 239D/267E, 239D/268D, 239D/268E, 239D/327D, 239D/328F, 239D/328W, 239D/328Y, 239D/332E, 239E/267E, 266M/267E, 267D/268E, 267E/268D, 267E/268E, 267E/325L, 267E/327D, 267E/327E, 267E/328F, 267E/328I, 267E/328Y, 267E/332E, 268D/327D, 268D/328F, 268D/328W, 268D/328Y, 268D/332E, 268E/328F, 268E/328Y, 327D/328Y, 328F/332E, 328W/332E, and 328Y/332E, wherein numbering is according to an EU index.

In one embodiment, said modification(s) result in at least one of the following substitutions, or combinations of substitutions: 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/

239D/267E, 236D/239D/267E, 235Y/267E/268E, 236D/267E/268E, 239D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 239D/267E/332E, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E, wherein numbering is according to an EU index. In one embodiment, said modification(s) result in at least one of the following substitutions, or combinations of substitutions: 266D, 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 236D/267E, 236E/267E, 236N/267E, 237D/267E, 237N/267E, 266M/267E, 234E/268D, 236D/268D, 267D/268D, 267D/268E, 267E/268D, 267E/268E, 267E/325L, 267D/327D, 267D/327E, 267E/327E, 268D/327D, 239D/328Y, 267E/328F, 267E/328H, 267E/328I, 267E/328Q, 267E/328Y, 268D/328Y, 234D/236N/267E, 235Y/236D/267E, 234W/239E/267E, 235Y/239D/267E, 236D/239D/267E, 235Y/267E/268E, 236D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E, wherein numbering is according to an EU index. In one embodiment, said modification(s) result in at least one of the following substitutions, or combinations of substitutions: 234N, 235Q, 235R, 235W, 235Y, 236D, 236H, 236I, 236L, 236S, 236Y, 237H, 237L, 239D, 239N, 266I, 266M, 267A, 267D, 267E, 267G, 268D, 268E, 268N, 268Q, 298E, 298L, 298M, 298Q, 326A, 326E, 326W, 327D, 327L, 328E, 328F, 330D, 330H, 330K, 234F/236N, 234F/236D, 235D/239D, 234D/267E, 234E/267E, 234F/267E, 235D/267E, 235F/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327D, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/239D/267E, 236D/239D/267E, 235Y/267E/268E, 236D/267E/268E, 239D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 239D/267E/332E, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E In one embodiment, said modification(s) result in at least one of the following substitutions, or combinations of substitutions: 235Y/267E, 236D/267E, 239D/268D, 239D/267E, 267E/268D, 267E/268E, and 267E/328F, wherein numbering is according to an EU index.

In one embodiment, the modifications disclosed herein reduce affinity to at least one receptor relative to the parent immunoglobulin, wherein said receptor is selected from the group consisting of FcγRI, FcγRIIa, and FcγRIIIa. In an alternate embodiment, immunoglobulin variants disclosed herein mediate reduced ADCC or ADCP relative to the parent immunoglobulin.

Also disclosed herein are methods for engineering the novel immunoglobulin compositions.

Also disclosed herein are methods for screening target antigens for their capacity to mediate cellular inhibition via an FcγRIIb-dependent mechanism. In one embodiment, the antigen screening methods disclosed herein comprise the step of binding a cell that expresses the target antigen and FcγRIIb with an immunoglobulin that binds with enhanced affinity, e.g., the Kd of the immunoglobulin may be less than about 100 nM to at least FcγRIIb. In another embodiment, simultaneous binding of both target antigen and FcγRIIb by the immunoglobulin results in an inhibitory cellular response. In one embodiment of the screening methods disclosed herein, the cell is selected from the group consisting of: B cells, plasma cells, dendritic cells, macrophages, neutrophils, mast cells, basophils, or eosinophils. In another some screening methods disclosed herein, the immunoglobulin may be specific for the target antigen. In an alternate embodiment, immunoglobulin is specific for an antibody, wherein said antibody is specific for the target antigen. In an alternate embodiment, the immunoglobulin is specific for a hapten, and wherein either the target antigen, or an antibody or protein that is specific for the target antigen is haptenized.

Also disclosed herein are isolated nucleic acids encoding the immunoglobulins described herein. Also disclosed herein are vectors comprising the nucleic acids, optionally, operably linked to control sequences. Also disclosed herein are host cells containing the vectors, and methods for producing and optionally recovering the immunoglobulin compositions.

Also disclosed herein are immunoglobulin polypeptides, that comprise the immunoglobulins disclosed herein. The immunoglobulin polypeptides may find use in a therapeutic product. In one embodiment, the immunoglobulin polypeptides disclosed herein may be antibodies.

Also disclosed are compositions comprising immunoglobulin polypeptides described herein, and a physiologically or pharmaceutically acceptable carrier or diluent.

Also described are therapeutic and diagnostic uses for the immunoglobulin polypeptides disclosed herein. In one embodiment, the immunoglobulins disclosed herein are used to treat one or more autoimmune disease or inflammatory disease. In an alternate embodiment, the immunoglobulins disclosed herein are used to treat one or more hematological malignancies.

BRIEF DESCRIPTION OF THE DRAWINGS

Figure 1A:
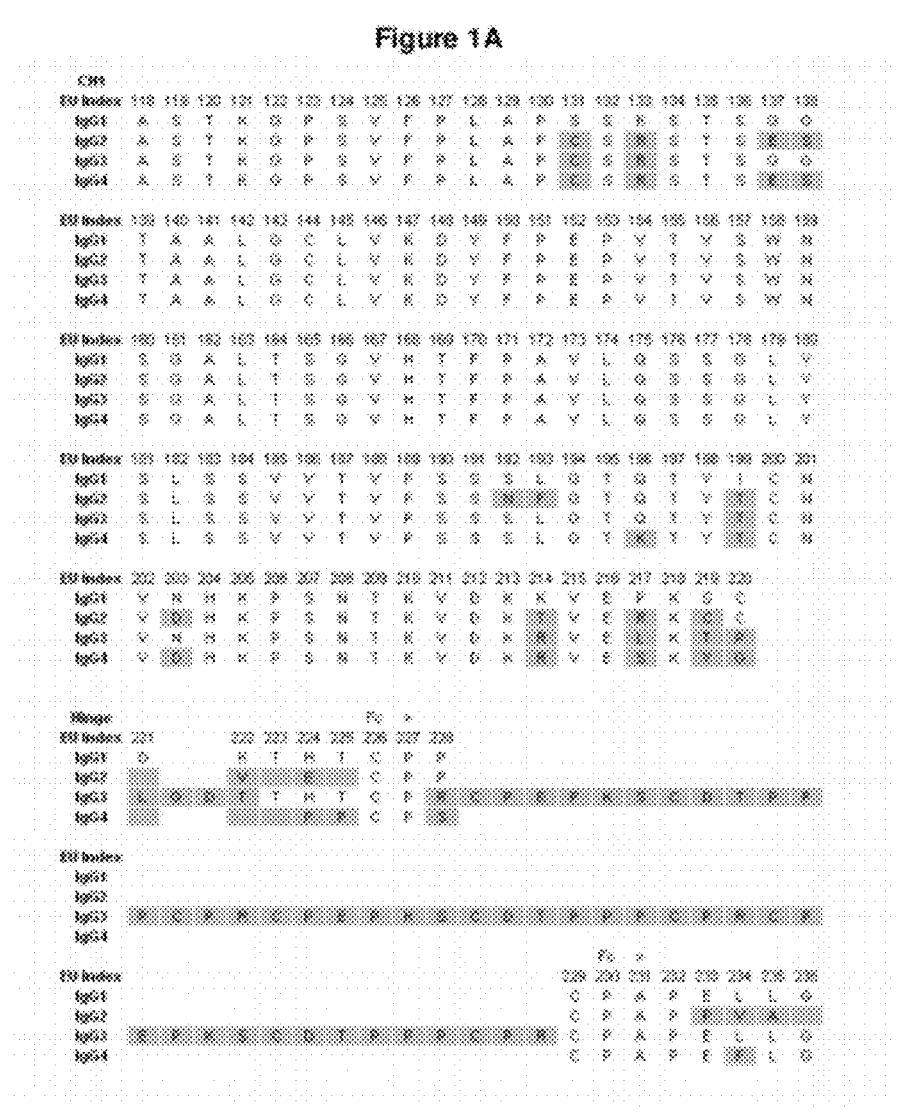
Figure 1B:
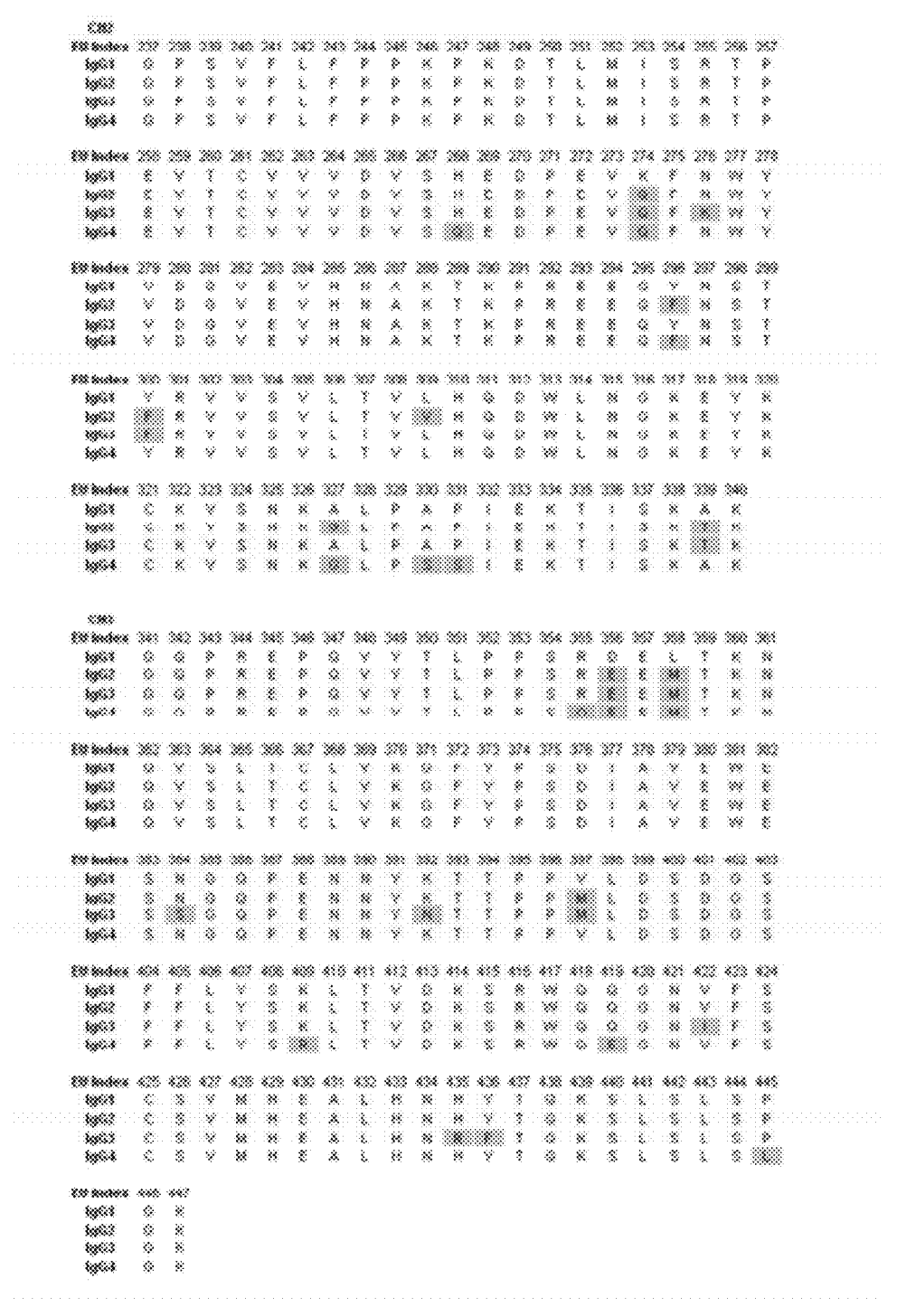

FIG. 1. Alignment of the amino acid sequences of the human IgG immunoglobulins IgG1, IgG2, IgG3, and IgG4. FIG. 1A provides the sequences of the CH1 (Cγ1) and hinge domains, and FIG. 1B provides the sequences of the CH2 (Cγ2) and CH3 (Cγ3) domains. Positions are numbered according to the EU index of the IgG1 sequence, and differences between IgG1 and the other immunoglobulins IgG2, IgG3, and IgG4 are shown in gray. Allotypic polymorphisms exist at a number of positions, and thus slight differences between the presented sequences and sequences in the prior art may exist. The possible beginnings of the Fc region are labeled, defined herein as either EU position 226 or 230.

FIG. 2. Common haplotypes of the human gamma1 (FIG. 2A) and gamma2 (FIG. 2B) chains.

FIG. 3. Novel methods of inhibiting B cell activation. Here CR represents a co-receptor of the BCR complex, but could be any antigen expressed on any FcγRIIb+ cell.

FIG. 4. FcγR positions that contribute to FcγRIIb and FcγRIIIa binding selectivity. Positions were identified by evaluating proximity to the FcγR/Fc interface and amino acid dissimilarity between FcγRIIb and FcγRIIIa.

FIG. 5. Fc positions proximal to FcγR positions contributing to FcγRIIb and FcγRIIIa binding selectivity, as listed in FIG. 6.

FIG. 6. Biacore surface plasmon resonance sensorgrams showing binding of Fc variant anti-CD19 antibodies to human FcγRIIb.

FIG. 7. Affinities of Fc variant antibodies for human FcγRs as determined by Biacore surface plasmon resonance. FIG. 7A is a table listing the dissociation constant (Kd) for binding anti-CD19 variant antibodies to human FcγRI, FcγRIIa (131 R), FcγRIIa (131 H), FcγRIIb, FcγRIIIa (158V), and FcγRIIIa (158F). FIG. 7B is a continuation of the list in FIG. 7A. FIG. 7C is a continuation of the list in FIG. 7A and FIG. 7B. FIG. 7D is a continuation of the list in FIG. 7A, FIG. 7B, and FIG. 7C. Multiple observations have been averaged. n.d.=no detectable binding.

FIG. 8. Fold affinities of Fc variant antibodies for human FcγRs as determined by Biacore surface plasmon resonance. FIG. 8A is a table listing the fold improvement or reduction in affinity relative to WT IgG1 for binding of anti-CD19 variant antibodies to human FcγRI, FcγRIIa (131 R), FcγRIIa (131 H), FcγRIIb, FcγRIIIa (158V), and FcγRIIIa (158F). FIG. 8B is a continuation of the list in FIG. 8A. FIG. 8C is a continuation of the list in FIG. 8A and FIG. 8B. FIG. 8D is a continuation of the list in FIG. 8A, FIG. 8B, and FIG. 8C. Fold=KD(Native IgG1)/KD(variant). n.d.=no detectable binding.

FIG. 9. Affinities of Fc variant antibodies for human FcγRs as determined by Biacore surface plasmon resonance. The graph shows the −log(KD) for binding of anti-CD19 variant and WT IgG1 antibodies to human FcγRI (I), R131 FcγRIIa (RIIa), H131 FcγRIIa (HIIa), FcγRIIb (IIb), and V158 FcγRIIIa (VIIIa). Binding of L235Y/S267E, G236D/S267E, and S267E/L328F to V158 FcγRIIIa was not detectable.

FIG. 10. Affinities of Fc variant antibodies for human FcγRs as determined by Biacore surface plasmon resonance. The graph shows the −log(KD) for binding of anti-CD19 variant and WT IgG1 antibodies to human FcγRI (I), R131 FcγRIIa (RIIa), H131 FcγRIIa (HIIa), FcγRIIb (lib), and V158 FcγRIIIa (VIIIa).

FIG. 11. Analysis of combination variants (doubles, triples) for synergistic and non-additive effects in binding to human FcγRIIb (A), FcγRI (B), R131 FcγRIIa (C), H131 FcγRIIa (D), and V158 FcγRIIIa (E). The ratio between actual fold improvement measured by SPR and expected fold improvement calculated by multiplying the fold improvements of the single substitution variants is plotted. Ratios greater than one indicate a synergistic effect.

FIG. 12. Binding of Fc variant antibodies to human FcγRs relative to WT IgG1 as measured by cell surface binding. Antibodies (variant and WT IgG1) were added to HEK293T cells transfected with FcγRIIb to assess cell surface binding. The binding curves were constructed by plotting MFI as a function of Fc variant concentration.

FIG. 13. Affinities of Fc variant antibodies for mouse and cynologous monkey (Macaca fascicularis) FcγRs as determined by Biacore surface plasmon resonance, either by dissociation constant (Kd) or off-rate determination as indicated. FIG. 13A is a table listing the fold improvement relative to WT IgG1 for binding of anti-CD19 antibody variants to mouse FcγRI, mouse FcγRII, mouse FcγRIII, mouse FcγRIV, cynomolgus monkey FcγRI, cynomolgus monkey FcγRIIa, cynomolgus monkey FcγRIIb, and cynomolgus monkey FcγRIIIa. FIG. 13B is a continuation of the list in FIG. 13A. FIG. 13C is a continuation of the list in FIG. 13A and FIG. 13B. FIG. 13D is a continuation of the list in FIG. 13A, FIG. 13B, and FIG. 13C. NB=no detectable binding.

FIG. 14. Affinities of Fc variant antibodies for human FcγRs as determined by Biacore surface plasmon resonance. The graph shows the −log(KD) for binding of anti-CD19 variant and WT IgG1 antibodies to human FcγRI (I), R131 FcγRIIa (RIIa), H131 FcγRIIa (HIIa), FcγRIIb (IIb), and V158 FcγRIIIa (VIIIa).

FIG. 15. ATP-dependent B cell viability assay demonstrating the survival of primary human B cells upon BCR activation, here carried out by crosslinking with anti-mu (A) or anti-CD79b (B) antibodies.

FIG. 16. Inhibition of B cell proliferation by Fc variant anti-CD19 antibodies. Anti-RSV (Respiratory Syncytial Virus) S267E/L328F is used as a control (RSV is not expressed on B cells). An ATP-dependent luminescence assay was used to measure B cell proliferation in the presence of 10 μg/ml anti-CD79b activating antibody, and the effect of anti-CD19-S267E/L328F was compared to anti-CD19-IgG1 (native IgG1 Fv control) and anti-RSV-S267E/L328F (non-CD19 Fc control). To assess the importance of CD19 and FcγRIIb coengagement, anti-RSV-S267E/L328F alone or in combination with anti-CD19-IgG1 was used.

Figure 17:
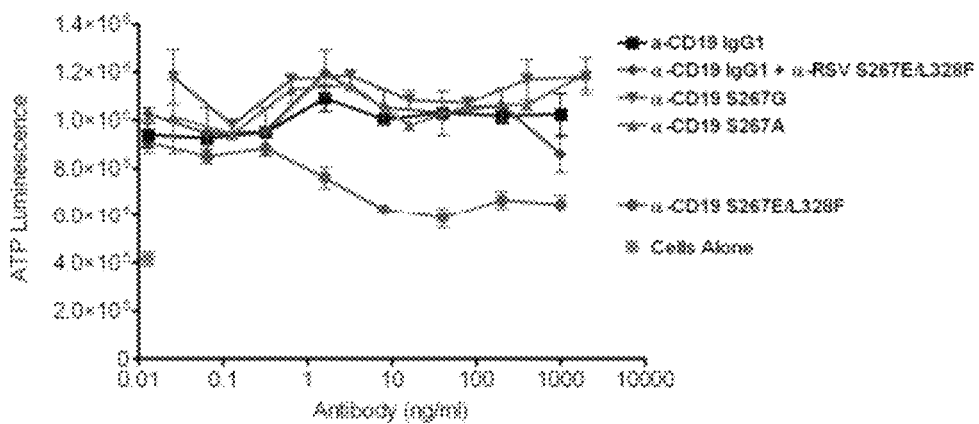

FIG. 17. Inhibition of B cell proliferation by Fc variant anti-CD19 antibodies. An ATP-dependent luminescence assay was used to measure proliferation of primary human B cells in the presence of 1 μg/ml anti-CD79b activating antibody, and varying concentrations of the indicated anti-CD19 or anti-RSV control antibodies.

Figure 18:
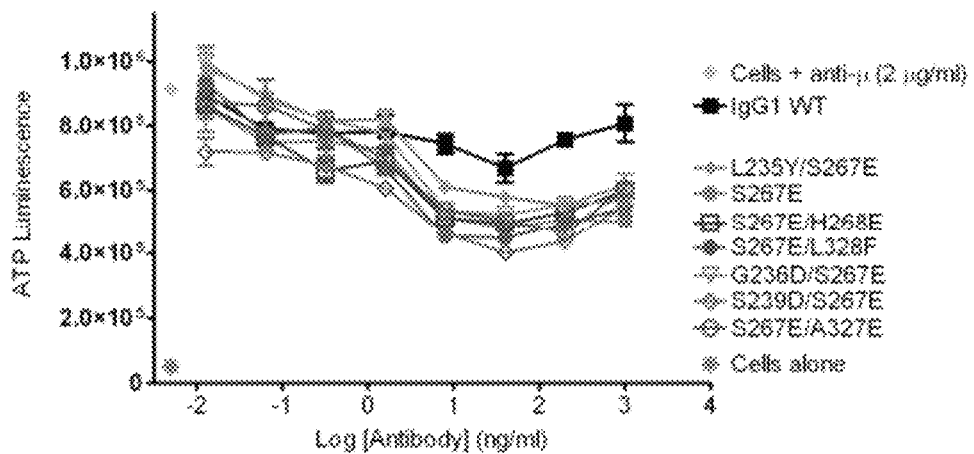

FIG. 18. Inhibition of B cell proliferation by Fc variant anti-CD19 antibodies. An ATP-dependent luminescence assay was used to measure proliferation of primary human B cells in the presence of 2 μg/ml anti-μ (mu) antibody and varying concenrations of the indicated anti-CD19 antibodies.

FIG. 19. Coengagement of FcγRIIb and CD19 by IIbE variants inhibits BCR activation-induced calcium mobilization in primary human B cells. Calcium mobilization was induced with 10 μg/ml anti-CD79b BCR-activating antibody. Calcium mobilization was measured in the presence of 10 μg/ml fixed concentration of anti-CD19 IIbE variants, a-CD19-IgG1 (native IgG1 Fv control), α-FITC-S267E/L328F (non-CD19 Fc control), or PBS vehicle. The data are plotted as the change of MFI over time, or the area under the response curve normalized to the maximum measured signal intensity.

FIG. 20. Coengagement of FcγRIIb and CD19 by IIbE variants inhibits BCR activation-induced calcium mobilization in primary human B cells. Calcium mobilization was induced with 10 μg/ml anti-CD79b BCR-activating antibody. Calcium mobilization was measured at multiple antibody concentrations for anti-CD19-IgG1 and three IIbE variants, and the areas under the curves were plotted to obtain dose-response relationships.

FIG. 21. Correlation between affinity for FcγRIIb and inhibition of calcium release. EC50 data are from FIG. 20, and symbols are the same as indicated in FIG. 22. Affinities are from Biacore data presented in FIG. 7A-FIG. 7D.

FIG. 22. Coengagement of FcγRIIb and CD19 by IIbE variants inhibits BCR activation-induced calcium mobilization in primary human B cells. Calcium mobilization was induced with 10 µg/ml anti-CD79b BCR-activating antibody. Soluble FcγRI (50 µg/ml) added to 10 µg/ml α-CD19-S267E/L328F completely abolished the IIbE variant's inhibitory effect on calcium mobilization, confirming the importance of FcγRIIb engagement by anti-CD19 antibody.

Figure 23:
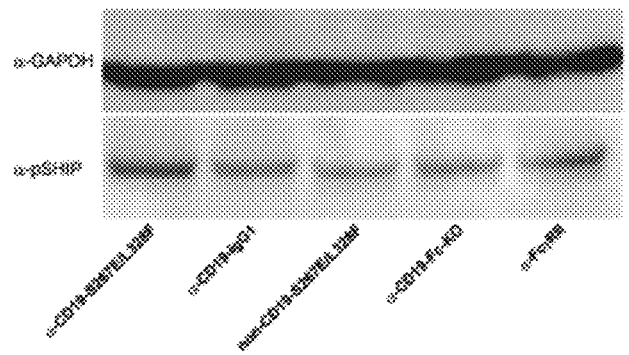

FIG. 23. IIbE variant anti-CD19-S267E/L328F activates FcγRIIb-mediated SHIP phosphorylation in primary human B cells. Anti-CD19-S267E/L328F, anti-CD19-IgG1 (Fv control), anti-RSV-S267E/L328F (Fc control), anti-CD19-Fc KO (Fv control), or anti-FcγRII (10 µg/ml each) were added to B cells in the presence of 20 µg/ml anti-CD79b antibody. As a positive control, 20 µg/ml goat anti-mouse IgG F(ab')2 fragment was used to crosslink anti-CD79b and anti-FcγRII antibodies. A blot of total cellular extracts was probed with anti-pSHIP, with anti-GAPDH used as a loading control. Relative to negative controls, anti-CD19-S267E/L328F induced greater SHIP1 phosphorylation than direct crosslinking of BCR and FcγRIIb by CD79b and FcγRIIb antibodies.

Figure 24:
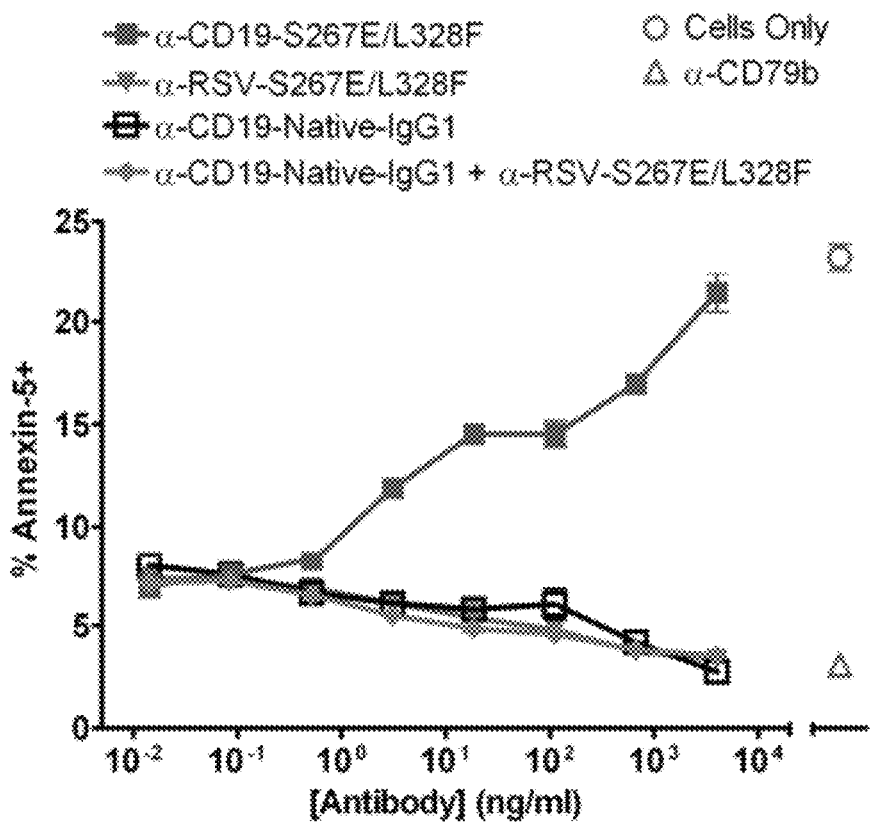

FIG. 24. Anti-CD19-S267E/L328F inhibits the anti-apoptotic effects of BCR activation on primary human B cells. Inhibition of BCR-mediated survival signals by FcγRIIb and CD19 coengagement was examined using annexin-V staining in the presence of 10 µg/ml anti-CD79b. B cell apoptosis was stimulated by anti-CD19-S267E/L328F, but not anti-CD19-IgG1 (Fv control), anti-RSV-S267E/L328F (Fc control), or the two controls combined.

FIG. 25. NK-cell mediated ADCC activity of Fc variant antibodies against Ramos B cells.

FIG. 26. Macrophage mediated phagocytosis (ADCP) activity of Fc variant antibodies against RS4;11 B cells.

FIG. 27. Fc variant anti-CD19 antibodies do not mediate CDC activity against Raji B cells.

FIG. 28: Evaluation of the capacity of co-engagement of CD19 and FcγRIIb to inhibit human B cell activation in vivo. (A) Schematic representation of the experimental protocol. (B) Titer of anti-tetanus toxoid (TT) specific antibody in huPBL-SCID mice after TT immunization and treatment with vehicle (PBS), anti-CD19 IgG1 WT, anti-CD19 with enhanced FcγRIIb affinity (a-CD19 S267E/L328F), or anti-CD20 (Rituximab).

FIG. 29. Target antigens that may be effective FcγRIIb co-targets for modulation of cellular activity. B=B cells, Plasma=plasma cells, DC=dendritic cells, MΦ=macrophages, PMN=neutrophils, Baso=basophils, Eos=eosinophils, and Mast=mast cells.

FIG. 30. ATP-dependent luminescence assay measuring B cell proliferation in the presence of 1 µg/ml anti-CD79b-SN8-G236R/L328R antibody, and varying concentrations of either enhanced FcγRIIb variant (S267E/L328F) or FcγR knockout variant (G236R/L328R or ^236R/L328R) versions of anti-CD20 (clone PRO70769), -CD52 (Campath), and -CD19 (HuAM4G7) antibodies.

FIG. 31. ATP-dependent luminescence assay measuring B cell proliferation in the presence of 2 µg/ml anti-µ antibody, and varying concentrations of either enhanced FcγRIIb variant (S267E/L328F), FcγR knockout variant (G236R/L328R), or WT IgG1 versions of anti-CD23 antibodies (clone 5E8 or C11).

FIG. 32. ATP-dependent luminescence assay measuring B cell proliferation in the presence of 2 µg/ml anti-µ antibody, and either enhanced FcγRIIb variant (S267E/L328F), FcγR knockout variant (G236R/L328R), or WT IgG1 versions of the anti-CD79b antibody SN8.

FIG. 33. ATP-dependent luminescence assay measuring B cell proliferation in the presence of 2 µg/ml anti-µ antibody, and varying concentrations of either enhanced FcγRIIb variant (S267E/L328F), FcγR knockout variant (G236R/L328R), or WT IgG1 versions of anti-CD22 antibody.

FIG. 34. ATP-dependent luminescence assay measuring B cell proliferation in the presence of BCR stimulation by (A) 1 µg/ml anti-CD79b-SN8-G236R/L328R antibody or (B) 2 µg/ml anti-µ antibody, and varying concentrations of either enhanced FcγRIIb variant (S267E/L328F), FcγR knockout variant (G236R/L328R), or WT IgG1 versions of anti-CD40 antibodies (clones PFCD40, S2C6, G28.5, and 5D12).

FIG. 35. ATP-dependent luminescence assay measuring B cell proliferation in the presence of 1 µg/ml anti-CD79b-SN8-G236R/L328R antibody, and varying concentrations of either enhanced FcγRIIb variant (S267E/L328F) or FcγR knockout variant (G236R/L328R or ^236R/L328R) versions of anti-CD19 antibodies (clones HD37, 21D4, or HuAM4G7.

FIG. 36. Calcium release assay measuring inhibition capacity of variant antibodies with specificity for CD22 (A), CD23 (B), CD40 (C), and CD79b (D). Calcium mobilization was induced with 10 µg/ml anti-CD79b-SN8-G236R/L328R antibody, and monitored in the presence of either enhanced FcγRIIb variant (S267E/L328F) or FcγR knockout variant (G236R/L328R) versions of anti-CD22, -CD23, -CD40, and CD79b antibodies.

Figure 37:
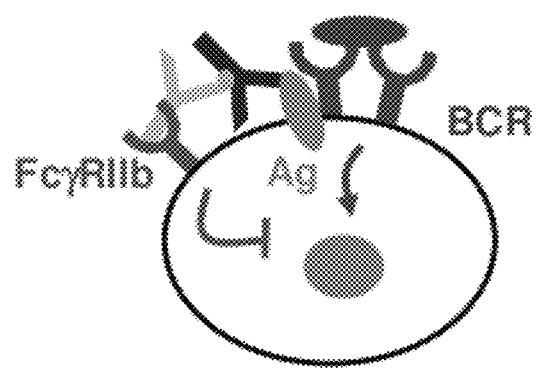

FIG. 37. Hapten approach to screening target antigens for capacity to modulate cellular activity upon high affinity co-targeting with FcγRIIb.

FIG. 38. ATP-dependent luminescence assay measuring B cell proliferation in the presence of 2 µg/ml FITCylated anti-µ F(ab')2 and varying concentrations of either enhanced FcγRIIb variant (S267E/L328F), FcγR knockout variant (G236R/L328R or ^236R/L328R), or WT IgG1 versions of anti-FITC antibody (clone 4-4-20). Anti-RSV was included as a control.

FIG. 39. ATP-dependent luminescence assay measuring B cell proliferation in the presence of 2 µg/ml anti-µ F(ab')2, 0.5 µg/ml FITC-labeled anti-CD19 (clone murine 4G7 IgG1), and varying concentrations of either enhanced FcγRIIb variant (S267E/L328F), FcγR knockout variant (^236R/L328R), or WT IgG1 versions of anti-FITC antibody.

FIG. 40. ATP-dependent luminescence assay measuring B cell proliferation in the presence of 2 µg/ml anti-µ F(ab')2, 0.5 µg/ml FITC-labeled anti-CD20 clone PDR-79 (A) or 1 µg/ml FITC-labeled Rituxan (B), and varying concentrations of either enhanced FcγRIIb variant (^267E/L328F), FcγR knockout variant (^236R/L328R), or WT IgG1 versions of anti-FITC antibody. FITC-labeled anti-mu at 2 µg/ml is also included in (B) as a control.

FIG. 41. ATP-dependent luminescence assay measuring B cell proliferation in the presence of 1 µg/ml anti-CD79b (SN8) antibody, 0.5 µg/ml FITC-labeled anti-CD21, and varying concentrations of either enhanced FcγRIIb variant (S267E/L328F) or WT IgG1 versions of anti-FITC antibody.

FIG. 42. ATP-dependent luminescence assay measuring B cell proliferation in the presence of 1 µg/ml anti-CD79b (SN8) antibody, 0.5 µg/ml FITC-labeled anti-CD24, and varying concentrations of either enhanced FcγRIIb variant (S267E/L328F) or WT IgG1 versions of anti-FITC antibody.

Figure 43:
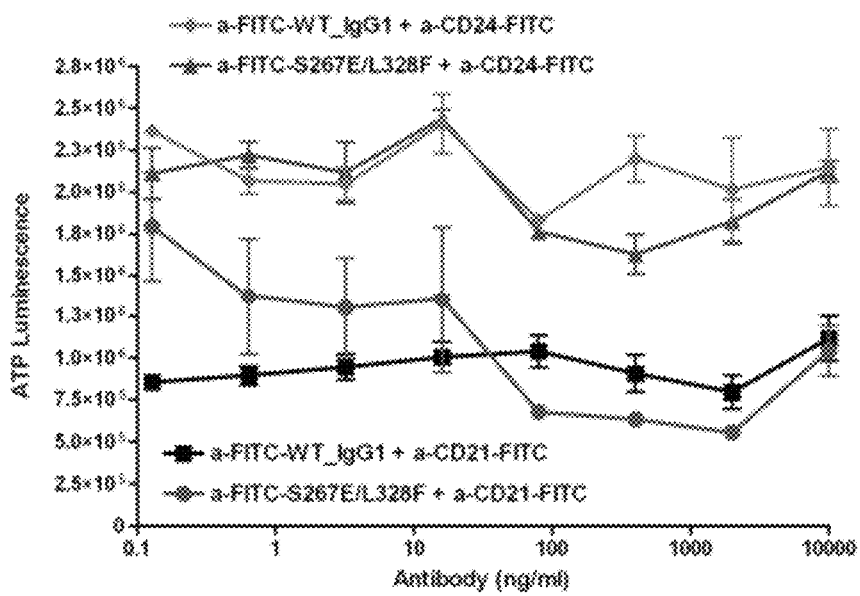

FIG. 43. ATP-dependent luminescence assay measuring B cell proliferation in the presence of 2 μg/ml anti-μ F(ab')2, 0.25 μg/ml FITC-labeled anti-CD1 or 0.5 μg/ml FITC-labeled anti-CD24, and varying concentrations of either enhanced FcγRIIb variant (S267E/L328F) or WT IgG1 versions of anti-FITC antibody.

Figure 44:
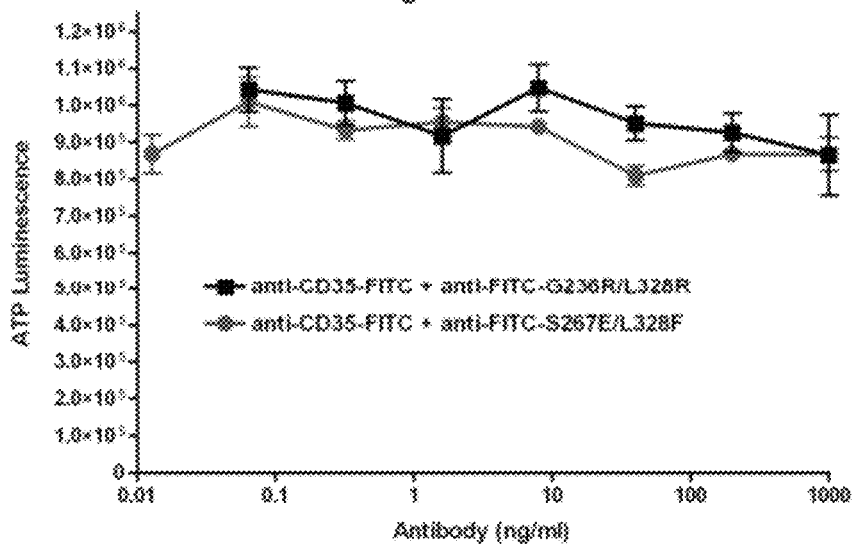

FIG. 44. ATP-dependent luminescence assay measuring B cell proliferation in the presence of 1 μg/ml anti-CD79b (SN8) antibody, FITC-labeled anti-CD35, and varying concentrations of either enhanced FcγRIIb variant (S267E/L328F) or FcγR knockout (G236R/L328R) versions of anti-FITC antibody.

Figure 45:
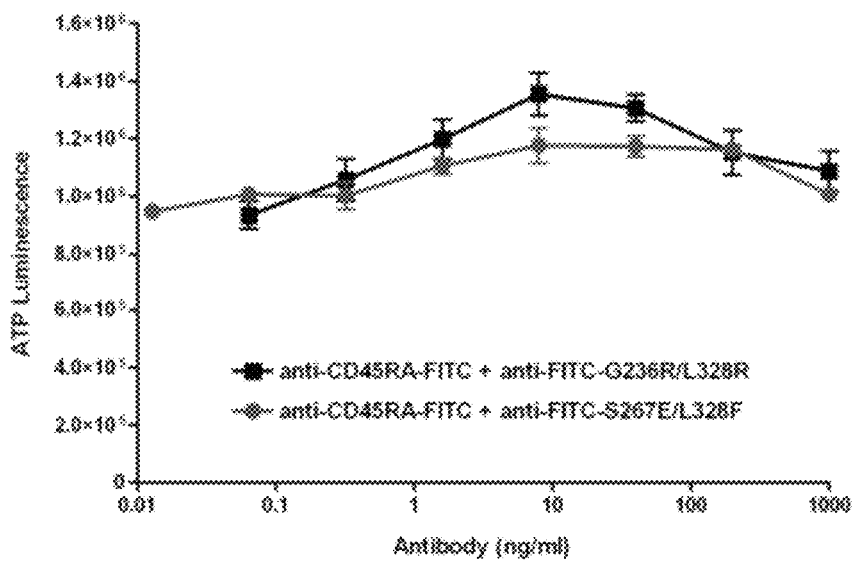

FIG. 45. ATP-dependent luminescence assay measuring B cell proliferation in the presence of 1 μg/ml anti-CD79b (SN8) antibody, FITC-labeled anti-CD45RA, and varying concentrations of either enhanced FcγRIIb variant (S267E/L328F) or FcγR knockout (G236R/L328R) versions of anti-FITC antibody.

Figure 46:
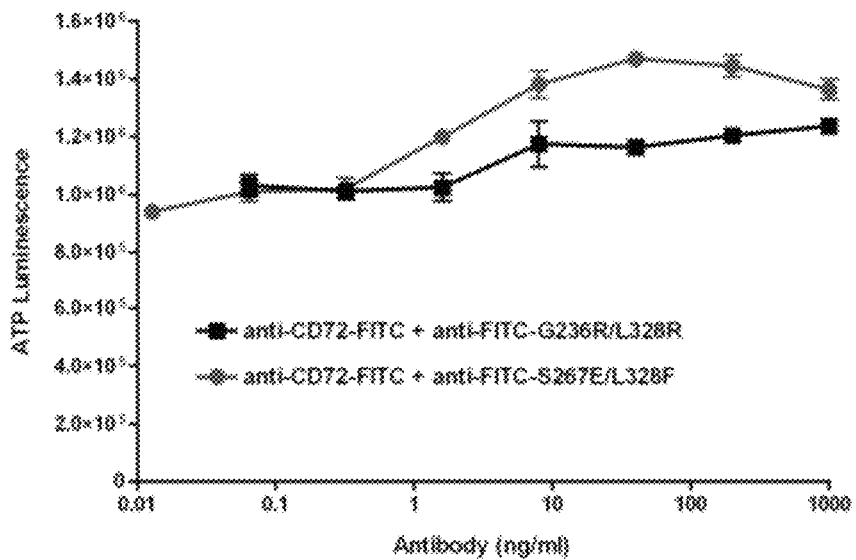

FIG. 46. ATP-dependent luminescence assay measuring B cell proliferation in the presence of 1 μg/ml anti-CD79b (SN8) antibody, FITC-labeled anti-CD72, and varying concentrations of either enhanced FcγRIIb variant (S267E/L328F) or FcγR knockout (G236R/L328R) versions of anti-FITC antibody.

Figure 47:
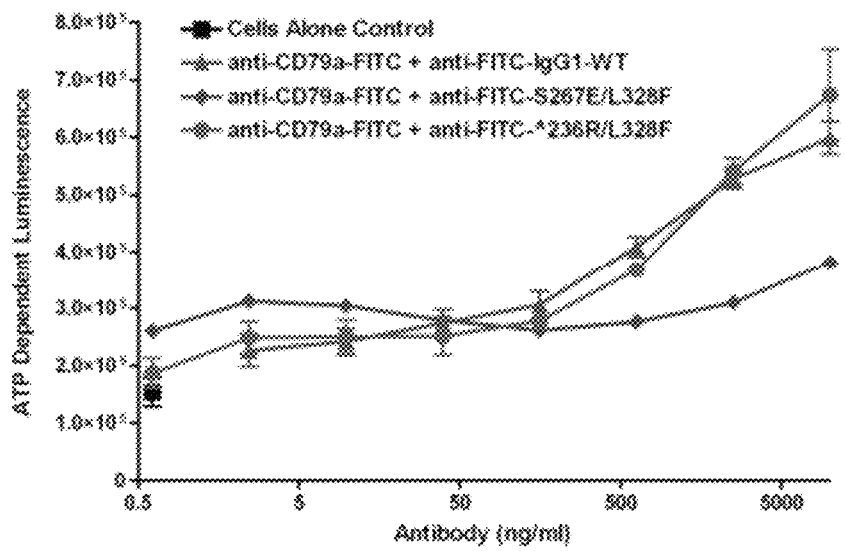

FIG. 47. ATP-dependent luminescence assay measuring B cell proliferation in the presence of 2 μg/ml anti-μ F(ab')2, 2 μg/ml FITC-labeled anti-CD79a (clone ZL7-4), and varying concentrations of either enhanced FcγRIIb variant (S267E/L328F), FcγR knockout (^236R/L328R) or WT IgG1 versions of anti-FITC antibody.

Figure 48:
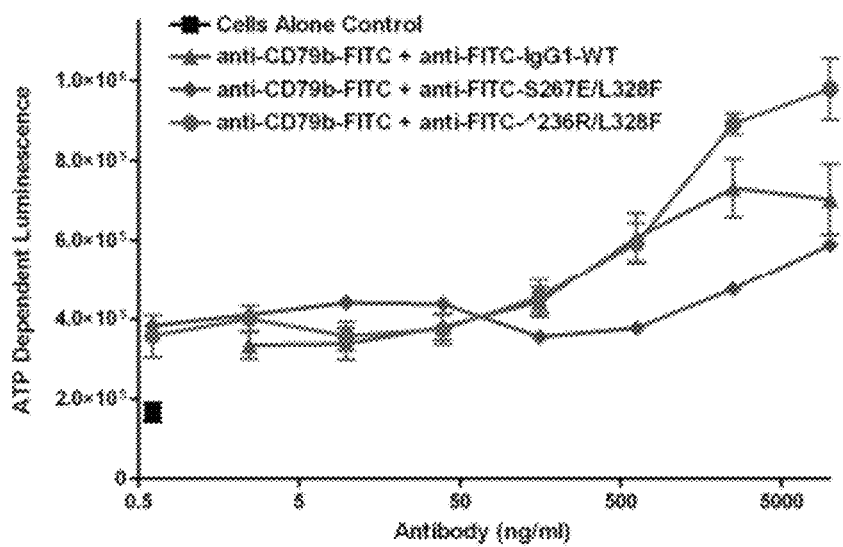

FIG. 48. ATP-dependent luminescence assay measuring B cell proliferation in the presence of 2 μg/ml anti-μ F(ab')2, 1.8 μg/ml FITC-labeled anti-CD79b (clone ZL9-3), and varying concentrations of either enhanced FcγRIIb variant (S267E/L328F), FcγR knockout (^236R/L328R) or WT IgG1 versions of anti-FITC antibody.

Figure 49:
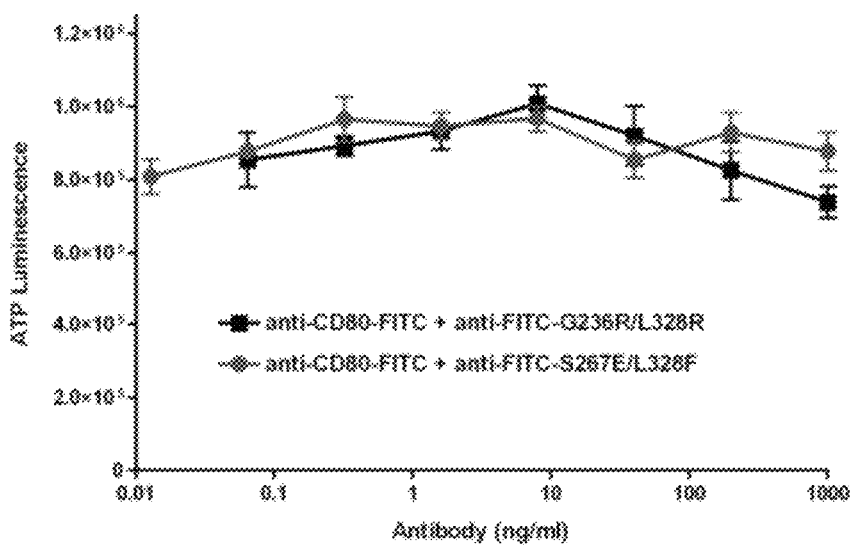

FIG. 49. ATP-dependent luminescence assay measuring B cell proliferation in the presence of 1 μg/ml anti-CD79b (SN8) antibody, FITC-labeled anti-CD80, and varying concentrations of either enhanced FcγRIIb variant (S267E/L328F) or FcγR knockout (G236R/L328R) versions of anti-FITC antibody.

Figure 50:
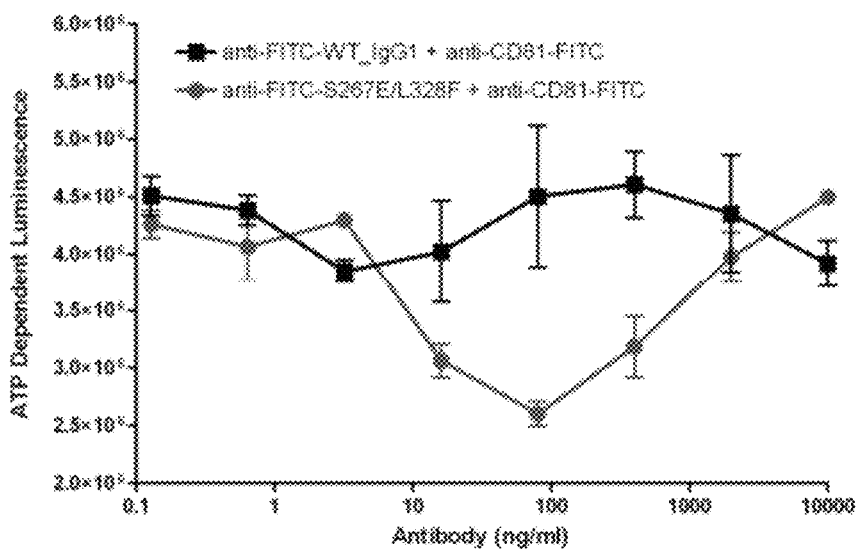

FIG. 50. ATP-dependent luminescence assay measuring B cell proliferation in the presence of FITC-labeled anti-CD81, varying concentrations of either enhanced FcγRIIb variant (S267E/L328F), FcγR knockout variant (G236R/L328R), or WT IgG1 versions of anti-FITC antibody, and 2 μg/ml anti-μ antibody.

FIG. 51. ATP-dependent luminescence assay measuring B cell proliferation in the presence of 1 μg/ml anti-CD79b (SN8)-G236R/L328R antibody, FITC-labeled anti-CD86, and varying concentrations of either enhanced FcγRIIb variant (S267E/L328F) or FcγR knockout (G236R/L328R) versions of anti-FITC antibody.

FIG. 52. ATP-dependent luminescence assay measuring B cell proliferation in the presence of 1 μg/ml anti-CD79b (SN8)-G236R/L328R antibody, FITC-labeled anti-HLA-DR, and varying concentrations of either enhanced FcγRIIb variant (S267E/L328F) or FcγR knockout (G236R/L328R) versions of anti-FITC antibody.

FIG. 53. Summary of results from target antigen screening for capacity of antigens to modulate B cell activation when co-targeted with high affinity FcγRIIb binding. Results are from the ATP-dependence luminscence B cell viability assay or calcium mobilization assay using either Fc variant versions of antibodies with specificity for the indicated target antigens (Fc variant approach) or Fc variant versions of the anti-FITC antibody together with commercial antibodies with specificity for the indicated target antigens (Hapten approach)

FIG. 54. FIG. 54A lists the amino acid sequences of various variable regions, heavy chain constant regions, and full length antibodies. FIG. 54B is a continuation of the list in FIG. 54A. FIG. 54C is a continuation of the list in FIG. 54A and FIG. 54B. FIG. 54D is a continuation of the list in FIG. 54A, FIG. 54B, and FIG. 54C.

DETAILED DESCRIPTION OF EXEMPLARY EMBODIMENTS

The humoral immune response (e.g., the result of diverse B cell responses) may be initiated when B cells are activated by an antigen and subsequently differentiated into plasma cells. Binding of membrane bound B cell receptor (BCR) on B cells by an antigen activates an intracellular signaling cascade, including calcium mobilization, which leads to cell proliferation and differentiation. Coengagement of cognate BCR) with the inhibitory Fc receptor (FcγRIIb) inhibits B cell activation signals through a negative feedback loop.

The importance of FcγRIIb in negative regulation of B cell responses has been demonstrated using FcγRIIb-deficient mice, which fail to regulate humoral responses (Wernersson, S. et al., 1999, J. Immunol. 163, 618-622), are sensitized to collagen-induced arthritis (Yuasa, T. et al., 1999, J. Exp. Med. 189, 187-194), and develop lupus-like disease (Fukuyama, H. et al., J. V., 2005, Nat. Immunol. 6, 99-106; McGaha, T. L. et al., 2005, Science 307, 590-593) and Goodpasture's syndrome (Nakamura, A. et al., 2000, J. Exp. Med. 191, 899-906). FcγRIIb dysregulation has also been associated with human autoimmune disease. For example, polymorphisms in the promoter (Blank, M. C. et al., 2005, Hum. Genet. 117, 220-227; Olferiev, M. et al., 2007, J. Biol. Chem. 282, 1738-1746) and transmembrane domain (Chen, J. Y. et al., 2006, Arthritis Rheum. 54, 3908-3917; Floto, R. A. et al., Nat. Med. 11, 1056-1058; Li, X. et al., 2003, Arthritis Rheum. 48, 3242-3252) of FcγRIIb have been linked with increased prevalence of systemic lupus erythematosus (SLE). SLE patients also show reduced FcγRIIb surface expression on B cells (Mackay, M. et al., 2006, J. Exp. Med. 203, 2157-2164; Su, K. et al., 2007, J. Immunol. 178, 3272-3280) and, as a consequence, exhibit dysregulated calcium signaling (Mackay, M. et al., 2006, J. Exp. Med. 203, 2157-2164). The pivotal role of FcγRIIb in regulating B cells, supported by mouse models and clinical evidence, makes it an attractive therapeutic target for controlling autoimmune and inflammatory disorders (Pritchard, N. R. & Smith, K. G., 2003, Immunology 108, 263-273; Ravetch, J. V. & Lanier, L. L., 2000, Science 290, 84-89; Stefanescu, R. N. et al., 2004, J. Clin. Immunol. 24, 315-326).

Described herein are antibodies that mimic the inhibitory effects of coengagement of cognate BCR with FcγRIIb on B cells. For example, describe herein are variant anti-CD19 antibodies engineered such that the Fc domain binds to FcγRIIb with up to ~430-fold greater affinity. Relative to native IgG1, the FcγRIIb binding-enhanced (IIbE) variants strongly inhibit BCR-induced calcium mobilization and viability in primary human B cells. Inhibitory effects involved phosphorylation of SH2-containing inositol polyphosphate 5-phosphatase (SHIP), which is known to be involved in FcγRIIb-induced negative feedback of B cell activation. Coengagement of BCR and FcγRIIb by IIbE variants also overcame the anti-apoptotic effects of BCR activation. The use of a single antibody to suppress B cell functions by coengagement of cognate BCR and FcγRIIb may represent a novel approach in the treatment of B cell-mediated diseases. Nonlimiting examples of B cell-mediated diseases include hematological malignancies, autoimmunity, allergic responses, etc.

Described herein are several definitions. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antibody" herein is meant a protein consisting of one or more polypeptides substantially encoded by all or part of the recognized immunoglobulin genes. The recognized immunoglobulin genes, for example in humans, include the kappa (K), lambda (A), and heavy chain genetic loci, which together comprise the myriad variable region genes, and the constant region genes mu (v), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

By "amino acid" and "amino acid identity" as used herein is meant one of the 20 naturally occurring amino acids or any non-natural analogues that may be present at a specific, defined position.

By "CD32b$^+$ cell" or "FcγRIIb$^+$ cell" as used herein is meant any cell or cell type that expresses CD32b (FcγRIIb). CD32b+ cells include but are not limited to B cells, plasma cells, dendritic cells, macrophages, neutrophils, mast cells, basophils, or eosinophils.

By "CDC" or "complement dependent cytotoxicity" as used herein is meant the reaction wherein one or more complement protein components recognize bound antibody on a target cell and subsequently cause lysis of the target cell.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of Cκ or Cλ, wherein numbering is according to the EU index. By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC. Further, effector functions include FcγRIIb-mediated effector functions, such as inhibitory functions (e.g., down-regulating, reducing, inhibiting etc., B cell responses, e.g., a humoral immune response).

By "effector cell" as used herein is meant a cell of the immune system that expresses one or more Fc and/or complement receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys.

By "Fab" or "Fab region" as used herein is meant the polypeptides that comprise the $V_H$, CH1, $V_H$, and $C_L$ immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below.

By "Fc polypeptide" as used herein is meant a polypeptide that comprises all or part of an Fc region. Fc polypeptides include antibodies, Fc fusions, isolated Fcs, and Fc fragments. Immunoglobulins may be Fc polypeptides.

By "Fc fusion" as used herein is meant a protein wherein one or more polypeptides is operably linked to Fc. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both hereby entirely incorporated by reference). An Fc fusion combines the Fc region of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, e.g., an extracellular receptor that is implicated in disease.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, incorporated entirely by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "Fc ligand" or "Fc receptor" as used herein is meant a molecule, e.g., a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, *Immunological Reviews* 190:123-136). Fc ligands may include undiscovered molecules that bind Fc.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "immunoglobulin" herein is meant a protein comprising one or more polypeptides substantially encoded by immunoglobulin genes. Immunoglobulins include but are not limited to antibodies (including bispecific antibodies) and Fc fusions. Immunoglobulins may have a number of structural forms, including but not limited to full length antibodies, antibody fragments, and individual immunoglobulin domains.

By "immunoglobulin (Ig) domain" as used herein is meant a region of an immunoglobulin that exists as a distinct structural entity as ascertained by one skilled in the art of protein structure. Ig domains typically have a characteristic β-sandwich folding topology. The known Ig domains in the IgG isotype of antibodies are VH Cγ1, Cγ2, Cγ3, VL, and CL.

By "IgG" or "IgG immunoglobulin" as used herein is meant a polypeptide belonging to the class of antibodies that are substantially encoded by a recognized immunoglobulin gamma gene. In humans this class comprises the subclasses or isotypes IgG1, IgG2, IgG3, and IgG4.

By "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE.

By "modification" herein is meant an alteration in the physical, chemical, or sequence properties of a protein, polypeptide, antibody, or immunoglobulin. Modifications described herein include amino acid modifications and glycoform modifications.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution S267E refers to a variant polypeptide, in this case a constant heavy chain variant, in which the serine at position 267 is replaced with glutamic acid. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "glycoform modification" or "modified glycoform" or "engineered glycoform" as used herein is meant a carbohydrate composition that is covalently attached to a protein, for example an antibody, wherein said carbohydrate composition differs chemically from that of a parent protein. Modified glycoform typically refers to the different carbohydrate or oligosaccharide; thus for example an Fc variant may comprise a modified glycoform. Alternatively, modified glycoform may refer to the Fc variant that comprises the different carbohydrate or oligosaccharide.

By "parent polypeptide", "parent protein", "parent immunogloblin", "precursor polypeptide", "precursor protein", or "precursor immunoglobulin" as used herein is meant an unmodified polypeptide, protein, or immunoglobulin that is subsequently modified to generate a variant, e.g., any polypeptide, protein or immunoglobulin which serves as a template and/or basis for at least one amino acid modification described herein. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant Fc polypeptide, and by "parent antibody" as used herein is meant an antibody that is modified to generate a variant antibody (e.g., a parent antibody may include, but is not limited to, a protein comprising the constant region of a naturally occurring Ig).

By "position" as used herein is meant a location in the sequence of a protein. Positions may be numbered sequentially, or according to an established format, for example the EU index as in Kabat. For example, position 297 is a position in the human antibody IgG1.

By "polypeptide" or "protein" as used herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound by the variable region of a given antibody, or the fusion partner of an Fc fusion. A target antigen may be a protein, carbohydrate, lipid, or other chemical compound. An antibody or Fc fusion is said to be "specific" for a given target antigen based on having affinity for the target antigen.

By "target cell" as used herein is meant a cell that expresses a target antigen.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "variant polypeptide", "polypeptide variant", or "variant" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. In some embodiments, variant polypeptides disclosed herein (e.g., variant immunoglobulins) may have at least one amino acid modification compared to the parent polypeptide, e.g. from about one to about ten amino acid modifications, from about one to about five amino acid modifications, etc. compared to the parent. The variant polypeptide sequence herein may possess at least about 80% homology with a parent polypeptide sequence, e.g., at least about 90% homology, 95% homology, etc. Accordingly, by "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it. By "Fc polypeptide variant" or "variant Fc polypeptide" as used herein is meant an Fc polypeptide that differs from a parent Fc polypeptide by virtue of at least one amino acid modification. By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

By "wild type" or "WT" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

Immunoglobulins

As described herein, an immunoglobulin may be an antibody, an Fc fusion, an isolated Fc, an Fc fragment, or an Fc polypeptide. In one embodiment, an immunoglobulin is an antibody.

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Each of the light and heavy chains are made up of two distinct regions, referred to as the variable and constant regions. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively. The constant regions show less sequence diversity, and are responsible for binding a number of natural proteins to elicit important biochemical events. The distinguishing features between these antibody classes are their constant regions, although subtler differences may exist in the variable region.

The variable region of an antibody contains the antigen binding determinants of the molecule, and thus determines the specificity of an antibody for its target antigen. The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, hereby entirely incorporated by reference, and the conserved features of antibodies are disclosed, for example, in Maynard et al., 2000, Annu Rev Biomed Eng 2:339-376, hereby entirely incorporated by reference.

The carboxy-terminal portion of each chain defines a constant region primarily responsible for effector function. In the IgG subclass of immunoglobulins, there are several immunoglobulin domains in the heavy chain. By "immunoglobulin (Ig) domain" herein is meant a region of an immunoglobulin having a distinct tertiary structure. Of interest in embodiments described herein are the heavy chain domains, including, the constant heavy (CH) domains and the hinge region. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another important region of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230 to 236.

Of interest in embodiments described herein are the Fc regions. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the lower hinge region between Cgamma1 (Cγ1) and Cgamma2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

The Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290, both hereby entirely incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, hereby entirely incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γγT cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, both hereby entirely incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65, hereby entirely incorporated by reference). The FcγRs bind the IgG Fc region with different affinities. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge. This interaction is well characterized structurally (Sondermann et al., 2001, J Mol Biol 309:737-749, hereby entirely incorporated by reference), and several structures of the human Fc bound to the extracellular domain of human FcγRIIIb have been solved (pdb accession code 1E4K) (Sondermann et al., 2000, Nature 406:267-273, hereby entirely incorporated by reference) (pdb accession codes 1IIS and 1IIX) (Radaev et al., 2001, J Biol Chem 276:16469-16477, hereby entirely incorporated by reference).

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, both hereby entirely incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins (Umana et al., 1999, Nat Biotechnol 17:176-180; Davies et al., 2001, Biotechnol Bioeng 74:288-294; Mimura et al., 2001, J Biol Chem 276: 45539-45547.; Radaev et al., 2001, J Biol Chem 276:16478-16483; Shields et al., 2001, J Biol Chem 276:6591-6604; Shields et al., 2002, J Biol Chem 277:26733-26740; Simmons et al., 2002, J Immunol Methods 263:133-147, all hereby entirely incorporated by reference).

Immunoglobulins of embodiments described herein may also be an antibody-like protein referred to as an Fc fusion (Chamow et al., 1996, *Trends Biotechnol* 14:52-60; Ashkenazi et al., 1997, *Curr Opin Immunol* 9:195-200, both incorporated entirely by reference). "Fc fusion" is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion is a protein wherein one or more polypeptides, herein referred to as a "fusion partner", is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present disclosure extends also to Fc fusions.

Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any agent that directs the Fc fusion to a target antigen. Such target antigen may be any molecule, e.g., an extracellular receptor, that is implicated in disease. Fc fusions of embodiments described herein may target virtually antigen that is expressed on $CD32b^+$ cells.

Fusion partners may be linked to any region of an Fc region, including at the N- or C-termini, or at some residue in-between the termini. In one embodiment, a fusion partner is linked at the N- or C-terminus of the Fc region. A variety of linkers may find use in some embodiments described herein to covalently link Fc regions to a fusion partner. By "linker", "linker sequence", "spacer", "tethering sequence" or grammatical equivalents thereof, herein is meant a molecule or group of molecules (such as a monomer or polymer) that connects two molecules and often serves to place the two molecules in a configuration. Linkers are known in the art; for example, homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length. In one embodiment, h linkers of 1 to 20 amino acids in length may be used. Useful linkers include glycine-serine polymers (including, for example, (GS)n, (GSGGS)n (set forth as SEQ ID NO:1), (GGGGS)n (set forth as SEQ ID NO:2), and (GGGS)n (set forth as SEQ ID NO:3), where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link an Fc regions to a fusion partner.

Also contemplated as fusion partners are Fc polypeptides. Thus an immunoglobulin as described herein may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab's and Fc's may be linked by thioether bonds originating at cysteine residues in the hinges, generating molecules such as $FabFc_2$. Fc regions may be linked using disulfide engineering and/or chemical cross-linking. In one embodiment, Fc regions may be linked genetically. In one embodiment, Fc regions in an immunoglobulin are linked genetically to generated tandemly linked Fc regions as described in U.S. Ser. No. 11/022, 289, filed Dec. 21, 2004, entitled "Fc polypeptides with novel Fc ligand binding sites," incorporated entirely by reference. Tandemly linked Fc polypeptides may comprise two or more Fc regions, e.g., one to three Fc regions, two Fc regions. It may be advantageous to explore a number of engineering constructs in order to obtain homo- or hetero-tandemly linked Fc regions with the most favorable structural and functional properties. Tandemly linked Fc regions may be homo-tandemly linked Fc regions, that is an Fc region of one isotype is fused genetically to another Fc region of the same isotype. It is anticipated that because there are multiple FcγR, C1q, and/or FcRn binding sites on tandemly linked Fc polypeptides, effector functions and/or pharmacokinetics may be enhanced. In an alternate embodiment, Fc regions from different isotypes may be tandemly linked, referred to as hetero-tandemly linked Fc regions. For example, because of the capacity to target FcγR and FcαRI receptors, an immunoglobulin that binds both FcγRs and FcαRI may provide a significant clinical improvement.

The immunoglobulins of embodiments disclosed herein may be substantially encoded by immunoglobulin genes belonging to any of the antibody classes. In certain embodiments, the immunoglobulins disclosed herein find use in antibodies or Fc fusions that comprise sequences belonging to the IgG class of antibodies, including IgG1, IgG2, IgG3, or IgG4. FIG. 1 provides an alignment of these human IgG sequences. In alternate embodiments, immunoglobulins disclosed herein find use in antibodies or Fc fusions that comprise sequences belonging to the IgA (including subclasses IgA1 and IgA2), IgD, IgE, IgG, or IgM classes of antibodies. The immunoglobulins disclosed herein may comprise more than one protein chain, e.g., may be an antibody or Fc fusion that is a monomer or an oligomer, including a homo- or hetero-oligomer.

Immunoglobulins disclosed herein may be substantially encoded by genes from any organism, e.g., mammals (including, but not limited to humans, rodents (including but not limited to mice and rats), lagomorpha (including but not limited to rabbits and hares), camelidae (including but not limited to camels, llamas, and dromedaries), and non-human primates, including but not limited to Prosimians, Platyrrhini (New World monkeys), Cercopithecoidea (Old World monkeys), and Hominoidea including the Gibbons and Lesser and Great Apes. In a certain embodiments, the immunoglobulins disclosed herein may be substantially human.

As is well known in the art, immunoglobulin polymorphisms exist in the human population. Gm polymorphism is determined by the IGHG1, IGHG2 and IGHG3 genes which have alleles encoding allotypic antigenic determinants referred to as G1 m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem. Immunol. 65:88-110; Gorman & Clark, 1990, Semin Immunol 2(6):457-66, both hereby entirely incorporated by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. FIG. 2 shows common haplotypes of the gamma chain of human IgG1 (FIG. 2A) and IgG2 (FIG. 2A) showing the positions and the relevant amino acid substitutions. The immunoglobulins disclosed herein may be substantially encoded by any allotype, isoallotype, or haplotype of any immunoglobulin gene.

The immunoglobulins disclosed herein may compose an Fc polypeptide, including but not limited to antibodies, isolated Fcs, Fc fragments, and Fc fusions. In one embodiment, an immunoglobulin disclosed herein is a full length antibody, constituting the natural biological form of an antibody, including variable and constant regions. For the IgG isotype full length antibody is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In another embodiment, immunoglobulins disclosed herein are isolated Fc regions or Fc fragments.

Immunoglobulins disclosed herein may be a variety of structures, including, but not limited antibody fragments, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

Nonhuman, Chimeric, Humanized, and Fully Human Antibodies

The variable region of an antibody, as is well known in the art, can compose sequences from a variety of species. In some embodiments, the antibody variable region can be from a nonhuman source, including but not limited to mice, rats, rabbits, camels, llamas, and monkeys. In some embodiments, the scaffold components can be a mixture from different species. As such, an antibody disclosed herein may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,693,762, incorporated entirely by reference. The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084. Structure-based methods may be employed for humanization and affinity maturation, for example as described in U.S. Ser. No. 10/153,159 and related applications, all incorporated entirely by reference. In certain variations, the immunogenicity of the antibody is reduced using a method described in U.S. Ser. No. 11/004,590, entitled "Methods of Generating Variant Proteins with Increased Host String Content and Compositions Thereof", filed on Dec. 3, 2004, incorporated entirely by reference.

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108).

Target Antigens

Virtually any antigen may be targeted by the immunoglobulins disclosed herein, including but not limited to proteins, subunits, domains, motifs, and/or epitopes belonging to the following list of targets: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CAl25, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCl, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-1 (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HLA-DP, HLA-DQ, CD317/HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-1, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3,-4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2TNFRH2), TNFRST23 (DcTRAIL RITNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1 B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNTSA, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors, etc.

In one embodiment, antigens are those that are expressed on CD32b+ cells, e.g., B cell proteins, e.g., one or more proteins of the B cell receptor complex. Target antigens include, but are not limited to, CD19, CD20, CD21 (CR2), CD22, CD23/FcεRII, FcεRI, (α, β, and γ subunits), CD24/BBA-1/HSA, CD27, CD35 (CR1), CD38, CD40, CD45RA, CD52/CAMPATH-1/HE5, CD72, CD79a (Igα), CD79b (Igβ), IgM (μ), CD80, CD81, CD86, Leu13, HLA-DR, -DP, -DQ, CD138, CD317/HM1.24, CD11a, CD11b, CD11c, CD14, CD68, CD163, CD172a, CD200R, and CD206. In one embodiment, the immunoglobulins disclosed herein are also specific for a target antigen selected from the group consisting of: IgM (μ), CD19, CD20, CD21, CD22, CD23, CD24, CD35, CD40, CD45RA, CD72, CD79a, CD79b, CD80, CD81, CD86, and HLA-DR. In one embodiment, immunoglobulins disclosed herein are also specific for a target antigen selected from the group consisting of: IgM (μ), CD79a, CD79b, CD19, CD21, CD22, CD72, CD81, and Leu13. In one embodiment, immunoglobulins disclosed herein are also specific for a target antigen selected from the group consisting of: μ, CD19, CD79a, Cd79b, CD81, and HLA-DR. In another embodiment, immunoglobulins disclosed herein are also specific for a target antigen selected from the group consisting of: CD22, CD40, and CD72.

In another embodiment, target antigens may include those that are bound, or may be bound, to the surface of B cells. For example, immunoglobulins disclosed herein may also target autoimmune antigens (i.e., autoantigens) or allergens. In one embodiment, autoimmune antigens that may be targeted by the immunoglobulins disclosed herein include but are not limited to double-stranded DNA, platelet antigens, myelin protein antigen, Sm antigens in snRNPs, islet cell antigen, Rheumatoid factor, and anticitrullinated protein. citrullinated proteins and peptides such as CCP-1, CCP-2 (cyclical citrullinated peptides), fibrinogen, fibrin, vimentin, fillaggrin, collagen I and II peptides, alpha-enolase, translation initiation factor 4G1, perinuclear factor, keratin, Sa (cytoskeletal protein vimentin), components of articular cartilage such as collagen II, IX, and XI, circulating serum proteins such as RFs (IgG, IgM), fibrinogen, plasminogen, ferritin, nuclear components such as RA33/hnRNP A2, Sm, eukaryotic trasnlation elogation factor 1 alpha 1, stress proteins such as HSP-65, -70, -90, BiP, inflammatory/immune factors such as B7-H1, IL-1 alpha, and IL-8, enzymes such as calpastatin, alpha-enolase, aldolase-A, dipeptidyl peptidase, osteopontin, glucose-6-phosphate isomerase, receptors such as lipocortin 1, neutrophil nuclear proteins such as lactoferrin and 25-35 kD nuclear protein, granular proteins such as bactericidal permeability increasing protein (BPI), elastase, cathepsin G, myeloperoxidase, proteinase 3, platelet antigens, myelin protein antigen, islet cell antigen, rheumatoid factor, histones, ribosomal P proteins, cardiolipin, vimentin, nucleic acids such as dsDNA, ssDNA, and RNA, ribonuclear particles and proteins such as Sm antigens (including but not limited to SmD's and SmB'/B), U1 RNP, A2/B1 hnRNP, Ro (SSA), and La (SSB) antigens.

Fc Variants and Fc Receptor Binding Properties

Immunoglobulins disclosed herein may comprise an Fc variant. An Fc variant comprises one or more amino acid modifications relative to a parent Fc polypeptide, wherein the amino acid modification(s) provide one or more optimized properties. An Fc variant disclosed herein differs in amino acid sequence from its parent by virtue of at least one amino acid modification. Thus Fc variants disclosed herein have at least one amino acid modification compared to the parent. Alternatively, the Fc variants disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein include amino acid modifications, including insertions, deletions, and substitutions. Modifications disclosed herein also include glycoform modifications. Modifications may be made genetically using molecular biology, or may be made enzymatically or chemically.

Fc variants disclosed herein are defined according to the amino acid modifications that compose them. Thus, for example, S267E is an Fc variant with the substitution S267E relative to the parent Fc polypeptide. Likewise, S267E/L328F defines an Fc variant with the substitutions S267E and L328F relative to the parent Fc polypeptide. The identity of the WT amino acid may be unspecified, in which case the aforementioned variant is referred to as 267E/328F. It is noted that the order in which substitutions are provided is arbitrary, that is to say that, for example, 267E/328F is the same Fc variant as 328F/267E, and so on. Unless otherwise noted, positions discussed herein are numbered according to the EU index or EU numbering scheme (Kabat et al., 1991, Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgGD, IgGM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on 0) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

The Fc variants disclosed herein may be optimized for a variety of Fc receptor binding properties. An Fc variant that is engineered or predicted to display one or more optimized properties is herein referred to as an "optimized Fc variant". Properties that may be optimized include but are not limited to enhanced or reduced affinity for an FcγR. In one embodiment, the Fc variants disclosed herein are optimized to possess enhanced affinity for an inhibitory receptor FcγRIIb. In other embodiments, immunoglobulins disclosed herein provide enhanced affinity for FcγRIIb, yet reduced affinity for one or more activating FcγRs, including for example FcγRI, FcγRIIa, FcγRIIIa, and/or FcγRIIIb. The FcγR receptors may be expressed on cells from any organism, including but not limited to human, cynomolgus monkeys, and mice. The Fc variants disclosed herein may be optimized to possess enhanced affinity for human FcγRIIb.

By "greater affinity" or "improved affinity" or "enhanced affinity" or "better affinity" than a parent Fc polypeptide, as used herein is meant that an Fc variant binds to an Fc receptor with a significantly higher equilibrium constant of association ($K_A$ or Ka) or lower equilibrium constant of dissociation ($K_D$ or Kd) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore, by one skilled in the art. Accordingly, by "reduced affinity" as compared to a parent Fc polypeptide as used herein is meant that an Fc variant binds an Fc receptor with significantly lower $K_A$ or higher $K_D$ than the parent Fc polypeptide. Greater or reduced affinity can also be defined relative to an absolute level of affinity. For example, according to the data herein, WT (native) IgG1 binds FcγRIIb with an affinity of about 1.5 µM, or about 1500 nM. Furthermore, some Fc variants described herein bind FcγRIIb with an affinity about 10-fold greater to WT IgG1. As disclosed herein, greater or enhanced affinity means having a $K_D$ lower than about 100 nM, for example between about 10 nM-about 100 nM, between about 1-about 100 nM, or less than about 1 nM.

In one embodiment, the Fc variants provide selectively enhanced affinity to FcγRIIb relative to one or more activating receptors. Selectively enhanced affinity means either that the Fc variant has improved affinity for FcγRIIb relative to the activating receptor(s) as compared to the parent Fc polypeptide but has reduced affinity for the activating receptor(s) as compared to the parent Fc polypeptide, or it means that the Fc variant has improved affinity for both FcγRIIb and activating receptor(s) as compared to the parent Fc polypeptide, however the improvement in affinity is greater for FcγRIIb than it is for the activating receptor(s). In alternate embodiments, the Fc variants reduce or ablate binding to one or more activating FcγRs, reduce or ablate binding to one or more complement proteins, reduce or ablate one or more FcγR-mediated effector functions, and/or reduce or ablate one or more complement-mediated effector functions.

The presence of different polymorphic forms of FcγRs provides yet another parameter that impacts the therapeutic utility of the Fc variants disclosed herein. Whereas the specificity and selectivity of a given Fc variant for the different classes of FcγRs significantly affects the capacity of an Fc variant to target a given antigen for treatment of a given disease, the specificity or selectivity of an Fc variant for different polymorphic forms of these receptors may in part determine which research or pre-clinical experiments may be appropriate for testing, and ultimately which patient populations may or may not respond to treatment. Thus the specificity or selectivity of Fc variants disclosed herein to Fc receptor polymorphisms, including but not limited to FcγRIIa, FcγRIIIa, and the like, may be used to guide the selection of valid research and pre-clinical experiments, clinical trial design, patient selection, dosing dependence, and/or other aspects concerning clinical trials.

Fc variants disclosed herein may comprise modifications that modulate interaction with Fc receptors other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

An important parameter that determines the most beneficial selectivity of a given Fc variant to treat a given disease is the context of the Fc variant. Thus the Fc receptor selectivity or specificity of a given Fc variant will provide different properties depending on whether it composes an antibody, Fc fusion, or Fc variants with a coupled fusion partner. In one embodiment, an Fc receptor specificity of the Fc variant disclosed herein will determine its therapeutic utility. The utility of a given Fc variant for therapeutic purposes will depend on the epitope or form of the target antigen and the disease or indication being treated. For some targets and indications, greater FcγRIIb affinity and reduced activating FcγR-mediated effector functions may be beneficial. For other target antigens and therapeutic applications, it may be beneficial to increase affinity for FcγRIIb, or increase affinity for both FcγRIIb and activating receptors.

Inhibitory Properties and Methods of Inhibiting $CD32b^+$ Cells

Target antigens of immunoglobulins disclosed herein may be expressed on a variety of cell types. In some embodiments, immunoglobulins disclosed herein are specific for antigens expressed on CD32b+ cells. Cell types that may be targeted by the immunoglobulins disclosed herein include, but are not limited to, B cells, plasma cells, dendritic cells, macrophages, neutrophils, mast cells, basophils, and eosinophils. In alternative embodiments, the immunoglobulins disclosed herein may inhibit CD32b+ cells by targeting an antigen not expressed on CD32b+ cells. In some embodiments, target antigens include those that are not expressed by CD32b+ cells, but may be bound to CD32b+ cells, e.g., via the BCR. For example, in certain embodiments, the immunoglobulins may target an autoimmune antigen or allergen. Autoimmune antigens that may be targeted by the immunoglobulins disclosed herein include but are not limited to citrullinated proteins and peptides such as CCP-1, CCP-2 (cyclical citrullinated peptides), fibrinogen, fibrin, vimentin, fillaggrin, collagen I and II peptides, alpha-enolase, translation initiation factor 4G1, perinuclear factor, keratin, Sa (cytoskeletal protein vimentin), components of articular cartilage such as collagen II, IX, and XI, circulating serum proteins such as RFs (IgG, IgM), fibrinogen, plasminogen, ferritin, nuclear components such as RA33/hnRNP A2, Sm, eukaryotic trasnlation elogation factor 1 alpha 1, stress proteins such as HSP-65, -70, -90, BiP, inflammatory/immune factors such as B7-H1, IL-1 alpha, and IL-8, enzymes such as calpastatin, alpha-enolase, aldolase-A, dipeptidyl peptidase, osteopontin, glucose-6-phosphate isomerase, receptors such as lipocortin 1, neutrophil nuclear proteins such as lactoferrin and 25-35 kD nuclear protein, granular proteins such as bactericidal permeability increasing protein (BPI), elastase, cathepsin G, myeloperoxidase, proteinase 3, platelet antigens, myelin protein antigen, islet cell antigen, rheumatoid factor, histones, ribosomal P proteins, cardiolipin, vimentin, nucleic acids such as dsDNA, ssDNA, and RNA, ribonuclear particles and proteins such as Sm antigens (including but not limited to SmD's and SmB'/B), U1RNP, A2/B1 hnRNP, Ro (SSA), and La (SSB) antigens.

Disclosed herein are methods of inhibiting CD32b+ cells. Without being limited thereto, FIG. 3 is a schematic representation of a proposed mechanism by which immunoglobulins disclosed herein inhibit CD32b+ cells (See also Example 3; see also FIG. 3). Accordingly, disclosed herein are methods of inhbiting CD32b+ cells comprising contacting a CD32b+ cell with an immunoglobulin comprising an Fc region with enhanced affinity to FcγRIIb. In one embodiment, the immunoglobulin binds at least two B cell proteins, .e.g., at least to proteins bound to the surface B cells. In one embodiment, the first of said B cell proteins is FcγRIIb. In a another embodiment, the second of said B cell proteins is part of the B cell receptor (BCR) complex, which may include an antigen bound to BCR. In another embodiment, the second of said B cell proteins is not involved directly in antigen recognition. In another embodiment, said the second of said B cell proteins is expressed on the surface of the B cell, but is not part of the B cell receptor. Nonlimiting examples of the second of said B cell proteins include BCR proteins (e.g., IgM (μ), CD79a, CD79b, CD19, CD21, CD22, CD72, CD81, Leu13, etc.), antigens bound to the BCR (e.g., autoantigens, allergens, etc.), or other proteins bound to the surface of B cells (e.g., CD20, CD23, CD24, CD35, CD40, CD45RA, CD80, CD86, HLA-DR, etc.). In some embodiments, the immunoglobulins inhibit release of calcium from the B cells upon their stimulation through the B cell receptor. In another embodiment, an immunoglobulin disclosed herein binds at least two B cell proteins on the surface of the same B cell (see, .e.g., FIG. 3).

Modifications for Optimizing Inhibitory Function

Disclosed herein is directed to immunoglobulins comprising modifications, wherein said modifications alter affinity to the FcγRIIb receptor, and/or alter the ability of the immunoglobulin to mediate one or more FcγRIIb-mediated effector functions. Modifications of the invention include amino acid modifications and glycoform modifications.

Amino Acid Modifications

As described herein (see, e.g., Example 9), simultaneous high affinity coengagement of cognate BCR and FcγRIIb may be used to inhibit FcγRIIb+ cells. Such coengagment may occur via the use of an immunoglobulin described herein, e.g., an immunoglobulin used to coengage both FcγRIIb via its Fc region, and a target antigen on the surface of the FcγRIIb+ cell (e.g., one or more cognate BCR proteins and/or an antigen bound to cognate BCR) via its Fv region. Amino acid modifications at heavy chain constant region positions: 234, 235, 236, 237, 239, 265, 266, 267, 268, 298, 325, 326, 327, 328, 329, 330, 331 and 332 allow modification of immunoglobulin FcγRIIb binding properties, effector function, and potentially clinical properties of antibodies In one embodiment, immunoglobulins that bind FcγRIIb+ cells and coengage a target antigen on the cell's surface and an FcγRIIb on cell's surface disclosed herein may be variant immunoglobulins relative to a parent immunoglobulin. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 239, 265, 266, 267, 268, 298, 325, 326, 327, 328, 329, 330, 331, and 332, wherein numbering is according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 239, 266, 267, 268, 325, 326, 327, 328, and 332, according to the EU index. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 235, 236, 239, 266, 267, 268, and 328, according to the EU index.

In one embodiment, said modification(s) is at least one substitution (e.g., one or more substitution(s), two or more substitution(s), etc.) selected from the group consisting of 234F, 234G, 234I, 234K, 234N, 234P, 234Q, 234S, 234V, 234W, 234Y, 234D, 234E, 235A, 235E, 235H, 235I, 235N, 235P, 235Q, 235R, 235S, 235W, 235Y, 235D, 235F, 235T, 236D, 236F, 236H, 236I, 236K, 236L, 236M, 236P, 236Q, 236R, 236S, 236T, 236V, 236W, 236Y, 236A, 236E, 236N, 237A, 237E, 237H, 237K, 237L, 237P, 237Q, 237S, 237V, 237Y, 237D, 237N, 239D, 239E, 239N, 239Q, 265E, 266D, 266I, 266M, 267A, 267D, 267E, 267G, 268D, 268E, 268N, 268Q, 298D, 298E, 298L, 298M, 298Q, 325L, 326A, 326E, 326W, 326D, 327D, 327G, 327L, 327N, 327Q, 327E, 328E, 328F, 328Y, 328H, 328I, 328Q, 328W, 329E, 330D, 330H, 330K, 330S, 331S, and 332E, wherein numbering is according to an EU index. In one embodiment, said modification(s) is at least one substitution (e.g., one or more substitution(s), two or more substitution(s), etc.) selected from the group consisting of 234N, 234F, 234D, 234E, 234W, 235Q, 235R, 235W, 235Y, 235D, 235F, 235T, 236D, 236H, 236I, 236L, 236S, 236Y, 236E, 236N, 237H, 237L, 237D, 237N, 239D, 239N, 239E, 266I, 266M, 267A, 267D, 267E, 267G, 268D, 268E, 268N, 268Q, 298E, 298L, 298M, 298Q, 325L, 326A, 326E, 326W, 326D, 327D, 327L, 327E, 328E, 328F, 328Y, 328H, 328I, 328Q, 328W, 330D, 330H, 330K, and 332E, wherein numbering is according to an EU index. In one embodiment, said modification(s) is at least one substitution (e.g., one or more substitution(s), two or more substitution(s), etc.) selected from the group consisting of 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E, wherein numbering is according to an EU index. In one embodiment, said modification(s) is at least one substitution (e.g., one or more substitution(s), two or more substitution(s), etc.) selected from the group consisting of 235Y, 236D, 239D, 266M, 267E, 268D, 268E, 328F, 328W, and 328Y, wherein numbering is according to an EU index.

In one embodiment, said modification(s) is at least two modifications (e.g., a combination of modifications) at positions selected from the group consisting of 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332, wherein numbering is according to an EU index. In one embodiment, said modification(s) is at least two modifications (e.g., a combination of modifications) at positions selected from the group consisting of 235/267, 236/267, 239/268, 239/267, 267/268, and 267/328, wherein numbering is according to an EU index. In one embodiment, said modification(s) is at least two substitutions (e.g., a combination of substitutions) selected from the group consisting of 234D/267E, 234E/267E, 234F/267E, 234E/328F, 234W/239D, 234W/239E, 234W/267E, 234W/328Y, 235D/267E, 235D/328F, 235F/239D, 235F/267E, 235F/328Y, 235Y/236D, 235Y/239D, 235Y/267D, 235Y/267E, 235Y/268E, 235Y/328F, 236D/239D, 236D/267E, 236D/268E, 236D/

328F, 236N/267E, 237D/267E, 237N/267E, 239D/267D, 239D/267E, 239D/268D, 239D/268E, 239D/327D, 239D/328F, 239D/328W, 239D/328Y, 239D/332E, 239E/267E, 266M/267E, 267D/268E, 267E/268D, 267E/268E, 267E/325L, 267E/327D, 267E/327E, 267E/328F, 267E/328I, 267E/328Y, 267E/332E, 268D/327D, 268D/328F, 268D/328W, 268D/328Y, 268D/332E, 268E/328F, 268E/328Y, 327D/328Y, 328F/332E, 328W/332E, and 328Y/332E, wherein numbering is according to an EU index.

In one embodiment, said modification(s) result in at least one of the following substitutions, or combinations of substitutions: 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327D, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/239D/267E, 236D/239D/267E, 235Y/267E/268E, 236D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E, wherein numbering is according to an EU index. In one embodiment, said modification(s) result in at least one of the following substitutions, or combinations of substitutions: 234N, 235Q, 235R, 235W, 235Y, 236D, 236H, 236I, 236L, 236S, 236Y, 237H, 237L, 239D, 239N, 266I, 266M, 267A, 267D, 267E, 267G, 268D, 268E, 268N, 268Q, 298E, 298L, 298M, 298Q, 326A, 326E, 326W, 327D, 327L, 328E, 328F, 330D, 330H, 330K, 234F/236N, 234F/236D, 235D/239D, 234D/267E, 234E/267E, 234F/267E, 235D/267E, 235F/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327D, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/239D/267E, 236D/239D/267E, 235Y/267E/268E, 236D/267E/268E, 239D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 239D/267E/332E, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E In one embodiment, said modification(s) result in at least one of the following substitutions, or combinations of substitutions: 235Y/267E, 236D/267E, 239D/268D, 239D/267E, 267E/268D, 267E/268E, and 267E/328F, wherein numbering is according to an EU index.

In some embodiments, antibodies may comprise isotypic modifications, that is, modifications in a parent IgG to the amino acid type in an alternate IgG. For example as illustrated in FIG. 1, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions selected from the group consisting of: 274Q, 276K, 300F, 339T, 356E, 358M, 384S, 392N, 397M, 422I, 435R, and 436F. In other embodiments of the invention, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more modifications selected from the group consisting of 233E, 234L, 235L, –236G (referring to an insertion of a glycine at position 236), and 327A.

Means for Optimizing Effector Function

Described herein are immunoglobulins comprising means for alter affinity to the FcγRIIb receptor, and/or alter the ability of the immunoglobulin to mediate one or more FcγRIIb-mediated effector functions. Means of the invention include amino acid modifications (e.g., positional means for optimizing effector function, substitutional means for optimizing effector function, etc.) and glycoform modifications (e.g., means for glycoform modifications).

Amino Acid Modifications

As described herein, positional means for optimizing effector function include but is not limited to, modification of an amino acid at one or more heavy chain constant region positions (e.g., at positions: 234, 235, 236, 237, 239, 265, 266, 267, 268, 298, 325, 326, 327, 328, 329, 330, 331, and 332)

which allow modification of immunoglobulin FcγRIIb binding properties, effector function, and potentially clinical properties of antibodies.

In particular, substitutional means for optimizing FcγRIIb effector functions, e.g., by altering affinity to FcγRIIb, include, but is not limited to, a substitution of an amino acid at one or more heavy chain constant region positions, e.g., one or more of the amino acid substitutions in the following heavy chain constant region positions: 234, 235, 236, 237, 239, 265, 266, 267, 268, 298, 325, 326, 327, 328, 329, 330, 331, and 332, wherein numbering is according to the EU index. In one embodiment, substitutional means include at least one (e.g., two or more) substitution(s) compared to a parent Fc region, wherein said modification(s) are at positions selected from the group consisting of 234, 235, 236, 237, 239, 266, 267, 268, 325, 326, 327, 328, and 332, according to the EU index. In one embodiment, substitutional means include one or more (e.g., two or more) substitions(s) at positions selected from the group consisting of 235, 236, 239, 266, 267, 268, and 328, according to the EU index.

In one embodiment, said substitutional means is at least one substitution (e.g., one or more substitution(s), two or more substitution(s), etc.) selected from the group consisting of 234F, 234G, 234I, 234K, 234N, 234P, 234Q, 234S, 234V, 234W, 234Y, 234D, 234E, 235A, 235E, 235H, 235I, 235N, 235P, 235Q, 235R, 235S, 235W, 235Y, 235D, 235F, 235T, 236D, 236F, 236H, 236I, 236K, 236L, 236M, 236P, 236Q, 236R, 236S, 236T, 236V, 236W, 236Y, 236A, 236E, 236N, 237A, 237E, 237H, 237K, 237L, 237P, 237Q, 237S, 237V, 237Y, 237D, 237N, 239D, 239E, 239N, 239Q, 265E, 266D, 266I, 266M, 267A, 267D, 267E, 267G, 268D, 268E, 268N, 268Q, 298D, 298E, 298L, 298M, 298Q, 325L, 326A, 326E, 326W, 326D, 327D, 327G, 327L, 327N, 327Q, 327E, 328E, 328F, 328Y, 328H, 328I, 328Q, 328W, 329E, 330D, 330H, 330K, 330S, 331S, and 332E, wherein numbering is according to an EU index. In one embodiment, said substitutional means is at least one substitution (e.g., one or more substitution(s), two or more substitution(s), etc.) selected from the group consisting of 234N, 234F, 234D, 234E, 234W, 235Q, 235R, 235W, 235Y, 235D, 235F, 235T, 236D, 236H, 236I, 236L, 236S, 236Y, 236E, 236N, 237H, 237L, 237D, 237N, 239D, 239N, 239E, 266I, 266M, 267A, 267D, 267E, 267G, 268D, 268E, 268N, 268Q, 298E, 298L, 298M, 298Q, 325L, 326A, 326E, 326W, 326D, 327D, 327L, 327E, 328E, 328F, 328Y, 328H, 328I, 328Q, 328W, 330D, 330H, 330K, and 332E, wherein numbering is according to an EU index. In one embodiment, said substitutional means is at least one substitution (e.g., one or more substitution(s), two or more substitution(s), etc.) selected from the group consisting of 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E, wherein numbering is according to an EU index. In one embodiment, said substitutional means is at least one substitution (e.g., one or more substitution(s), two or more substitution(s), etc.) selected from the group consisting of 235Y, 236D, 239D, 266M, 267E, 268D, 268E, 328F, 328W, and 328Y, wherein numbering is according to an EU index.

In one embodiment, said substitutional means is at least two substitutions (e.g., a combination of modifications) at positions selected from the group consisting of 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332, wherein numbering is according to an EU index. In one embodiment, said substitutional means is at least two substitutions (e.g., a combination of modifications) at positions selected from the group consisting of 235/267, 236/267, 239/268, 239/267, 267/268, and 267/328, wherein numbering is according to an EU index. In one embodiment, said substitutional means is at least two substitutions (e.g., a combination of substitutions) selected from the group consisting of 234D/267E, 234E/267E, 234F/267E, 234E/328F, 234W/239D, 234W/239E, 234W/267E, 234W/328Y, 235D/267E, 235D/328F, 235F/239D, 235F/267E, 235F/328Y, 235Y/236D, 235Y/239D, 235Y/267D, 235Y/267E, 235Y/268E, 235Y/328F, 236D/239D, 236D/267E, 236D/268E, 236D/328F, 236N/267E, 237D/267E, 237N/267E, 239D/267D, 239D/267E, 239D/268D, 239D/268E, 239D/327D, 239D/328F, 239D/328W, 239D/328Y, 239D/332E, 239E/267E, 266M/267E, 267D/268E, 267E/268D, 267E/268E, 267E/325L, 267E/327D, 267E/327E, 267E/328F, 267E/328I, 267E/328Y, 267E/332E, 268D/327D, 268D/328F, 268D/328W, 268D/328Y, 268D/332E, 268E/328F, 268E/328Y, 327D/328Y, 328F/332E, 328W/332E, and 328Y/332E, wherein numbering is according to an EU index.

In one embodiment, said substitutional means result in at least one of the following substitutions, or combinations of substitutions: 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327D, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/239D/267E, 236D/239D/267E, 235Y/267E/268E, 236D/267E/268E, 239D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 239D/267E/332E, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E, wherein numbering is according to an EU index. In one embodiment, said substitutional means result in at least one of the following substitutions, or combinations of substitutions: 266D, 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 236D/267E, 236E/267E, 236N/267E, 237D/267E, 237N/267E, 266M/267E, 234E/268D, 236D/268D, 267D/268D, 267D/268E, 267E/268D, 267E/268E, 267E/325L, 267D/327D, 267D/327E, 267E/327E, 268D/327D, 239D/328Y, 267E/328F, 267E/328H, 267E/328I, 267E/328Q, 267E/328Y, 268D/328Y, 234D/236N/267E, 235Y/236D/267E, 234W/239E/267E, 235Y/239D/267E, 236D/239D/267E, 235Y/267E/268E, 236D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/

328Y, 268D/327D/328Y, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E, wherein numbering is according to an EU index. In one embodiment, said substitional means result in at least one of the following substitutions, or combinations of substitutions: 234N, 235Q, 235R, 235W, 235Y, 236D, 236H, 236I, 236L, 236S, 236Y, 237H, 237L, 239D, 239N, 266I, 266M, 267A, 267D, 267E, 267G, 268D, 268E, 268N, 268Q, 298E, 298L, 298M, 298Q, 326A, 326E, 326W, 327D, 327L, 328E, 328F, 330D, 330H, 330K, 234F/236N, 234F/236D, 235D/239D, 234D/267E, 234E/267E, 234F/267E, 235D/267E, 235F/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327D, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/239D/267E, 236D/239D/267E, 235Y/267E/268E, 236D/267E/268E, 239D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 239D/267E/332E, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E In one embodiment, said substitional means result in at least one of the following substitutions, or combinations of substitutions: 235Y/267E, 236D/267E, 239D/268D, 239D/267E, 267E/268D, 267E/268E, and 267E/328F, wherein numbering is according to an EU index.

In some embodiments of the invention, immunoglobulin may comprise means for isotypic modifications, that is, modifications in a parent IgG to the amino acid type in an alternate IgG. For example as illustrated in FIG. 2A, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 422I, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, -236G (referring to an insertion of a glycine at position 236), and 327A.

Glycoform Modifications

Many polypeptides, including antibodies, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation (Lifely et al., 1995, Glycobiology 5(8): 813-822).

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate (Jefferis et al., 1998, Immunol. Rev. 163:59-76; Wright et al., 1997, Trends Biotech 15:26-32). For human IgG, the core oligosaccharide normally consists of $GlcNAc_2Man_3GlcNAc$, with differing numbers of outer residues.

The carbohydrate moieties of immunoglobulins disclosed herein will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of immunoglobulins disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991).

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)$_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

Described herein are Fc variants that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the immunoglobulins disclosed herein are modified to control the level of fucosylated and/or bisecting oligosaccharides that are covalently attached to the Fc region.

A variety of methods are well known in the art for generating modified glycoforms (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. Nos. 10/277,370; 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltransferase] and/or [3]-4-N-acetylglucosaminyltransferase III [GnTIII]), or by modifying carbohydrate(s) after the IgG has been expressed. Other methods for modifying glycoforms of the immunoglobulins disclosed herein include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass Fc variants with modified glycoforms irrespective of how they are produced.

In one embodiment, immunoglobulins disclosed herein are glycoengineered to alter the level of sialylation. Higher levels of sialylated Fc glycans in immunoglobulin G molecules can adversely impact functionality (Scallon et al., 2007, Mol. Immunol. 44(7):1524-34), and differences in levels of Fc sialylation can result in modified anti-inflammatory activity (Kaneko et al., 2006, Science 313:670-673). Because antibodies may acquire anti-inflammatory properties upon sialylation of Fc core polysaccharide, it may be advantageous to glycoengineer the immunoglobulins disclosed herein for greater or reduced Fc sialic acid content.

Engineered glycoform typically refers to the different carbohydrate or oligosaccharide; thus for example an immuoglobulin may comprise an engineered glycoform. Alternatively, engineered glycoform may refer to the immunoglobulin that comprises the different carbohydrate or oligosaccharide. In one embodiment, a composition disclosed herein comprises a glycosylated Fc variant having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated Fc variant having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated Fc variant having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

Other Modifications

Immunoglobulins disclosed herein may comprise one or more modifications that provide optimized properties that are not specifically related to FcγR- or complement-mediated effector functions per se. Said modifications may be amino acid modifications, or may be modifications that are made enzymatically or chemically. Such modification(s) likely provide some improvement in the immunoglobulin, for example an enhancement in its stability, solubility, function, or clinical use. Disclosed herein are a variety of improvements that may be made by coupling the immunoglobulins disclosed herein with additional modifications.

In one embodiment, the variable region of an antibody disclosed herein may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen. Immunoglobulins disclosed herein may comprise one or more modifications that provide reduced or enhanced internalization of an immunoglobulin.

In one embodiment, modifications are made to improve biophysical properties of the immunoglobulins disclosed herein, including but not limited to stability, solubility, and oligomeric state. Modifications can include, for example, substitutions that provide more favorable intramolecular interactions in the immunoglobulin such as to provide greater stability, or substitution of exposed nonpolar amino acids with polar amino acids for higher solubility. A number of optimization goals and methods are described in U.S. Ser. No. 10/379,392, incorporated entirely by reference, that may find use for engineering additional modifications to further optimize the immunoglobulins disclosed herein. The immunoglobulins disclosed herein can also be combined with additional modifications that reduce oligomeric state or size, such that tumor penetration is enhanced, or in vivo clearance rates are increased as desired.

Other modifications to the immunoglobulins disclosed herein include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, *J. Immunol.*, 2001, 166: 1320-1326; Stevenson et al., 2002, *Recent Results Cancer Res.* 159: 104-12; U.S. Pat. No. 5,681,566; Caron et al., 1992, *J. Exp. Med.* 176:1191-1195, and Shopes, 1992, *J. Immunol.* 148(9): 2918-22, all incorporated enirely by reference. Additional modifications to the variants disclosed herein include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Biol. 270(1):26-35, and Carter et al., 2001, J. Immunol. Methods 248:7-15, both incorporated entirely by reference. Additional modifications include modifications in the hinge and CH3 domains, in which the modifications reduce the propensity to form dimers.

In further embodiments, the immunoglobulins disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983), incorporated entirely by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The immunoglobulins disclosed herein may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635):964-7, all incorporated enirely by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the immunoglobulin may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the immunoglobulins. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the immunoglobulins disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein. See for example U.S. Ser. Nos. 09/903,378, 10/754,296, 11/249,692, and references cited therein, all expressly incorporated by reference.

In some embodiments, immunoglobulins disclosed herein may be combined with immunoglobulins that alter FcRn binding. Such variants may provide improved pharmacokinetic properties to the immunoglobulins. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102,621, PCT/US2003/033037, PCT/US2004/011213, U.S. Ser. Nos. 10/822,300, 10/687,118, PCT/US2004/034440, U.S. Ser. No. 10/966,673 all entirely incorporated by reference), 256A, 272A, 286A, 305A, 307A, 311A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. Nos. 11/429, 793, 11/429,786, PCT/US2005/029511, U.S. Ser. No. 11/208,422, all entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311 S (DalI Acqua et al. Journal of Immunology, 2002, 169:5171-5180, U.S. Pat. No. 7,083,784, PCT/US97/03321, U.S. Pat. No. 6,821,505, PCT/US01/48432, U.S. Ser. No. 11/397,328, all entirely incorporated by reference), 257C, 257M, 257L, 257N, 257Y, 279E, 279Q, 279Y, insertion of Ser after 281, 283F, 284E, 306Y, 307F, 308F, 308Y 311V, 385H, 385N, (PCT/US2005/041220, U.S. Ser. Nos. 11/274, 065, 11/436,266 all entirely incorporated by reference) 204D, 284E, 285E, 286D, and 290E (PCT/US2004/037929 entirely incorporated by reference).

Covalent modifications of antibodies are included within the scope of immunoglobulins disclosed herein, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies disclosed herein comprises the addition of one or more labels. The term "labeling group" means any detectable label. In some embodiments, the labeling group is coupled to the antibody via spacer arms of various lengths to reduce potential steric hindrance. Various methods for labeling proteins are known in the art and may be used in generating immunoglobulins disclosed herein. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in generating immunoglobulins disclosed herein. Specific labels include optical dyes, including, but not limited to, chromophores, phosphors and fluorophores, with the latter being specific in many instances. Fluorophores can be either "small molecule" fluores, or proteinaceous fluores. By "fluorescent label" is meant any molecule that may be detected via its inherent fluorescent properties.

Conjugates

In one embodiment, the immunoglobulins disclosed herein are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the immunoglobulin. Thus, for example, the conjugation of a toxin to an immunoglobulin targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used loosely to convey the broad concept that any immunoglobulin disclosed herein may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, incorporated enirely by reference.

In one embodiment, the immunoglobulins disclosed herein are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated entirely by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the immunoglobulins disclosed herein are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71, incorporated entirely by reference. Small molecule toxins include but are not limited to calicheamicin, maytansine (U.S. Pat. No. 5,208,020, incorporated entirely by reference), trichothene, and CC1065. In one embodiment, an immunoglobulin disclosed herein may be conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al., 1992, *Cancer Research* 52: 127-131, incorporated entirely by reference) to generate a maytansinoid-antibody conjugate. Another conjugate of interest comprises an immunoglobulin conjugated to one or more calicheamicin molecules. The calicheamicin family of antibiotics are capable of producing double-stranded DNA breaks at subpicomolar concentrations. Structural analogues of calicheamicin that may be used include but are not limited to $\gamma_1^1$, $\alpha_2^1$, $\alpha_3$, N-acetyl-$\gamma_1^1$, PSAG, and $\theta^1_1$, (Hinman et al., 1993, Cancer Research 53:3336-3342; Lode et al., 1998, Cancer Research 58:2925-2928) (U.S. Pat. Nos. 5,714,586; 5,712, 374; 5,264,586; 5,773,001, all incorporated enirely by reference). Dolastatin 10 analogs such as auristatin E (AE) and monomethylauristatin E (MMAE) may find use as conjugates for the immunoglobulins disclosed herein (Doronina et al., 2003, Nat Biotechnol 21(7):778-84; Francisco et al., 2003 Blood 102(4):1458-65, both incorporated entirely by reference). Useful enyzmatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232, incorporated entirely by reference. Embodiments further encompass a conjugate between an immunoglobulin disclosed herein and a compound with nucleolytic activity, for example a ribonuclease or DNA endonuclease such as a deoxyribonuclease (DNase).

In an alternate embodiment, an immunoglobulin disclosed herein may be fused, conjugated, or operably linked to a radioisotope to form a radioconjugate. A variety of radioactive isotopes are available for the production of radioconjugate antibodies. Examples include, but are not limited to, At211, I131, I125, Y90, Re186, Re188, Sm153, Bi212, P32, and radioactive isotopes of Lu. See for example, reference.

In yet another embodiment, an immunoglobulin disclosed herein may be conjugated to a "receptor" (such streptavidin) for utilization in tumor pretargeting wherein the immunoglobulin-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the immunoglobulin is conjugated or operably linked to an enzyme in order to employ Antibody Dependent Enzyme Mediated Prodrug Therapy (ADEPT). ADEPT may be used by conjugating or operably linking the immunoglobulin to a prodrug-activating enzyme that converts a prodrug (e.g. a peptidyl chemotherapeutic agent, see PCT WO 81/01145, incorporated entirely by reference) to an active anti-cancer drug. See, for example, PCT WO 88/07378 and U.S. Pat. No. 4,975,278, both incorporated entirely by reference. The enzyme component of the immunoconjugate useful for ADEPT includes any enzyme capable of acting on a prodrug in such a way so as to covert it into its more active, cytotoxic form. Enzymes that are useful in the method disclosed herein include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs disclosed herein into free active drugs (see, for example, Massey, 1987, *Nature* 328: 457-458, incorporated entirely by reference). immunoglobulin-abzyme conjugates can be prepared for delivery of the abzyme to a tumor cell population. A variety of additional conjugates are contemplated for the immunoglobulins disclosed herein. A variety of chemotherapeutic agents, anti-angiogenic agents, tyrosine kinase inhibitors, and other therapeutic agents are described below, which may find use as immunoglobulin conjugates.

Conjugate partners may be linked to any region of an immunoglobulin disclosed herein, including at the N- or C-termini, or at some residue in-between the termini. A variety of linkers may find use in immunoglobulins disclosed herein to covalently link conjugate partners to an immunoglobulin. By "linker", "linker sequence", "spacer", "tethering sequence" or grammatical equivalents thereof, herein is meant a molecule or group of molecules (such as a monomer or polymer) that connects two molecules and often serves to place the two molecules in one configuration. Linkers are known in the art; for example, homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length, e.g., a linker may be 1 to 20 amino acids in length. Useful linkers include glycine-serine polymers (including, for example, (GS)n, (GSGGS)n (Set forth as SEQ ID NO:1), (GGGGS)n (Set forth as SEQ ID NO:2) and (GGGS)n (Set forth as SEQ ID NO:3), where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Production of Immunoglobulins

Also disclosed herein are methods for producing and experimentally testing immunoglobulins. The disclosed methods are not meant to constrain embodiments to any particular application or theory of operation. Rather, the provided methods are meant to illustrate generally that one or more immunoglobulins may be produced and experimentally tested to obtain immunoglobulins. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988, all incorporated enirely by reference.

In one embodiment disclosed herein, nucleic acids are created that encode the immunoglobulins, and that may then be cloned into host cells, expressed and assayed, if desired. Thus, nucleic acids, and particularly DNA, may be made that encode each protein sequence. These practices are carried out using well-known procedures. For example, a variety of methods that may find use in generating immunoglobulins disclosed herein are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons), both incorporated entirely by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries disclosed herein. Such methods that may find use for generating immunoglobulins disclosed herein are described or referenced in U.S. Pat. No. 6,403,312; U.S. Ser. Nos. 09/782,004; 09/927,790; 10/218,102; PCT WO 01/40091; and PCT WO 02/25588, all incorporated entirely by reference. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode immunoglobulins.

The immunoglobulins disclosed herein may be produced by culturing a host cell transformed with nucleic acid, e.g., an expression vector, containing nucleic acid encoding the immunoglobulins, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in generating immunoglobulins disclosed herein are described in the ATCC® cell line catalog, available from the American Type Culture Collection.

In one embodiment, the immunoglobulins are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternateembodiment, library proteins are expressed in bacterial cells. Bacterial expression systems are well known in the art, and include *Escherichia coli* (*E. coli*), *Bacillus subtilis, Streptococcus cremoris*, and *Streptococcus lividans*. In alternate embodiments, immunoglobulins are produced in insect cells (e.g. Sf21/Sf9, *Trichoplusia ni* Bti-Tn5b1-4) or yeast cells (e.g. *S. cerevisiae, Pichia*, etc). In an alternate embodiment, immunoglobulins are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the immunoglobulins may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the immunoglobulins disclosed herein may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating immunoglobulins disclosed herein include but are not limited to those which enable protein expression in mammalian cells, bacteria, insect cells, yeast, and in in vitro systems. As is known in the art, a variety of expression vectors are available, commercially or otherwise, that may find use for expressing immunoglobulins disclosed herein.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the immunoglobulin, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Immunoglobulins may be operably linked to a fusion partner to enable targeting of the expressed protein, purification, screening, display, and the like. Fusion partners may be linked to the immunoglobulin sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs immunoglobulin and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an immunoglobulin may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen immunoglobulins (see below). Fusion partners that enable a variety of selection methods are well-known in the art. For example, by fusing the members of an immunoglobulin library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, incorporated entirely by reference). Fusion partners may enable immunoglobulins to be labeled. Alternatively, a fusion partner may bind to a specific sequence on the expression vector, enabling the fusion partner and associated immunoglobulin to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, immunoglobulins are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of immunoglobulins disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, immunoglobulins may be purified using glutathione resin if a GST fusion is employed, $Ni^{2+}$ affinity chromatography if a His-tag is employed, or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, NY, 1994, incorporated entirely by reference. The degree of purification necessary will vary depending on the screen or use of the immunoglobulins. In some instances no purification is necessary. For example in one embodiment, if the immunoglobulins are secreted, screening may take place directly from the media. As is well known in the art, some methods of selection do not involve purification of proteins. Thus, for example, if a library of immunoglobulins is made into a phage display library, protein purification may not be performed.

In Vitro Experimentation

Immunoglobulins may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the immunoglobulins disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of immunoglobulins are screened in an in vitro assay. In vitro assays may allow a broad dynamic range for screening properties of interest. Properties of immunoglobulins that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of immunoglobulins to a protein or nonprotein molecule that is known or thought to bind the immunoglobulin. In one embodiment, the screen is a binding assay for measuring binding to the target antigen. In an alternate embodiment, the screen is an assay for binding of immunoglobulins to an Fc ligand, including but not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the immunoglobulin. Assays may employ a variety of detection methods including but not limited to chromogenic, fluorescent, luminescent, or isotopic labels.

The biophysical properties of immunoglobulins, for example stability and solubility, may be screened using a variety of methods known in the art. Protein stability may be determined by measuring the thermodynamic equilibrium between folded and unfolded states. For example, immunoglobulins disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an immunoglobulin may be quantitatively or qualitatively determined using a wide range of methods that are known in the art. Methods which may find use for characterizing the biophysical properties of immunoglobulins disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an immunoglobulin could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the immunoglobulin's stability and solubility.

In one embodiment, the library is screened using one or more cell-based or in vitro assays. For such assays, immunoglobulins, purified or unpurified, are typically added exogenously such that cells are exposed to individual variants or groups of variants belonging to a library. These assays are typically, but not always, based on the biology of the ability of the immunoglobulin to bind to the target antigen and mediate some biochemical event, for example effector functions like cellular lysis, phagocytosis, ligand/receptor binding inhibition, inhibition of growth and/or proliferation, apoptosis and the like. Such assays often involve monitoring the response of cells to immunoglobulin, for example cell survival, cell death, cellular phagocytosis, cell lysis, change in cellular morphology, or transcriptional activation such as cellular expression of a natural gene or reporter gene. For example, such assays may measure the ability of immunoglobulins to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA® EuTDA-based cytotoxicity assay (Perkin Elmer, MA) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an immunoglobulin. Cell types for such assays may be prokaryotic or eukaryotic, and a variety of cell lines that are known in the art may be employed. Alternatively, cell-based screens are performed using cells that have been transformed or transfected with nucleic acids encoding the immunoglobulins.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the immunoglobulins disclosed herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the immunoglobulins disclosed herein, a particular challenge arises when using animal models to evaluate the potential for in-human efficacy of candidate polypeptides—this is due, at least in part, to the fact that immunoglobulins that have a specific effect on the affinity for a human Fc receptor may not have a similar affinity effect with the orthologous animal receptor. These problems can be further exacerbated by the inevitable ambiguities associated with correct assignment of true orthologues (Mechetina et al., *Immunogenetics,* 2002 54:463-468, incorporated entirely by reference), and the fact that some orthologues simply do not exist in the animal (e.g. humans possess an FcγRIIa whereas mice do not). Therapeutics are often tested in mice, including but not limited to mouse strains NZB, NOD, BXSB, MRL/lpr, K/B×N and transgenics (including knockins and knockouts). Such mice can develop various autoimmune conditions that resemble human organ specific, systemic autoimmune or inflammatory disease pathologies such as systemic lupus erythematosus (SLE) and rheumatoid arthritis (RA). For example, an immunoglobulin disclosed herein intended for autoimmune diseases may be tested in such mouse models by treating the mice to determine the ability of the immunoglobulin to reduce or inhibit the development of the disease pathology. Because of the incompatibility between the mouse and human Fcγ receptor system, an alternative approach is to use a murine SCID model in which immune deficient mice are engrafted with human PBLs or PBMCs (huPBL-SCID, huPBMC-SCID) providing a semi-functional human immune system with human effector cells and Fc receptors. In such a model, an antigen challenge (such as tetanus toxoid) activates the B cells to differentiate into plasma cells and secrete immunoglobulins, thus reconstituting antigen specific humoral immunity. Therefore, a dual targeting immunoglobulin disclosed herein that specifically binds to an antigen (such as CD19 or CD79a/b) and FcγRIIb on B cells may be tested to examine the ability to specifically inhibit B cell differentiation. Such experimentation may provide meaningful data for determination of the potential of said immunoglobulin to be used as a therapeutic. Other organisms, e.g., mammals, may also be used for testing. For example, because of their genetic similarity to humans, monkeys can be suitable therapeutic models, and thus may be used to test the efficacy, toxicity, pharmacokinetics, or other property of the immunoglobulins disclosed herein. Tests of the immunoglobulins disclosed herein in humans are ultimately required for approval as drugs, and thus of course these experiments are contemplated. Thus the immunoglobulins disclosed herein may be tested in humans to determine their therapeutic efficacy, toxicity, pharmacokinetics, and/or other clinical properties.

The immunoglobulins disclosed herein may confer superior performance on Fc-containing therapeutics in animal models or in humans. The receptor binding profiles of such immunoglobulins, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an immunoglobulin with reduced binding to FcγRIIIa, FcγRI and FcγRIIa can be selected to eliminate most cell-mediated effector function, or an immunoglobulin with reduced binding to C1q may be selected to limit complement-mediated effector functions. In some contexts, such effector functions are known to have potential toxic effects. Therefore eliminating them may increase the safety of the Fc-bearing drug and such improved safety may be characterized in animal models. In some contexts, such effector functions are known to mediate the desirable therapeutic activity. Therefore enhancing them may increase the activity or potency of the Fc-bearing drug and such improved activity or potency may be characterized in animal models.

In some embodiments, immunoglobulins disclosed herein may be assessed for efficacy in clinically relevant animal models of various human diseases. In many cases, relevant models include various transgenic animals for specific antigens and receptors.

Relevant transgenic models such as those that express human Fc receptors (e.g., CD32b) could be used to evaluate and test immunoglobulins and Fc-fusions in their efficacy. The evaluation of immunoglobulins by the introduction of human genes that directly or indirectly mediate effector function in mice or other rodents may enable physiological studies of efficacy in autoimmune disorders and RA. Human Fc receptors such as FcγRIIb may possess polymorphisms such as that in gene promoter (−343 from G to C) or transmembrane domain of the receptor 187 I or T which would further enable the introduction of specific and combinations of human polymorphisms into rodents. The various studies involving polymorphism-specific FcRs is not limited to this section, however encompasses all discussions and applications of FcRs in general as specified in throughout this application. Immunoglobulins disclosed herein may confer superior activity on Fc-containing drugs in such transgenic models, in particular variants with binding profiles optimized for human FcγRIIb mediated activity may show superior activity in transgenic CD32b mice. Similar improvements in efficacy in mice transgenic for the other human Fc receptors, e.g. FcγRIIa, FcγRI, etc., may be observed for immunoglobulins with binding profiles optimized for the respective receptors. Mice transgenic for multiple human receptors would show improved activity for immunoglobulins with binding profiles optimized for the corresponding multiple receptors.

Because of the difficulties and ambiguities associated with using animal models to characterize the potential efficacy of candidate therapeutic antibodies in a human patient, some variant polypeptides disclosed herein may find utility as proxies for assessing potential in-human efficacy. Such proxy molecules may mimic—in the animal system—the FcR and/or complement biology of a corresponding candidate human immunoglobulin. This mimicry is most likely to be manifested by relative association affinities between specific immunoglobulins and animal vs. human receptors. For example, if one were using a mouse model to assess the potential in-human efficacy of an Fc variant that has reduced affinity for the inhibitory human FcγRIIb, an appropriate proxy variant would have reduced affinity for mouse FcγRII. It should also be noted that the proxy Fc variants could be created in the context of a human Fc variant, an animal Fc variant, or both.

In one embodiment, the testing of immunoglobulins may include study of efficacy in primates (e.g. cynomolgus monkey model) to facilitate the evaluation of depletion of specific target cells harboring the target antigen. Additional primate models include but are not limited to use of the rhesus monkey to assess Fc polypeptides in therapeutic studies of autoimmune, transplantation and cancer.

Toxicity studies are performed to determine antibody or Fc-fusion related-effects that cannot be evaluated in standard pharmacology profiles, or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated, are evaluated for cross-reactivity with normal tissues, immunogenicity/antibody production, conjugate or linker toxicity and "bystander" toxicity of radiolabelled species. Nonetheless, such studies may have to be individualized to address specific concerns and following the guidance set by ICH S6 (Safety studies for biotechnological products, also noted above). As such, the general principles are that the products are sufficiently well characterized, impurities/contaminants have been removed, that the test material is comparable throughout development, that GLP compliance is maintained.

The pharmacokinetics (PK) of the immunoglobulins disclosed herein may be studied in a variety of animal systems, with the most relevant being non-human primates such as the cynomolgus and rhesus monkeys. Single or repeated i.v./s.c. administrations over a dose range of 6000-fold (0.05-300 mg/kg) can be evaluated for half-life (days to weeks) using plasma concentration and clearance. Volume of distribution at a steady state and level of systemic absorbance can also be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T1/2). Additional measured parameters could include compartmental analysis of concentration-time data obtained following i.v. administration and bioavailability. Examples of pharmacological/toxicological studies using cynomolgus monkeys have been established for Rituxan and Zevalin in which monoclonal antibodies to CD20 are cross-reactive. Biodistribution, dosimetry (for radiolabelled antibodies), and PK studies can also be done in rodent models. Such studies would evaluate tolerance at all doses administered, toxicity to local tissues, preferential localization to rodent xenograft animal models, and depletion of target cells (e.g. CD20 positive cells).

The immunoglobulins disclosed herein may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of immunoglobulins disclosed herein. Because immunoglobulins of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific cells or blocking signaling mechanisms, measuring inhibition of antigen-specific antibodies etc. The immunoglobulins disclosed herein may target particular effector cell populations and thereby direct Fc-containing drugs to induce certain activities to improve potency or to increase penetration into a particularly favorable physiological compartment. For example, neutrophil activity and localization can be targeted by an immunoglobulin that targets FcγRIIIb. Such pharmacodynamic effects may be demonstrated in animal models or in humans.

Clinical Use

The immunoglobulins disclosed herein may find use in a wide range of products. In one embodiment an immunoglobulin disclosed herein is a therapeutic, a diagnostic, or a research reagent. The immunoglobulins may find use in a composition that is monoclonal or polyclonal. The immunoglobulins disclosed herein may be used for therapeutic purposes. As will be appreciated by those in the art, the immunoglobulins disclosed herein may be used for any therapeutic purpose that antibodies, and the like may be used for The immunoglobulins may be administered to a patient to treat disorders including but not limited to autoimmune and inflammatory diseases, infectious diseases, and cancer.

A "patient" for the purposes disclosed herein includes both humans and other animals, e.g., other mammals. Thus the immunoglobulins disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an immunoglobulin prior to onset of the disease results in treatment of the disease. As another example, successful administration of an optimized immunoglobulin after clinical manifestation of the disease to combat the symptoms of the disease comprises treatment of the disease. "Treatment" and "treating" also encompasses administration of an optimized immunoglobulin after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an immunoglobulin disclosed herein is administered to a patient having a disease involving inappropriate expression of a protein or other molecule. Within the scope disclosed herein this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the immunoglobulins disclosed herein.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophagael cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

By "autoimmune diseases" herein include allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

By "inflammatory disorders" herein include acute respiratory distress syndrome (ARDS), acute septic arthritis, adjuvant arthritis (Prakken et al., Springer Semin Immunopathol., 2003 August; 25(1):47-63, incorporated entirely by reference), juvenile idiopathic arthritis (de Kleer et al., Arthritis Rheum. 2003 July; 47(7):2001-10, incorporated entirely by reference), allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

Some autoimmune and inflammatory diseases that may be targeted by the immunoglobulins disclosed herein include Systemic Lupus Erythematosus, Rheumatoid arthritis, Sjogren's syndrome, Multiple sclerosis, Idiopathic thrombocytopenic purpura (ITP), Graves disease, Inflammatory bowel disease, Psoriasis, Type I diabetes, and Asthma.

Immunoglobulins disclosed herein may be utilized to modulate the activity of the immune system, and in some cases to mimic the effects of IVIg therapy in a more controlled, specific, and efficient manner. Thus immunoglobulins disclosed herein may be used as immunomodulatory therapeutics. IVIg is effectively a high dose of immunoglobulins delivered intravenously. In general, IVIg has been used to downregulate autoimmune conditions. It has been hypothesized that the therapeutic mechanism of action of IVIg involves ligation of Fc receptors at high frequency (J. Bayry et al., 2003, Transfusion Clinique et Biologique 10: 165-169; Binstadt et al., 2003, J. Allergy Clin. Immunol, 697-704). Indeed animal models of (thrombocytopenia purpura (ITP) show that the isolated Fc are the active portion of IVIg (Samuelsson et al, 2001, Pediatric Research 50(5), 551). For use in therapy, immunoglobulin's are harvested from thousands of donors, with all of the concomitant problems associated with non-recombinant biotherapeutics collected from humans. An immunoglobulin disclosed herein should serve all of the roles of IVIg while being manufactured as a recombinant protein rather than harvested from donors.

The immunomodulatory effects of IVIg may be dependent on productive interaction with one or more Fc ligands, including but not limited to FcγRs, complement proteins, and FcRn. In some embodiments, immunoglobulins disclosed herein may be used to promote anti-inflammatory activity (Samuelsson et al., 2001, *Science* 291: 484-486) and or to reduce autoimmunity (Hogarth, 2002, *Current Opinion in Immunology*, 14:798-802). In one embodiment, Fc variants that provide enhanced binding to the inhibitory receptor FcγRIIb provide an enhancement to the IVIg therapeutic approach. Such Fc variants would thus function as FcγRIIb agonists, and would be expected to enhance the beneficial effects of IVIg as an autoimmune disease therapeutic and also as a modulator of B-cell proliferation. In addition, such FcγRIIb-enhanced Fc variants may also be further modified to have the same or limited binding to other receptors. In additional embodiments, the Fc variants with enhanced FcγRIIb affinity may be combined with mutations that reduce or ablate to other receptors, thereby potentially further minimizing side effects during therapeutic use.

Binding to or blocking Fc receptors on immune system cells may be used to influence immune response in immunological conditions including but not limited to idiopathic thrombocytopenia purpura (ITP) and rheumatoid arthritis (RA) among others. By use of the affinity enhanced Fc variants disclosed herein, the dosages required in typical IVIg applications may be reduced while obtaining a substantially similar therapeutic effect. Binding enhancements to FcγRIIb would increase expression or inhibitory activity, as needed, of that receptor and improve efficacy. In addition, modulated affinity of the Fc variants for activating FcγRs, FcRn, and/or also complement may also provide benefits.

Such immunomodulatory applications of the immunoglobulins disclosed herein may also be utilized in the treatment of oncological indications, especially those for which therapy involves antibody-dependant cytotoxic mechanisms. For example, an Fc variant that enhances affinity to FcγRIIb may be used to antagonize this inhibitory receptor, for example by binding to the Fc/FcγRIIb binding site but failing to trigger, or reducing cell signaling, potentially enhancing the effect of antibody-based anti-cancer therapy. Such Fc variants, functioning as FcγRIIb antagonists, may either block the inhibitory properties of FcγRIIb, or induce its inhibitory function as in the case of IVIg. An FcγRIIb antagonist may be used as co-therapy in combination with any other therapeutic, including but not limited to antibodies, acting on the basis of ADCC related cytotoxicity. FcγRIIb antagonistic Fc variants of this type may be isolated Fc or Fc fragments, although in alternate embodiments immunoglobulins may be used.

By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa, S. pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioa, leishmania, malaria, rickettsia, trypanosoma, and the like.

Furthermore, antibodies disclosed herein may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

A number of the receptors that may interact with the immunoglobulins disclosed herein are polymorphic in the human population. For a given patient or population of patients, the efficacy of the immunoglobulins disclosed herein may be affected by the presence or absence of specific polymorphisms in proteins. For example, FcγRIIIa is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et. al. (2004) Cancer Res. 64:4664-9, incorporated entirely by reference). Additional polymorphisms include but are not limited to FcγRIIa R131 or H131, and such polymorphisms are known to either increase or decrease Fc binding and subsequent biological activity, depending on the polymorphism. immunoglobulins disclosed herein may bind preferentially to a particular polymorphic form of a receptor, for example FcγRIIIa 158V, or to bind with equivalent affinity to all of the polymorphisms at a particular position in the receptor, for example both the 158V and 158F polymorphisms of FcγRIIIa. In one embodiment, immunoglobulins disclosed herein may have equivalent binding to polymorphisms may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In one embodiment, immunoglobulins disclosed herein may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIb could receive a drug containing an Fc variant with reduced binding to such polymorphic form of the receptor, creating a more efficacious drug.

In one embodiment, patients are screened for one or more polymorphisms in order to predict the efficacy of the immunoglobulins disclosed herein. This information may be used, for example, to select patients to include or exclude from clinical trials or, post-approval, to provide guidance to physicians and patients regarding appropriate dosages and treatment options. For example, in patients that are homozygous or heterozygous for FcγRIIIa 158F antibody drugs such as the anti-CD20 mAb, Rituximab are minimially effective (Carton 2002 Blood 99: 754-758; Weng 2003 J. Clin. Oncol. 21:3940-3947, both incorporated entirely by reference); such patients may show a much better clinical response to the antibodies disclosed herein. In one embodiment, patients are selected for inclusion in clinical trials for an immunoglobulin disclosed herein if their genotype indicates that they are likely to respond significantly better to an immunoglobulin disclosed herein as compared to one or more currently used immunoglobulin therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an immunoglobulin engineered to be specifically efficacious for such population, or alternatively where such therapy contains an Fc variant that does not show differential activity to the different forms of the polymorphism.

Also disclosed are diagnostic tests to identify patients who are likely to show a favorable clinical response to an immunoglobulin disclosed herein, or who are likely to exhibit a significantly better response when treated with an immunoglobulin disclosed herein versus one or more currently used immunoglobulin therapeutics. Any of a number of methods for determining FcγR polymorphisms in humans known in the art may be used.

Furthermore, also disclosed are prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In one embodiment, ADCC assays, such as those described previously, are used to predict, for a specific patient, the efficacy of a given immunoglobulin disclosed herein. Such information may be used to identify patients for inclusion or exclusion in clinical trials, or to inform decisions regarding appropriate dosages and treatment regemins. Such information may also be used to select a drug that contains a particular immunoglobulin that shows superior activity in such assay.

Formulation

Pharmaceutical compositions are contemplated wherein an immunoglobulin disclosed herein and one or more therapeutically active agents are formulated. Formulations of the immunoglobulins disclosed herein are prepared for storage by mixing said immunoglobulin having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In one embodiment, the pharmaceutical composition that comprises the immunoglobulin disclosed herein may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Some embodiments include at least one of the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration may be sterile. This is readily accomplished by filtration through sterile filtration membranes or other methods.

The immunoglobulins disclosed herein may also be formulated as immunoliposomes. A liposome is a small vesicle comprising various types of lipids, phospholipids and/or surfactant that is useful for delivery of a therapeutic agent to a mammal. Liposomes containing the immunoglobulin are prepared by methods known in the art, such as described in Epstein et al., 1985, *Proc Natl Aced Sci USA*, 82:3688; Hwang et al., 1980, *Proc Natl Aced Sci USA*, 77:4030; U.S. Pat. Nos. 4,485,045; 4,544,545; and PCT WO 97/38731, all incorporated entirely by reference. Liposomes with enhanced circulation time are disclosed in U.S. Pat. No. 5,013,556, incorporated entirely by reference. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484, incorporated entirely by reference).

The immunoglobulin and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919, incorporated entirely by reference), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an immunoglobulin disclosed herein, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the immunoglobulin may be directly applied as a solution or spray. As is known in the art, the pharmaceutical composition may be formulated accordingly depending upon the manner of introduction.

Subcutaneous administration may be used in circumstances where the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658, incorporated entirely by reference). Antibodies disclosed herein may be more amenable to subcutaneous administration due to, for example, increased potency, improved serum half-life, or enhanced solubility.

As is known in the art, protein therapeutics are often delivered by IV infusion or bolus. The antibodies disclosed herein may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Antibodies disclosed herein may be more amenable to intrapulmonary delivery. FcRn is present in the lung, and may promote transport from the lung to the bloodstream (e.g. Syntonix WO 04004798, Bitonti et al. (2004) Proc. Nat. Acad. Sci. 101:9763-8, both incorporated entirely by reference). Accordingly, antibodies that bind FcRn more effectively in the lung or that are released more efficiently in the bloodstream may have improved bioavailability following intrapulmonary administration. Antibodies disclosed herein may also be more amenable to intrapulmonary administration due to, for example, improved solubility or altered isoelectric point.

Furthermore, immunoglobulins disclosed herein may be more amenable to oral delivery due to, for example, improved stability at gastric pH and increased resistance to proteolysis. Furthermore, FcRn appears to be expressed in the intestinal epithelia of adults (Dickinson et al. (1999) J. Clin. Invest. 104:903-11, incorporated entirely by reference), so antibodies disclosed herein with improved FcRn interaction profiles may show enhanced bioavailability following oral administration. FcRn mediated transport of antibodies may also occur at other mucus membranes such as those in the gastrointestinal, respiratory, and genital tracts (Yoshida et al. (2004) Immunity 20:769-83, incorporated entirely by reference).

In addition, any of a number of delivery systems are known in the art and may be used to administer the antibodies disclosed herein. Examples include, but are not limited to, encapsulation in liposomes, microparticles, microspheres (e.g., PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the Lupron Depot®, and poly-D-(−)-3-hydroxyburyric acid. It is also possible to administer a nucleic acid encoding an immunoglobulin disclosed herein, for example by retroviral infection, direct injection, or coating with lipids, cell surface receptors, or other transfection agents. In all cases, controlled release systems may be used to release the immunoglobulin at or close to the desired location of action.

Dosing

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active immunoglobulin in the formulation may vary from about 0.1 to 100 weight %. In one embodiment, the concentration of the immunoglobulin is in the range of 0.003 to 1.0 molar. In order to treat a patient, a therapeutically effective dose of the immunoglobulin disclosed herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight. In one embodiment, dosages range from 1 to 10 mg/kg.

In some embodiments, only a single dose of the immunoglobulin is used. In other embodiments, multiple doses of the immunoglobulin are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies disclosed herein are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the immunoglobulin disclosed herein and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The antibodies disclosed herein may be administered concomitantly with one or more other therapeutic regimens or agents. The additional therapeutic regimes or agents may be used to improve the efficacy or safety of the immunoglobulin.

Also, the additional therapeutic regimes or agents may be used to treat the same disease or a comorbidity rather than to alter the action of the immunoglobulin. For example, an immunoglobulin disclosed herein may be administered to the patient along with chemotherapy, radiation therapy, or both chemotherapy and radiation therapy. The immunoglobulin disclosed herein may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, FcγRIIb or other Fc receptor inhibitors, or other therapeutic agents.

The terms "in combination with" and "co-administration" are not limited to the administration of said prophylactic or therapeutic agents at exactly the same time. Instead, it is meant that the immunoglobulin disclosed herein and the other agent or agents are administered in a sequence and within a time interval such that they may act together to provide a benefit that is increased versus treatment with only either the immunoglobulin disclosed herein or the other agent or agents. In some embodiments, immunoglobulins disclosed herein and the other agent or agents act additively, and sometimes synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the antibodies disclosed herein are administered with one or more additional molecules comprising antibodies or Fc. The antibodies disclosed herein may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti-17-1A cell surface antigen antibodies such as Panorex™ (edrecolomab); anti-4-1BB antibodies; anti-4Dc antibodies; anti-A33 antibodies such as A33 and CDP-833; anti-α4β1 integrin antibodies such as natalizumab; anti-α4β7 integrin antibodies such as LDP-02; anti-αVβ1 integrin antibodies such as F-200, M-200, and SJ-749; anti-αVβ3 integrin antibodies such as abciximab, CNTO-95, Mab-17E6, and Vitaxin™; anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX-CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab, I-131 labeled anti-CD20), Rituxan® (rituximab), and Zevalin® (Ibritumomab tiuxetan, Y-90 labeled anti-CD20); anti-CD22 antibodies such as Lymphocide™ (epratuzumab, Y-90 labeled anti-CD22); anti-CD23 antibodies such as IDEC-152; anti-CD25 antibodies such as basiliximab and Zenapax® (daclizumab); anti-CD30 antibodies such as AC10, MDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN-40 and toralizumab; anti-CD40L antibodies such as 5c8, Antova™, and IDEC-131; anti-CD44 antibodies such as bivatuzumab; anti-CD46 antibodies; anti-CD52 antibodies such as Campath® (alemtuzumab); anti-CD55 antibodies such as SC-1; anti-CD56 antibodies such as huN901-DM1; anti-CD64 antibodies such as MDX-33; anti-CD66e antibodies such as XR-303; anti-CD74 antibodies such as IMMU-110; anti-CD80 antibodies such as galiximab and IDEC-114; anti-CD89 antibodies such as MDX-214; anti-CD123 antibodies; anti-CD138 antibodies such as B-B4-DM1; anti-CD146 antibodies such as AA-98; anti-CD148 antibodies; anti-CEA antibodies such as cT84.66, labetuzumab, and Pentacea™; anti-CTLA-4 antibodies such as MDX-101; anti-CXCR4 antibodies; anti-EGFR antibodies such as ABX-EGF, Erbitux® (cetuximab), IMC-C225, and Merck Mab 425; anti-EpCAM antibodies such as Crucell's anti-EpCAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies; anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and TriGem; anti-GD3 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Muc1 antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antbodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGF-β antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies; anti-VE-cadherin-2 antibodies; and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC- 131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcγR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, and anti-TNFa antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the antibodies disclosed herein may be co-administered or with one or more other molecules that compete for binding to one or more Fc receptors. For example, co-administering inhibitors of the inhibitory receptor FcγRIIb may result in increased effector function. Similarly, co-administering inhibitors of the activating receptors such as FcγRIIIa may minimize unwanted effector function. Fc receptor inhibitors include, but are not limited to, Fc molecules that are engineered to act as competitive inhibitors for binding to FcγRIIb FcγRIIIa, or other Fc receptors, as well as other immunoglobulins and specifically the treatment called IVIg (intravenous immunoglobulin). In one embodiment, the inhibitor is administered and allowed to act before the immunoglobulin is administered. An alternative way of achieving the effect of sequential dosing would be to provide an immediate release dosage form of the Fc receptor inhibitor and then a sustained release formulation of an immunoglobulin disclosed herein. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the antibodies disclosed herein are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11;retinoic acid; esperamicins; capecitabine. Pharmaceutically acceptable salts, acids or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt et al., (ed.): 247-267, Humana Press, 1985, all incorporated entirely by reference. The prodrugs that may find use with immunoglobulins disclosed herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies disclosed herein include but are not limited to any of the aforementioned chemotherapeutic agents.

A variety of other therapeutic agents may find use for administration with the antibodies disclosed herein. In one embodiment, the immunoglobulin is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. In one embodiment, an anti-angiogenic factor may be an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the antibody is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CA1, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activiator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-13), vasculostatin, vasostatin (calreticulin fragment), ZS6126, and ZD6474.

In one embodiment, the immunoglobulin is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI571, Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804, 396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/ 3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech), all patent publications incorporated entirely by reference.

In another embodiment, the immunoglobulin is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but not limited to: non-steroidal anti-inflammatory drugs (NSAIDs) such as asprin, ibuprofed, celecoxib, diclofenac, etodolac, fenoprofen, indomethacin, ketoralac, oxaprozin, nabumentone, sulindac, tolmentin, rofecoxib, naproxen, ketoprofen, and nabumetone; steroids (eg. glucocorticoids, dexamethasone, cortisone, hydroxycortisone, methylprednisolone, prednisone, prednisolone, trimcinolone, azulfidine-icosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFNα, IFNIβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFIβ, TNFα, TNFβ, TNF-R1, T-cell receptor, including Enbrel® (etanercept), Humira® (adalimumab), and Remicade® (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (eg. leflunomide), methotrexate, minocycline, mizoribine, mycophenolate mofetil, rapamycin, and sulfasasazine.

In an alternate embodiment, immunoglobulins disclosed herein are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In one embodiment, cytokines or other agents that stimulate cells of the immune system are co-administered with the immunoglobulin disclosed herein. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et al. (2003) Scand. J. Immunol. 57: 221-8, incorporated entirely by reference), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the immunoglobulin disclosed herein. Such a mode of treatment may limit unwanted effector function.

In an additional embodiment, the immunoglobulin is administered with one or more antibiotics, including but not limited to: aminoglycoside antibiotics (e.g. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefinetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg. flomoxef, latamoxef, and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (amifloxacin, cinoxacin, ciprofloxacin, enoxacin, enrofloxacin, feroxacin, flumequine, gatifloxacin, gemifloxacin, grepafloxacin, lomefloxacin, moxifloxacin, nalidixic acid, norfloxacin, ofloxacin, oxolinic acid, pefloxacin, pipemidic acid, rosoxacin, rufloxacin, sparfloxacin, temafloxacin, tosufloxacin, trovafloxacin); rifampin; streptogramins (eg. quinupristin, dalfopristin); sulfonamides (sulfanilamide, sulfamethoxazole); tetraclyenes (chlortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazole, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine, may be used.

The antibodies disclosed herein may be combined with other therapeutic regimens. For example, in one embodiment, the patient to be treated with an immunoglobulin disclosed herein may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another, an immunoglobulin disclosed herein and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with immunoglobulin and one or more other anti-cancer therapies, such as described above, can be employed to deplete or substantially deplete the cancer cells prior to transplantation in a recipient patient.

It is of course contemplated that the antibodies disclosed herein may employ in combination with still other therapeutic techniques such as surgery or phototherapy.

EXAMPLES

Examples are provided below are for illustrative purposes only. These examples are not meant to constrain any embodiment disclosed herein to any particular application or theory of operation.

Example 1

Novel Methods for Inhibiting FcγRIIb$^+$ Cells

FcγRIIb is expressed on a variety of immune cells, including B cells, plasma cells, dendritic cells, monocytes, and macrophages, where it plays a critical role in immune regulation. In its normal role on B cells, FcγRIIb serves as a feedback mechanism to modulate B cell activation through the B cell receptor (BCR). Engagement of B cell antigen receptor (BCR) by immune complexed antigen on mature B cells activates an intracellular signaling cascade, including calcium mobilization, which leads to cell proliferation and differentiation. However, as IgG antibodies with specificity to the antigen are produced, the associated immune complexes (ICs) can crosslink the BCR with FcγRIIb, whereupon the activation of BCR is inhibited by engagement of FcγRIIb and associated intracellular signaling pathways that interfere with the downstream pathways of BCR activation.

B cells function not only to produce antibodies and cytokines that control immune response, they are also antigen presenting cells (APCs). Internalization of antigen by BCR into a B cell can play a role in presentation to and activation of T cells. Regulation of B cell activation through the BCR is also potentially regulated by antibody engagement of FcγRIIb. Other APCs such as dendritic cells, macrophages, and monocytes, are capable of internalizing antibody-bound antigen through activating receptors such as FcγRIIa, FcγRIIIa, and FcγRI. Expression of FcγRIIb on these cell types, particularly dendritic cells, can inhibit activation of these cell types and subsequent presentation to and activation of T cells (Desai et al., 2007, J Immunol).

A novel strategy for inhibiting activation of the aforementioned cell types it to use a single immunoglobulin to coengage FcγRIIb with surface antigen present on the FcγRIIb+ cell. In the case of B cells, based on the natural biological mechanism, this would potentially involve dual targeting of FcγRIIb and BCR, with the goal of mimicking immune complex-mediated suppression of B cell activation. FIG. 3 illustrates one such potential mechanism, in which an antibody is used to coengage both FcγRIIb via its Fc region, and a target antigen associated with BCR complex, in this example CD19, via its Fv region.

Example 2

Engineering Immunoglobulins with Selectively Enhanced Affinity for FcγRIIb

Under physiological conditions, bridging of the BCR with FcγRIIb and subsequent B cell suppression occurs via immune complexes of IgGs and cognate antigen. The design strategy was to reproduce this effect using a single crosslinking antibody. Human IgG binds human FcγRIIb with weak affinity (approximately 1 µM for IgG1), and FcγRIIb-mediated inhibition occurs in response to immune-complexed but not monomeric IgG. It was reasoned that increasing Fc affinity to this receptor would be required for maximal inhibition of B cell activation. Protein engineering methods were used to design and screen Fc variants for enhanced FcγRIIb binding.

In addition to this primary design goal (maximal Fc affinity to FcγRIIb), a secondary design goal was to reduce interaction of the Fc region with activating FcγRs. FcγR affinity profiles that may be optimal for inhibiting FcγRIIb cells include not only high affinity for the inhibitory receptor FcγRIIb, but also potentially high FcγRIIb affinity coupled with reduced affinity for one or more activating receptors, including, for example, FcγRI, FcγRIIIa, and/or FcγRIIa. Reduced affinity to activating receptors may lead to reduced toxicity associated with an antibody treatment. For example, reduced affinity to FcγRIIIa, present on NK cells, should reduce the level of NK cell-mediated ADCC. Similarly, reduced affinity to FcγRIIa, present on a variety of effector cells including macrophages and neutrophils, should reduce the level of phagocytosis (ADCP) mediated by these cells. In addition, for monocytes, macrophages, dendritic cells, and the like, reduced interaction with activating FcγRs would mean that immunoglobulin would be more free to interact with FcγRIIb on the cell surface.

Using solved structures of the human Fc/FcγRIIIb complex (and the sequences of the human FcγRs, structural and sequence analysis were used to identify FcγR positions that contribute to FcγRIIb affinity and selectivity relative to the activating receptors. The design strategy employed two steps. First, FcγR positions that are determinants of FcγRIIb and FcγRIIIa binding selectivity were identified by accounting for proximity to the FcγR/Fc interface and amino acid dissimilarity between FcγRIIb and FcγRIIIa. The results of this analysis are presented in FIG. 4. Second, sequence positions in the Fc region proximal to these FcγR positions were identified. The results of this analysis are presented in FIG. 5. Fc variants were designed that incorporate substitutions at these positions.

A library of Fc variants was generated and screened to explore amino acid modifications at these positions. Variants were generated and screened in the context of an antibody targeting the antigen CD19, a regulatory component of the BCR coreceptor complex. The Fv region of the this antibody is a humanized and affinity matured version of antibody 4G7, and is referred to herein as HuAM4G7. The amino acid sequences of this antibody are provided in FIG. 54A-FIG. 54D. The Fv genes for this antibody were subcloned into the mammalian expression vector pTT5 (National Research Council Canada). Mutations in the Fc domain were introduced using site-directed mutagenesis (QuikChange, Stratagene, Cedar Creek, Tex.). In addition, control knock out variants with ablated affinity for Fc receptors were generated that comprise the substitution L328R, and either a G236R substitution or an Arg inserted after position 236. These variants (G236R/L328R and ^236R/L328R) are referred to as Fc-KO or FcγR knockout. To serve as non-CD19 Fc isotype controls, anti-respiratory syncytial virus (RSV) and anti-FITC antibodies were constructed in the pTT5 vector by fusing the appropriate $V_L$ and $V_H$ regions to the $C_L\kappa$ and $C_H1$-3 domains with Fc changes. Heavy and light chain constructs were cotransfected into HEK293E cells for expression, and antibodies were purified using protein A affinity chromatography (Pierce Biotechnology, Rockford, Ill.).

Human Fc receptor proteins FcγRI and FcγRIIb for binding and competition studies were obtained from R&D Systems (Minneapolis, Minn.). Genes encoding FcγRIIa and FcγRIIIa receptor proteins were obtained from the Mammalian Gene Collection (ATCC), and subcloned into pTT5 vector (National Research Council Canada) containing 6×His and GST-tags. Allelic forms of the receptors (H131 and R131 for FcγRIIa and V158 and F158 for FcγRIIIa) were generated using QuikChange mutagenesis. Vectors encoding the receptors were transfected into HEK293T cells, and proteins were purified using nickel affinity chromatography.

Variants were screened for receptor affinity using Biacore™ technology, also referred to as Biacore herein, a surface plasmon resonance (SPR) based technology for studying biomolecular interactions in real time. SPR measurements were performed using a Biacore 3000 instrument (Biacore, Piscataway, N.J.). A protein A/G (Pierce Biotechnology) CM5 biosensor chip (Biacore) was generated using a standard primary amine coupling protocol. All measurements were performed using HBS-EP buffer (10 mM HEPES pH 7.4, 0.15 M NaCl, 3 mM EDTA, 0.005% vol/vol surfactant P20, Biacore). Antibodies at 20 nM or 50 nM in HBS-EP buffer were immobilized on the protein A/G surface and FcγRs were injected. After each cycle, the surface was regenerated by injecting glycine buffer (10 mM, pH 1.5). Data were processed by zeroing time and response before the injection of FcγR and by subtracting appropriate nonspecific signals (response of reference channel and injection of running buffer). Kinetic analyses were performed by global fitting of binding data with a 1:1 Langmuir binding model using BIAevaluation software (Biacore).

A representative set of sensorgrams for binding of select variant anti-CD19 antibodies to FcγRIIb is shown in FIG. 6. The affinities (equilibrium Kds) of all variants and WT (native) IgG1 to all of the FcγRs, obtained from fits of the Biacore binding data, are presented in FIG. 7A-FIG. 7D. Whereas WT IgG1 Fc binds with FcγRIIb with μM affinity (Kd=1467 nM in FIG. 7), a large number of variants have been engineered that bind more tightly. Because all of the antibodies tested have specificity for CD19 (via their Fv region), the binding results in FIG. 7A-FIG. 7D are due solely to binding to FcγRIIb by the Fc region. This is supported by the lack of detectable binding by the Fc-KO variants (G236R/L328R and ^236R/L328R), which are ablated for binding to all FcγRs.

A useful quantity for analysis of the variants is their fold affinity relative to WT IgG1, which is generated by dividing the Kd for binding of WT IgG1 by the Kd for binding of variant for each receptor. These fold affinity results are provided in FIG. 8A-FIG. 8D. A number of variants have FcγRIIb binding enhancements over 2 logs, and substantially reduced or ablated affinities for the activating receptors. In particular, S267E (single substitution) as well as L235Y/S267E, G236D/S267E, S239D/S267E, S267E/H268E, and S267E/L328F (double substitutions) have markedly higher affinity for FcγRIIb. In addition, these variant have affinity for the activating receptor FcγRIIIa that is either comparable to native IgG1, modestly enhanced, or even significantly reduced.

FIG. 9 shows a plot of the FcγR affinities of select variants on a log scale, compared with those of WT IgG1. The variant with the highest affinity for FcγRIIb, S267E/L328F, shows over 2 orders of magnitude improvement in affinity to FcγRIIb, and significantly reduced affinity to the activating receptors, including FcγRIIIa, FcγRI, and H131 FcγRIIa.

The data in FIGS. 9 and 10 indicate that the properties of the variants are highly dependent not only on the position that is mutated, but also the precise amino acid that is substituted at each position. For example, one of the strongest positions for controlling FcγRIIb affinity and selectivity relative to activating FcγRs is position 267. Yet modification at this position can yield dramatically different results depending on the particular amino acid that is substituted In particular, as shown in FIG. 10, whereas affinity of S267E for FcγRIIb is greatly enhanced relative to WT IgG1 and provides substantial selectivity improvement relative to FcγRIIIa, other substitutions such as S267A and S267G provide either marginal or no FcγRIIb enhancement, and/or little or no selectivity improvement relative to FcγRIIIa. The importance of the precise modification is further supported by the fact that two of the best positions for selectively enhancing FcγRIIb affinity, 236 and 328 (for example 236D and 328F) are also the same positions that are modified to generate the Fc-KO variant (236R and 328R). These results illustrate the complexity of the FcγR interface, and highlight the challenge of engineering modifications that precisely control desired FcγR properties.

Many of the Fc combination variants, including double and triple combinations of single substitutions, exhibited unexpected synergy (non-additivity) when compared against the single substitutions alone. This was determined (for all combination variants for which data was available) by comparing the actual fold improvement in affinity as measured by Biacore versus the expected fold improvement in affinity as calculated by the product of the fold improvements of the single substitutions (FIG. 11). As can be seen from the data, double substitutions at the following pairs of positions resulted in a greater than expected affinity for one or more FcγRs: 234/267, 235/267, 236/267, 236/268, 239/267, 239/268, 266/267, 267/328, and 268/327.

In order to validate the Biacore data and evaluate receptor binding of the variants on the cell surface, binding of select antibodies to cells expressing FcγRIIb was measured. Since HEK293T cells do not express CD19 or FcγRs, transfection of these cells with FcγRIIb allowed an analysis of antibody binding to Fc receptors in an isolated system on a cell surface. HEK293T cells in DMEM with 10% FBS were transfected with human FcγRIIb cDNA in pCMV6 expression vector (Origene Technologies, Rockville, Md.), cultured for 3 days, harvested, washed twice in PBS, resuspended in PBS with 0.1% BSA (PBS/BSA), and aliquoted at $2\times10^5$ cells per well into 96-well microtiter plates. Fc variant antibodies were serially diluted in PBS/BSA then added to the cells and incubated with mixing for 1 h at room temperature. After extensive washing with PBS/BSA, phycoerythrin (PE)-labeled anti-human-Fab-specific goat F(ab')2 fragment was added for detection. Cells were incubated for 30 min at room temperature, washed, and resuspended in PBS/BSA. Binding was evaluated using a FACSCanto II flow cytometer (BD Biosciences, San Jose, Calif.), and the mean fluorescence intensity (MFI) was plotted as a function of antibody concentration using Graph Pad Prism software (GraphPad Software, San Diego, Calif.) from which half-maximal binding (EC50) values were determined by sigmoidal dose response modeling.

Receptor expression levels were assessed prior to binding of antibodies, and half-maximal effective concentration (EC50) values of the MFI at different antibody concentrations were determined. FIG. 12 shows the results of this experiment. The EC50 values of the variants tested showed a similar rank order as the Biacore results. The cell-surface binding confirmed that the S267E/L328F variant of those tested has the highest affinity for FcγRIIb, with an EC50 approximately 320-fold relative to WT IgG1. The strong agreement between these cell surface binding data and the Biacore binding data support the accuracy of the affinity measurements.

Because of the importance of animal models in drug development, select variants were screened further for binding to mouse and cynomolgous monkey receptors. The extracellular regions of mouse and cynologous monkey (*Macaca fascicularis*) FcγRs were expressed and purified. The extracellular regions of these receptors were obtained by PCR from clones obtained from the Mammalian Gene Collection (MGC), or generated de novo using recursive PCR. To enable purification and screening, receptors were fused C-terminally with a His- and GST-tag. Tagged FcγRs were transfected into 293T cells, and media containing secreted receptor were harvested 3 days later and purified using Nickel chromatography.

Variant antibodies were tested for their affinity to mouse or cynologous monkey FcγRs using Biacore SPR as described above. Specifically, antibodies were first immobilized on a protein A/G chip to high density, and then followed by injections of the extracellular domain of the mouse or cynologous monkey FcγR of interest. Both association and dissociation phases were tracked in real time using the Biacore technology. FIG. 13A-FIG. 13D show the fold improvements (compared to WT IgG1) for binding of select variants to mouse and cynologous monkey FcγRs as determined from Biacore.

Although the variants were screened in the context of human IgG1, it is contemplated that the variants could be used in the context of other antibody isotypes, for example including but not limited to human IgG2, human IgG3, and human IgG4 (FIG. 1). In order to explore the transferability of the variants to other antibody isotypes, the S267E/L328F variant was constructed and tested in the context of a IgG1/2 ELLGG antibody, which is a variant of an IgG2 Fc region (U.S. Ser. No. 11/256,060, herein expressly incorporated by reference). The mutations were constructed, antibodies purified, and binding data carried out as described above. FIG. 14 shows affinities of the IgG1 and IgG1/2 variant antibodies to the human FcγRs as determined by Biacore. The data indicate that the greatly enhanced FcγRIIb affinity and the overall FcγR binding profile are maintained in the variant IgG2 Fc region, thus supporting the use of the variants in other isotype contexts.

Collectively, the above data indicate that a number of engineered variants, at specific Fc positions, provide the targeted properties, namely enhanced affinity for FcγRIIb, and selectively enhanced FcγRIIb affinity relative to the activating receptors FcγRI, FcγRIIa, and FcγRIIIa. Substitutions to enhance affinity to FcγRIIb include: 234, 235, 236, 237, 239, 266, 267, 268, 325, 326, 327, 328, and 332. In some embodiments, substitutions are made to at least one or more of the nonlimiting following positions to enhance affinity to FcγRIIb: 235, 236, 239, 266, 267, 268, and 328.

Nonlimiting combinations of positions for making substitutions to enhance affinity to FcγRIIb include: 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332. In some embodiments, combinations of positions for making substitutions to enhance affinity to FcγRIIb include, but are not limited to: 235/267, 236/267, 239/268, 239/267, 267/268, and 267/328.

Substitutions for enhancing affinity to FcγRIIb include: L234D, L234E, L234W, L235D, L235F, L235R, L235Y, G236D, G236N, G237D, G237N, S239D, S239E, V266M, S267D, S267E, H268D, H268E, A327D, A327E, L328F, L328W, L328Y, and I332E. In some embodiments, combination of positions for making substitutions for enhancing affinity to FcγRIIb include, but are not limited to: L235Y, G236D, S239D, V266M, S267E, H268D, H268E, L328F, L328W, and L328Y.

Combinations of substitutions for enhancing affinity to FcγRIIb include: L234D/S267E, L234E/S267E, L234F/S267E, L234E/L328F, L234W/S239D, L234W/S239E, L234W/S267E, L234W/L328Y, L235D/S267E, L235D/L328F, L235F/S239D, L235F/S267E, L235F/L328Y, L235Y/G236D, L235Y/S239D, L235Y/S267D, L235Y/S267E, L235Y/H268E, L235Y/L328F, G236D/S239D, G236D/S267E, G236D/H268E, G236D/L328F, G236N/S267E, G237D/S267E, G237N/S267E, S239D/S267D, S239D/S267E, S239D/H268D, S239D/H268E, S239D/A327D, S239D/L328F, S239D/L328W, S239D/L328Y, S239D/I332E, S239E/S267E, V266M/S267E, S267D/H268E, S267E/H268D, S267E/H268E, S267E/N325L, S267E/A327D, S267E/A327E, S267E/L328F, S267E/L3281, S267E/L328Y, S267E/I332E, H268D/A327D, H268D/L328F, H268D/L328W, H268D/L328Y, H268D/I332E, H268E/L328F, H268E/L328Y, A327D/L328Y, L328F/I332E, L328W/I332E, and L328Y/I332E. In some embodiments, combinations of substitutions for enhancing affinity to FcγRIIb include, but are not limited to: L235Y/S267E, G236D/S267E, S239D/H268D, S239D/S267E, S267E/H268D, S267E/H268E, and S267E/L328F.

Example 3

Immunoglobulins Inhibit BCR-Mediated Primary Human B Cell Viability

Although normal B cells have a long in vivo half life of approximately five weeks, their lifespan is greatly reduced in vitro. BCR stimulation by crosslinking antibodies such as anti-IgM or anti-CD79b counteracts this in vitro predisposition towards apoptosis, leading to B cell activation and increased B cell viability. To demonstrate this, an ATP-dependent B cell viability assay was performed. Human peripheral blood mononuclear cells (PBMCs) were purified from leukapheresis of anonymous healthy volunteers (HemaCare, Van Nuys, Calif.) using Ficoll-Paque Plus density gradients (Amersham Biosciences, Newark, N.J.). Primary human B cells were purified from PBMCs using a B cell enrichment kit (StemCell Technologies, Vancouver, British Columbia). Murine anti-human CD79b (clone SN8) was purchased from Santa Cruz Biotechnology (Santa Cruz, Calif.). Polyclonal anti-mu F(ab')2 was purchased from Jackson Immunoresearch Lab (West Grove, Pa.). Anti-mu or anti-CD79b antibody serial dilutions were performed in triplicate in 96-well microtiter plates containing RPMI1640 with 10% FBS. Purified primary human B cells (5–7.5×104 per well) were added to a final volume of 100 µl, and incubated at 37° C. for 3 days. ATP-dependent luminescence was quantified to determine cell viability (Cell Titer-Glo Cell Viability Assay, Promega, Madison, Wis.) and a Topcount luminometer (PerkinElmer, Waltham, Mass.) was used for data acquisition. FIGS. 15A and 15B show the results of the assay, demonstrating the survival of primary human B cells upon BCR activation, here carried out by crosslinking with anti-mu (A) or anti-CD79b (B) antibodies. In vivo such activation would occur via immune complexed antigen, which for example could be an infectious agent, or in the cause of an autoimmune or allergic reaction could be an anutoimmune antigen or allergen.

The ATP-dependent luminescence assay was used to examine if BCR activation-mediated viability of primary human B cells could be suppressed by an anti-CD19 antibody having enhanced Fc affinity for FcγRIIb. The above experiment was repeated, except that antibody serial dilutions of WT, variant, and control antibodies were performed in triplicate in 96-well microtiter plates containing RPMI1640 with 10% FBS, plus anti-CD79b at 1 µg/ml to stimulate BCR. The results are shown in FIG. 16. Again, B cells possessed low viability in the absence of BCR crosslinking, and addition of 10 µg/ml anti-CD79b antibody stimulated survival by about 6-fold (cells alone vs. anti-CD79b). Anti-CD19-S267E/L328F, the variant with the highest FcγRIIb affinity, inhibited BCR-stimulated viability in a dose-dependent manner. In contrast, control antibodies including anti-CD19-IgG1 (Fv control) and anti-RSV-S267E/L328F (Fc control) minimally suppressed viability. To assess if this inhibitory effect required coengagement of CD19 and FcγRIIb, as opposed to simultaneous binding of each receptor by different antibodies, the anti-CD19-S267E/L328F variant was compared to a combination of anti-CD19-IgG1 and anti-RSV-S267E/L328F controls at equal concentrations. The combination of these antibodies should simultaneously bind to both CD19 and FcγRIIb but, unlike anti-CD19-S267E/L328F, is unable to crosslink these receptors. As shown in FIG. 16, the combination failed to suppress BCR activation-induced survival, indicating that coengagement of FcγRIIb and CD19 by a single molecule is required to inhibit BCR-mediated viability. Not all variants were capable of inhibiting B cell activation. As demonstrated in FIG. 17, variants with moderately increased affinity relative to WT IgG1 (S267A, 408 nM, 3.6-fold relative to native IgG1) do not inhibit B cell activation. In contrast, that data in FIG. 18 demonstrate that variants with high affinity, here the weakest affinity being the S267E variant (71.9 nM, 20.4-fold relative to native IgG1), do indeed inhibit activation. Together the results in FIGS. 18, 19, and 20 suggest that a certain high affinity for FcγRIIb, about 100 nM, is needed to mediate inhibitory activity upon coengagement of FcγRIIb and BCR co-receptor target antigen.

Example 4

Immunoglobulins Inhibit BCR Activation of Calcium Mobilization in Primary Human B Cells Via Coengagement of FcγRIIb and CD19

Signals through the B-cell receptor complex ultimately result in calcium release, and this pathway can be inhibited by FcγRIIb (Nielsen et al., 2005, Transfus Med Hemother 32:339-347, incorporated entirely by reference). Intracellular calcium mobilization was used as a quantitative measure of BCR-mediated B cell activation to further evaluate the impact of the immunoglobulins. The current study used primary B cells from normal human donors as a more physiologically relevant model of calcium signaling. In addition, rather than stimulating primarily naive B cells via an anti-IgM antibody, an anti-human CD79b (Igβ) antibody was used in order to induce BCR activation in both naive and memory B cells.

Intracellular free calcium concentration ([Ca2+]) was measured by flow cytometry using a Fluo-4 NW calcium assay (Molecular Probes, Eugene, Oreg.). Purified human B cells were resuspended at 5×105 cells/ml in calcium assay buffer and pre-loaded with Fluo-4 dye for 30 min at room temperature. After incubation with anti-CD19 or Fc and Fv control antibodies, cells were stimulated by addition of 10 µg/ml of anti-CD79b antibody. Calcium flux kinetics was recorded using a FACSCanto II flow cytometer and data were analyzed using FlowJo software (Tree Star, Ashland, Oreg.).

Calcium mobilization in the presence of 10 µg/ml anti-CD19 native IgG1 Fc antibody (α-CD19-native-IgG1) was increased relative to the vehicle control (FIG. 19), as expected from coengagement of CD19 and BCR. In contrast, IIbE variants of anti-CD19 IgG1 (also at 10 µg/ml) inhibited calcium mobilization induced by BCR crosslinking, with the two highest-affinity variants showing greatest activity. To determine the importance of CD19 binding for this effect, an Fc isotype control antibody was used that binds with high affinity to FcγRIIb but not to CD19; this antibody, referred to as a-FITC-S267E/L328F in FIG. 19, has the S267E/L328F IgG1 heavy chain, but an Fv region that binds the hapten FITC (which is not on B cells). Relative to vehicle, this antibody had minimal effect on calcium mobilization, indicating that CD19 binding is required to inhibit calcium mobilization. A dose-response extension of this experiment was carried out in which each point represents the area under the curve of a single calcium mobilization response as in FIG. 19. The data show that potency and efficacy of IIbE variants correlated with affinity for FcγRIIb, consistent with the B cell viability assay, with anti-CD19-Native-IgG1 showing no dose response (FIG. 20). The relationship between the EC50 of calcium inhibition and affinity for FcγRIIb is shown in FIG. 21.

To assess if the observed inhibition of calcium flux required engagement of both FcγRIIb and CD19 by a single antibody, a competition experiment was performed. Because FcγRI has the highest affinity among all the FcγRs (FIG. 9) and competes with FcγRIIb for IgG binding (data not shown), a 24-fold molar excess soluble FcγRI (solFcγRI) to block the interaction of the highest affinity antibody (α-CD19-S267E/L328F) with FcγRIIb (FIG. 22). BCR-induced calcium mobilization was again effectively inhibited by 10 µg/ml α-CD19-S267E/L328F, but not by α-CD19-Native-IgG1. Notably, inhibition by the IIbE variant was completely abolished in the presence of soluble FcγRI, indicating that FcγRIIb engagement is required. These results indicate that BCR-induced calcium mobilization can be inhibited by a single antibody that binds with high affinity to both FcγRIIb and CD19 surface receptors.

Together the B cell viability and calcium mobilization results suggest that Fc variant antibodies with high affinity for FcγRIIb may be useful in methods for inhibiting activation of B cells. The data provided indicate that amino acid modification at positions 234, 235, 236, 237, 239, 266, 267, 268, 325, 326, 327, 328, and 332 may be useful for such inhibitory methods. In particular, the data provided indicate that substitutions 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and I332E may be useful for such inhibitory methods.

Example 5

Immunoglobulins Induce SHIP Phosphorylation

SHIP activation is an FcγRIIb-dependent downstream component of ITIM-associated signaling. The capacity of the anti-CD19-S267E/L328F antibody to stimulate SHIP phosphorylation (pSHIP) in the context of BCR activation by anti-CD79b crosslinking antibody was assessed using western analysis. Purified primary human B cells (1×107) were incubated for 10 min at 22° C. with 20 µg/ml anti-CD79b and 10 µg/ml anti-CD19 antibodies, and then ice-cold PBS was added. For the positive control, 10 µg/ml of anti-FcγRII-specific antibody (AT10) (AbD Serotec (Raleigh, N.C.) was used to crosslink FcγRIIb, and 20 µg/ml anti-mouse IgG Fcγ-specific antibody was used to crosslink AT10 and anti-CD79b. Cells were lysed in cold RIPA buffer (Cell Signaling, Beverly, Mass.) containing protease (Roche, Indianapolis, Ind.) and phosphatase (Calbiochem, San Diego, Calif.) inhibitor cocktails with 2 nM microcystin (Calbiochem), and incubated for 30 min on ice. Lysates were centrifuged at 10,000 g for 30 min at 4° C. to remove debris, fractionated by SDS-PAGE (NuPAGE Novex, Invitrogen Life Technologies, Carlsbad, Calif.) and transferred to polyvinylidene difluoride membrane (Invitrogen Life Technologies). Western analysis was performed with phospho-SHIP (Cell Signaling Technologies, Beverly, Mass.) and GAPDH-specific primary antibodies (Biovision, Mountain View, Calif.) using HRP-conjugated anti-mouse IgG secondary antibody with enhanced chemiluminescence imaging (Amersham Bioscience, Newark, N.J.) and a UVP Bioimaging image capturing system (Upland, Calif.).

The data are presented in FIG. 23. The western blot of cell extracts from purified primary human B cells showed that the anti-CD19 IIbE variant stimulated a substantial increase in pSHIP level compared to anti-CD19 IgG1 and other controls (anti-RSV-S267E/L328F and anti-CD19-Fc-KO) (FIG. 23, lane 1 vs. lanes 2-4). As expected, direct crosslinking of FcγRIIb with BCR by anti-FcγRII antibody also showed an increase in pSHIP level (lane 5). These results indicate that suppression of B cell function by the anti-CD19 IIbE antibody stimulates SHIP phosphorylation, which is consistent with a known signaling pathway of BCR-FcγRIIb coengagement.

Example 6

Immunoglobulins Inhibit BCR-Dependent Anti-apoptotic Effect in Primary Human B Cells Although normal B cells in vivo have a long half life of approximately ~5 weeks, in vitro this lifespan is greatly reduced, with increased apoptosis due to the lack of appropriate niche. B cell activation via stimulation via the BCR induces an anti-apoptotic effect and prolongs viability, as demonstrated in FIG. 15. In order to determine whether the antiproliferative activity of the IIbE variant was a result of neutralizing BCR-mediated survival signals, thereby allowing in vitro apoptosis to proceed, an annexin-V staining assay was performed. 1×105 purified primary human B cells were incubated for 24 h at 37° C. in triplicate with 1 µg/ml anti-CD79b and serial dilutions of anti-CD19 or control antibodies in 100 µl RPMI1640 with 10% FBS. After incubation, cells were harvested and stained with PE-conjugated annexin-V (Biovision, Mountain View, Calif.) and 7-aminoactinomycin D (7-AAD, Invitrogen, Carlsbad, Calif.) at 5 µg/ml. The annexin-V-positive/7-AAD-negative cells were acquired using a FACSCanto II flow cytometer, and analyzed with FACSDiva 5 analysis software (BD Biosciences).

The data are shown in FIG. 24. Annexin-V staining of primary human B cells cultured in the presence or absence of anti-CD79b confirmed that apoptosis was suppressed by BCR activation (FIG. 24, cells alone vs. anti-CD79b). This survival signal was neutralized in a dose-dependent manner by anti-CD19-S267E/L328F, but not by anti-RSV-S267E/L328F Fc control or anti-CD19-IgG1 Fv control antibodies. Inhibition of the anti-apoptotic effect, like inhibition of calcium mobilization and cell proliferation, requires coengagement of CD19 and FcγRIIb by a single antibody, because the combination of anti-CD19-IgG1 and anti-RSV-S267E/L328F (Fv and Fc controls, respectively) did not stimulate apoptosis. These data indicate that the anti-CD19 IIbE variant inhibits BCR-induced B cell proliferation by suppressing anti-apoptotic survival signals.

Example 7

Immunoglobulins do not Mediate Effector Functions

In order to evaluate the effect of modulating FcγRIIIa affinity, the immunoglobulins were examined for their ADCC activity. Antibody serial dilutions were carried out in 96 well microtiter plates in triplicates and incubated with Ramos target cells (10,000 total) to opsonize the target cells for ~15 minutes. Ramos is an immortal huma B cell line derived from Burkitt's lymphoma cells. Purified NK cells (50,000 total) using negative selection kit from frozen PBMC prepared from leukophoresis pack using standard Ficoll density gradient were added to appropriate concentration. The final working ADCC reaction was in 100 ul of 1% FBS/RPMI1640 for 4 hours at 37° C. after which, the amount of LDH released from the target cells was detected using fluorescent detection system. The percentage of ADCC was determined by normalizing the background LDH activity (target and NK together without antibody) adjusted experimental LDH activity against the total LDH activity present in the target cells (spontaneous LDH activity present in the target cells alone adjusted TritonX100 lysed target cells). As shown in FIG. 25, many of the variants with enhanced FcγRIIb affinity, yet lower or equivalent FcγRIIIa affinity compared with wild-type IgG1, including S267E, G236D/S267E, and S267E/L328F, lack ADCC activity. This is attributed to their reduced or ablated affinity for the activating FcγRs, particularly FcγRIIIa which is the sole FcγR expressed on NK cells.

Immunoglobulins were also tested for their capacity to mediate phagocytosis by macrophages. Target cells were RS4;11 cells, an immortal human B cell line derived from leukemia cells. Macrophages express a variety of FcγRs, including FcγRI, FcγRIIa, FcγRIIb, and FcγRIIIa. Purified monocytes were differentiated in the presence of macrophage-colony stimulating factor for 5 days into macrophages. Macrophages were mixed with fluorescently labeled (PKH26) RS4;11 cells in 10% human AB serum in RPMI followed by the addition of anti-CD19 antibodies and incubated for 4 hours at 37° C. APC conjugated antibodies to CD14 and CD11b were added to the cell mixture, washed and fixed. Phagocytosis was determined by the percentage CD14+CD11b+ and PKH26 double positive population divided by the total number of stained tumors. The data are shown in FIG. 26. Anti-CD19 IgG1 and the variant S239D/I332E demonstrated phagocytosis. In contrast, variants with enhanced FcγRIIb affinity yet reduced affinity for activating receptors, including S267E/L328F and G236D/S267E, had little or not phagocytic activity, comparable to control antibody that targeted RSV.

Immunoglobulins were also tested for their capacity to mediate CDC. Release of Alamar Blue was used to monitor lysis of a target B cell line by human serum complement. Raji cells (an immortal B cell line) were washed in 10% FBS medium by centrifugation and resuspension, and loaded into 96-well plates at 40,000 cells per well. Variant anti-CD19 antibodies or Rituxan anti-CD20 control were added in ½ fold dilutions to the indicated final concentrations. Human serum complement (Quidel) was diluted 1 to 5 with medium and added to antibody-opsonized target cells. Plates were incubated for 2 hrs at 37° C., Alamar Blue was added, cells were cultured overnight, and fluorescence was measured. Data from this assay are shown in FIG. 27. In contrast to the anti-CD20 control, the variant anti-CD19 antibodies do not mediate CDC activity against B cells.

Example 8

In Vivo Data Demonstrating Potential for Treating Autoimmune or Inflammatory Disorder A hallmark of autoimmunity in mouse and human is dysregulation of FcγRIIb expression resulting in lower surface level of this inhibitory receptor, leading to an elevated level of B cell activation and consequential failure of self-reactive B cell inhibition and production of plasma cells secreting self-antigen specific immunoglobulins. Such self-reactive immunoglobulin immune complexes are etiologic agents in various organ failures in systemic autoimmunity and other arthritic inflammations such as systemic lupus erythematosus (SLE) and rheumatoid arthritis (RA. The immunoglobulins disclosed herein were assessed using a huPBL-SCID mouse model as a proxy, by examining B cell activity measured by the number of B cells and plasma cell development by detecting the antigen specific immunoglobulins. In this method, human PBLs from normal or diseased (e.g., SLE or RA) donors are engrafted to immune-deficient SCID mice and treated with the inhibitory immunoglobulin described herein, then challenged with an antigen to examine the course of B cell development into plasma cells. In such case, the production of antigen-specific immunoglobulins is inhibited from which can be inferred inhibition of both B cell activation and differentiation.

Figure 28A:
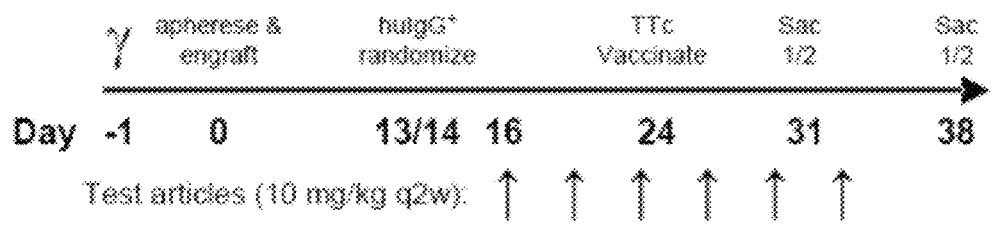
Figure 28B:
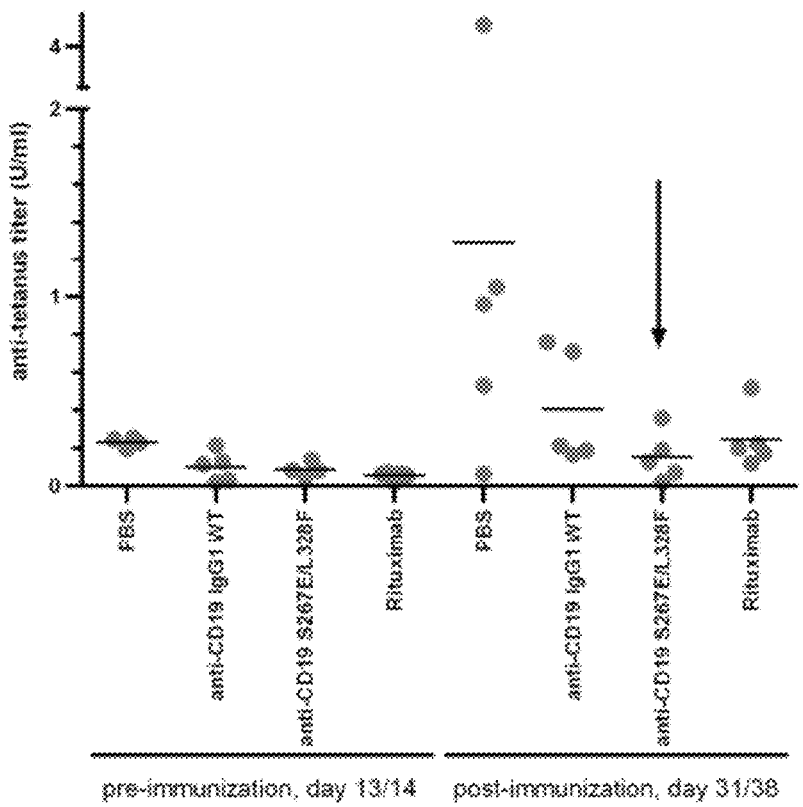

The protocol for this study is provided in FIG. 28A. Four different groups of mice with five mice in each group were engrafted with human PBLs from a healthy donor. At day 16, test articles consisting of PBS (vehicle control), anti-CD19 with native IgG1 Fc (anti-CD19 IgG1 WT), anti-CD19 with IgG1 Fc of enhanced affinity for FcγRIIb (anti-CD19 S267E/L328F) or Rituximab IgG1 anti-CD20 were given 10 mg/kg twice weekly for a total of 6 doses. At day 24, antigen challenge with tetanus toxoid fragment C was given, and mice were sacrificed at days 31 and 38. Tetanus toxoid (TT) specific antibody production was examined. The results of this experiment are shown in FIG. 28B. The data shows that before the antigen challenge, the level of anti-TT specific antibody was very low in all the groups. After immunization, the untreated PBS control group showed the highest level of anti-TT specific antibody level. In comparison, the B cell depleting anti-CD20 antibody produced low level of antigen specific antibody level. After immunization, the anti-CD19 S267E/L328F group showed the lowest level of antigen specific antibodies, whereas the anti-CD19 IgG1 WT produced a higher level of antigen specific antibody. These in vivo data show that the anti-CD19 antibody with enhanced FcγRIIb affinity is capable of inhibiting B cell activation and immunoglobulin secreting plasma cell differentiation, and thus support the potential of the immunoglobulins disclosed herein for treating autoimmune and inflammatory disorders.

Example 9

Co-engagement of FcγRIIb and Other Target Antigens

The use of antibodies to coengage CD19 and FcγRIIb is an example of how simultaneous high affinity engagement of a B cell antigen and FcγRIIb may be used to inhibit activation or proliferation of FcγRIIb+ cells. As discussed above, FcγRIIb is a negative regulator of a number of cell types, including but not limited to B cells, plasma cells, monocytes, macrophages, dendritic cells, neutrophils, basophils, eosinophils, and mast cells. A variety of antigens expressed on these FcγRIIb+ cell types may be also be co-targeted with high affinity FcγRIIb binding to inhibit cellular activation and/or proliferation. FIG. 29 provides a number of examples of antigens and cell types that may be targeted by the immunoglobulins disclosed herein.

At the outset, it is not clear which antigens may serve as effective co-targets with FcγRIIb for modulation of cellular activity. A likely key aspect of a potential co-target is its functional role in the cell, and in particular whether its intracellular signaling pathways (if any) overlap with those of FcγRIIb. CD19 is a co-receptor of the BCR complex, and thus the capacity of high affinity co-engagement of CD19 and FcγRIIb to inhibit B cell activation is likely related to the association of CD19 with BCR and the negative regulatory role of FcγRIIb in inhibiting BCR-stimulated activation. Importantly, however, CD19 is not involved in antigen recognition, which is the specific function of the μ (IgM) component of the BCR. Rather CD19, and other proteins such as CD21, CD22, CD72, CD81, and Leu13, are BCR co-receptors. Of course, targeting of other components of the BCR, including the antigen recognition domain (μ, also referred to as IgM), and the signaling domains CD79a (Igα) and CD79b (10), is also supported by the data herein. However, given the complex biochemical pathways involved in regulating cellular activation and proliferation of these cell types, evaluating which antigens (FIG. 29) may serve as effective co-targets with FcγRIIb for modulation of cellular activity requires experimentation.

In order to evaluate which antigens may be effective co-targets with FcγRIIb for modulating cellular activity, the S267E/L328F (high FcγRIIb affinity) variant, along with WT IgG1 and Fc-KO variant(s) (^236R/L328R and/or G236R/L328R) were cloned into antibodies specific for a variety of other antigens expressed on FcγRIIb+ cells, including CD19, CD20, CD22, CD23, CD40, CD52, and CD79b. In several cases, multiple Fv's targeting the same antigen were constructed in order to assess the epitope-dependence of the effects. FIG. 54A-FIG. 54D list the heavy and light chain variable regions (VH and VL) of the antibodies used. The VH and VL genes targeting these antigens were constructed by gene synthesis, and variants were constructed, expressed, and purified as described above.

The effect of high affinity co-engagement of these antigens with FcγRIIb was evaluated using the ATP-dependent luminescence B cell viability assay as described above. FIGS. 30-35 show the results of these experiments. The data indicate that CD79b is also an effective co-target for using high affinity FcγRIIb co-engagement to inhibit B cell activation. This is consistent with its role as the signaling component of the BCR complex. Results using two additional anti-CD19 antibodies again confirmed the amenability of this antigen to controlling B cell activation using high affinity FcγRIIb co-ligation, irrespective of the specific epitope targeted. In contrast, no effect of high affinity FcγRIIb co-engagement was observed for antibodies with specificity for CD20, CD23, and CD52. Unexpectedly, dual targeting of FcγRIIb using antibodies having specificity for CD22 and CD40 resulted in enhanced B cell activation. In the case of CD22, this may be the result of its role as a negative regulator of BCR activation. In the case of CD40, this may be the result of its role as a positive regulator of B cell activation via engagement at the T cell interface. It is known that some of the antibodies used are agonist, that is to say that their binding of CD40 on B cells and other cells promotes positive signaling and activation of B cells. In a sense these antibodies are mimicking the co-activation signal of a T cell. The antibody (and thus epitope) dependence of this activation is likely related to the capacity of the antibodies to agonize. The reason for the enhanced agonism and stimulation of the B cells upon high affinity (S267E/L328F) engagement of FcγRIIb, but not using WT IgG1 or Fc-KO, is not currently clear, and requires further study.

Select antibodies targeting other antigens were tested further for their capacity to inhibit intracellular calcium mobilization using the assay described above. The results in FIG. 36 agree well with the data from the B cell viability assay. Whereas high affinity co-ligation of FcγRIIb and CD23 had no effect on calcium mobilization, CD79b is an effective co-target for inhibition of calcium. High affinity FcγRIIb co-ligation with CD22 and CD40 resulted in an increase in calcium mobilization, again consistent with the viability results.

In order to screen a larger set of antigens using commercial reagents, a novel method was developed for evaluating the capacity of FcγRIIb/antigen co-engagement to inhibit of cellular activity. This approach uses a haptenized version of an antibody or ligand that has specificity for the target antigen, together with variant versions of an anti-hapten antibody. This concept is illustrated in FIG. 37. A variety of haptens are known in the art that may be used for this approach, including but not limited to FITC, biotin, and nitrophenyl.

The VH and VL genes of the anti-FITC antibody 4-4-20 were constructed by gene synthesis, and variants were constructed with enhanced affinity for FcγRIIb (S267E/L328F), along with WT IgG1 and FcγR knockout variant(s) (^236R/L328R and/or G236R/L328F). Antibodies were constructed, expressed and purified as described above. Commercial antibodies targeting antigens mu (μ), CD19, CD20, CD21, CD24, CD35, CD45RA, CD72, CD79a, CD79b, CD80, CD81, CD86, and HLA-DR were purchased from Beckman Coulter (Fullerton, Calif.), BD Pharmingen (San Jose, Calif.), AbD Serotec (Raleigh, N.C.), or GenTex, Inc. (San Antonio, Tex.). FITC labeling reagent (Pierce Biotech, Inc., Rockford, Ill.) was used to label commercial antibodies according to the supplied protocol at either room temperature or 37° C. for 1 hour. After labeling, un-reacted label was removed using BioSpin P-6 or P-30 columns from BioRad (Hercules, Calif.) and used with varying concentrations of anti-FITC antibodies in proliferation experiments as described above.

The effectiveness of the hapten approach for screening antigens was first confirmed using anti-si and anti-CD19 antibodies, two antigens that are known to mediate inhibitory activity upon high affinity co-engagement with FcγRIIb. FIGS. 38 and 39 show anti-FITC antibody variants with high affinity for FcγRIIb, but not WT IgG1 or Fc-KO variants, are able to inhibit B cell activation in the presence of FITC-labeled anti-mu and anti-CD19 antibodies. These data are consistent with the above approach wherein variants were incorporated directly into the antibody with specificity for CD19 or mu, and thus confirm the use of the hapten approach for screening target antigens for capacity to modulate cellular activity upon high affinity co-engagement with FcγRIIb.

FIGS. 40-52 show data from the ATP-dependent luminescence B cell viability using Fc variant versions of anti-FITC antibodies and antibodies targeting CD20, CD21, CD24, CD35, CD45RA, CD72, CD79a, CD79b, CD80, CD81, CD86, and HLA-DR. Inhibitory activity was observed for targeting of CD79a and CD79b, consistent with their role in BCR signaling. Targeting of CD81 and HLA-DR resulted in possible inhibition. The role of CD81 as a BCR co-receptor would seem to support the result for this antigen. The amenability of these antigens as co-targets for controlling cellular activation using high affinity FcγRIIb binding requires further study. Stimulatory activity was observed for co-targeting of CD72 with high affinity FcγRIIb affinity.

FIG. 53 provides a summary of the results from the target antigen screening by both the Fc variant and hapten approaches. The data indicate that immunoglobulins that coengage with high affinity both FcγRIIb and μ, CD19, CD79a, Cd79b, CD81, and HLA-DR have potential for inhibiting the activation of FcγRIIb+ cells. The data also indicate that immunoglobulins that coengage with high affinity both FcγRIIb and CD22, CD40, and CD72 have potential for stimulating FcγRIIb+ cells. Overall, the results of this work suggest that simultaneous high affinity engagement of FcγRIIb and antigens involved or associated with the BCR complex, including μ, CD79a, CD79b, CD19, CD21, CD22, CD72, CD81, and Leu13, are methods for controlling the activation, proliferation, and/or viability of B cells.

All cited references are herein expressly incorporated by reference in their entirety.

Whereas particular embodiments have been described above for purposes of illustration, it will be appreciated by those skilled in the art that numerous variations of the details may be made without departing from the invention as described in the appended claims.

---

We claim:

1. An anti-CD19 immunoglobulin comprising:
   a light chain; and
   a heavy chain comprising an amino acid sequence of SEQ ID NO: 2 and amino acid substitution(s) in the Fc region selected from L234W, L235I, L235Y, L235R, L235D, G236D, G236N, S267D, S267E, L328F, and L328Y as compared to SEQ ID NO: 4, wherein the numbering is according to the EU index, as in Kabat.

2. The immunoglobulin of claim 1, wherein the immunoglobulin comprises:
   a light chain comprising an amino acid sequence of SEQ ID NO: 7.

3. The immunoglobulin of claim 1, wherein the amino acid substitution(s) in the Fc region are selected from L234W, L235I, L235Y, L235R, G236D, S267D, S267E, and L328F.

4. The immunoglobulin according to claim 1, wherein the amino acid substitution in the Fc region is S267E.

5. The immunoglobulin according to claim 1, wherein the amino acid substitution in the Fc region is L328F.

6. The immunoglobulin according to claim 1, wherein the amino acid substitution in the Fc region is S267E/L328F.

7. A pharmaceutical composition comprising the immunoglobulin according to claim 1, and a pharmaceutically acceptable carrier.

8. The immunoglobulin of claim 2, wherein the amino acid substitution(s) in the Fc region are selected from L234W, L235I, L235Y, L235R, G236D, S267D, S267E, and L328F.

9. The immunoglobulin according to claim 2, wherein the amino acid substitution in the Fc region is S267E.

10. The immunoglobulin according to claim 2, wherein the amino acid substitution in the Fc region is L328F.

11. The immunoglobulin according to claim 2, wherein the amino acid substitution in the Fc region is S267E/L328F.

12. A pharmaceutical composition comprising the immunoglobulin according to claim 2, and a pharmaceutically acceptable carrier.

13. The immunoglobulin of claim 1, wherein the amino acid substitution(s) in the Fc region are selected from L235D/S267E, L235Y/S267E, L235D/S267D, L235I/S267E, L235I/S267D, L235Y/S267D, G236D/S267E, G236D/S267D, S267E/L328F, S267D/L328F, H268D/S267E, H268D/S267D, H268E/S267E, H268E/S267D, and G236N/S267E/L328F.

14. The immunoglobulin of claim 3, wherein the amino acid substitution(s) in the Fc region are selected from L235D/S267E, L235Y/S267E, L235Y/S267D, G236D/S267E, S267E/L328F, H268D/S267E, H268E/S267E, H268E/S267D, and G236D/S267E/L328F.

15. The immunoglobulin of claim 8, wherein the amino acid substitution(s) in the Fc region are selected from L235D/S267E, L235Y/S267E, L235Y/S267D, G236D/S267E, S267E/L328F, H268D/S267E, H268E/S267E, H268E/S267D, and G236D/S267E/L328F.

16. The immunoglobulin of claim 1, wherein the amino acid substitution in the Fc region is S267D.

* * * * *